US012753233B2

(12) United States Patent
Tavernier et al.

(10) Patent No.: US 12,753,233 B2
(45) Date of Patent: Oct. 6, 2026

(54) METHODS OF CANCER TREATMENT WITH PD-L1 TARGETED INTERFERON THERAPEUTIC AGENTS

(71) Applicants: Orionis Biosciences BV, Ghent (BE); VIB VZW, Ghent (BE); Universiteit Gent, Ghent (BE)

(72) Inventors: Jan Tavernier, Balegem (BE); Nikolai Kley, Newton, MA (US)

(73) Assignees: Orionis Biosciences BV, Ghent (BE); VIB VZW, Ghent (BE); UNIVERSITEIT Gent, Ghent (BE)

( * ) Notice: Subject to any disclaimer, the term of this patent is extended or adjusted under 35 U.S.C. 154(b) by 701 days.

(21) Appl. No.: 18/302,364

(22) Filed: Apr. 18, 2023

(65) Prior Publication Data

US 2023/0399406 A1 Dec. 14, 2023

Related U.S. Application Data

(62) Division of application No. 16/075,323, filed as application No. PCT/EP2017/052545 on Feb. 6, 2017, now Pat. No. 11,661,455.

(60) Provisional application No. 62/291,769, filed on Feb. 5, 2016, provisional application No. 62/291,772, filed on Feb. 5, 2016, provisional application No. 62/411,805, filed on Oct. 24, 2016, provisional application No. 62/335,030, filed on May 11, 2016, provisional application No. 62/335,979, filed on May 13, 2016, provisional application No. 62/335,968, filed on May 13, 2016, provisional application No. 62/335,965, filed on May 13, 2016, provisional application No. 62/335,880, filed on May 13, 2016, provisional application No. 62/291,779, filed on Feb. 5, 2016, provisional application No. 62/291,776, filed on Feb. 5, 2016, provisional application No. 62/291,774, filed on Feb. 5, 2016, provisional application No. 62/353,607, filed on Jun. 23, 2016.

(51) Int. Cl.

| | |
|---|---|
| ***C07K 16/28*** | (2006.01) |
| ***A61K 39/00*** | (2006.01) |
| ***A61P 35/00*** | (2006.01) |

(52) U.S. Cl.
CPC .......... *C07K 16/2827* (2013.01); *A61P 35/00* (2018.01); *A61K 2039/505* (2013.01); *C07K 2317/24* (2013.01); *C07K 2317/569* (2013.01); *C07K 2317/622* (2013.01)

(58) Field of Classification Search
CPC .. C07K 16/2827; C07K 2317/24; A61P 35/00
See application file for complete search history.

(56) References Cited

U.S. PATENT DOCUMENTS

| | | | |
|---|---|---|---|
| 5,914,254 | A | 6/1999 | Mascarenhas et al. |
| 8,980,267 | B2 | 3/2015 | Grewal et al. |
| 9,139,634 | B2 | 9/2015 | Morrison et al. |
| 9,534,056 | B2 | 1/2017 | Grewal et al. |
| 2010/0172868 | A1 | 7/2010 | Morrison et al. |
| 2010/0297076 | A1 | 11/2010 | Morrison et al. |
| 2011/0020273 | A1 | 1/2011 | Chang et al. |
| 2011/0081341 | A1 | 4/2011 | Honjo |
| 2011/0104112 | A1 | 5/2011 | Morrison et al. |
| 2011/0224407 | A1 | 9/2011 | Langer et al. |
| 2011/0274658 | A1 | 11/2011 | Silver et al. |
| 2013/0183298 | A1 | 7/2013 | Le et al. |
| 2013/0230517 | A1 | 9/2013 | Grewal et al. |
| 2014/0271462 | A1 | 9/2014 | Ho et al. |
| 2014/0348789 | A1 | 11/2014 | Tavernier et al. |
| 2015/0139951 | A1 | 5/2015 | Grewal et al. |
| 2015/0313965 | A1 | 11/2015 | Pogue et al. |

FOREIGN PATENT DOCUMENTS

| | | | |
|---|---|---|---|
| CN | 103536917 | A | 1/2014 |
| RU | 2011127226 | A | 1/2013 |
| WO | 9102754 | A1 | 3/1991 |
| WO | 2003033720 | A2 | 4/2003 |
| WO | 2006053883 | A1 | 5/2006 |
| WO | 2006115800 | A2 | 11/2006 |
| WO | 2008014612 | A1 | 2/2008 |
| WO | 2008124086 | A2 | 10/2008 |
| WO | 2009003145 | A1 | 12/2008 |
| WO | WO 2009013484 | A1 | 1/2009 |
| WO | 2009039409 | A1 | 3/2009 |
| WO | 2010036918 | A2 | 4/2010 |
| WO | 2010066740 | A1 | 6/2010 |
| WO | 2011020783 | A2 | 2/2011 |
| WO | 2011029870 | A1 | 3/2011 |
| WO | 2012170072 | A1 | 12/2012 |
| WO | WO 2013053008 | A2 | 4/2013 |

(Continued)

OTHER PUBLICATIONS

Ahmad et al. scFv antibody: Principles and clinical Application. Clin. & Dev. Immunol. vol. 2012, Article ID 980250, 2012. (Year: 2012).*

(Continued)

*Primary Examiner* — Elly-Gerald Stoica

(74) *Attorney, Agent, or Firm* — Morgan, Lewis & Bockius LLP

(57) ABSTRACT

The present invention relates, in part, to chimeric proteins that find use in various immunotherapies. Particularly, the present invention provides targeted therapeutic agents that modulate the immune system for the treatment of diseases such as cancer.

10 Claims, 6 Drawing Sheets

Specification includes a Sequence Listing.

(56) References Cited

FOREIGN PATENT DOCUMENTS

| | | | |
|---|---|---|---|
| WO | 2013059885 | A2 | 5/2013 |
| WO | 2013107791 | A1 | 7/2013 |
| WO | 2013134138 | A1 | 9/2013 |
| WO | 2014/028502 | A1 | 2/2014 |
| WO | 2015007520 | A1 | 1/2015 |
| WO | 2015007536 | A1 | 1/2015 |
| WO | 2015007542 | A1 | 1/2015 |
| WO | 2015007903 | A1 | 1/2015 |
| WO | WO 2015018528 | A1 | 2/2015 |
| WO | 2015/061752 | A1 | 4/2015 |
| WO | WO 2016/004060 | A2 | 1/2016 |
| WO | 2017077382 | A1 | 5/2017 |
| WO | 2017/134302 | A2 | 8/2017 |

OTHER PUBLICATIONS

Krah et al. (Single domain antibodies for biomedical applications. Immunopharmac. & immunotox. 38, 21-28, 2016. (Year: 2016).*

Anonymous. https://en.wikipedia.org/wiki/List_of_cancer_types—accessed May 22, 2020. (Year: 2020).*

Anonymous. https://www.cancer.gov/about-cancer/understanding/what-is-cancer—May 22, 2020. (Year: 2020).*

Bald, et al., "Immune Cell-Poor Melanoma Benefit from PD-1 Blockade after Targeted Type I IFN Activation," Cancer Discovery, vol. 4, pp. 674-687, 2014.

Acres, B., et al., "Fusokine Interleukin-2/Interleukin-18, a Novel Potent Innate and Adaptive Immune Stimulator with Decreased Toxicity", Cancer Res., vol. 65, No. 20, (2005), pp. 9536-9546.

Baba, M., et al., "Identification of CCR6, the Specific Receptor for a Novel Lymphocyte-Directed CC Chemokine LARC", The Journal of Biological Chemistry vol. 272, No. 23, (1997), pp. 14893-14898.

Bork "Powers and Pitfalls in Sequence Analysis: The 70% Hurdle", Genome Research, vol. 10 (2000), pp. 398-400.

Bork et al., "Go hunting in sequence databases but watch out for the traps." Trends in Genetics vol. 12 (1996), pp. 425-427.

Boschert et al., Single chain TNF derivatives with individually mutated receptor binding sites reveal differential stoichiometry of ligand receptor complex formation for TNFR1 and TNER2. Cellular Signalling 22 (7): 1088-1096, 2010.

Bremer et al., Superior activity of fusion protein scFvRit:sFasL over cotreatment with rituximab and Fas agonists. Cancer Res. 68:597-604, 2008.

Camacho, N.P., et al., "Structure of an Interleukin-1β Mutant With Reduced Bioactivity Shows Multiple Subtle Changes In Conformation That Affect Protein-Protein Recognition", Biochemistry, vol. 32, No. 34, (1993), pp. 8749-8757.

Coulstock, E., et al., "Liver-Targeting of Interferon-Alpha with Tissue Specific Domain Antibodies." PLOS ONE, vol. 8, No. 2, (2013), pp. 1-11.

De Bruyn, M., et al., "Antibody-Based Fusion Proteins to Target Death Receptors in Cancer", Cancer Letters, vol. 332, (2013), pp. 175-183.

Deffar et al., "Nanobodies—The New Concept in Antibody Engineering" African Journal of Biotechnology, 2009, vol. 8 No. 12, pp. 2645-2652.

Dijkmans, R., et al., "Murine Interferon-γ/Interleukin-1 Fusion Proteins Used as Antigens for the Generation of Hybridomas Producing Monoclonal Anti-Interleukin-1 Antibodies", Cytokine, vol. 3, No. 2, (1991), pp. 134-140.

Dimitrov, D. S., "Engineered CH2 Domains (Nanoantibodies)", mAbs, Landes Bioscience, vol. 1, No. 1, (2009), pp. 26-28.

Frey, K., et al., "Antibody-Based Targeting of Interferon-Alpha to the Tumor Neovasculature: A Critical Evaluation", Integrative Biology, vol. 3, (2011), p. 468-478.

Garlanda et al., "The Interleukin-1 Family: Back to the Future", Immunity, Dec. 12, 2013, 39(6) 1003-1018.

Holler, N., et al: "Two Adjacent Trimeric Fas Ligands are Required for Fas Signaling and Formation of a Death-Inducing Signaling Complex", Molecular and Cellular Biology, vol. 23, No. 4, (2003), pp. 1428-1440.

Huang, T., et al., "A Trimeric Anti-HER2/neu ScFv and Tumor Necrosis Factor-[alpha] Fusion Protein Induces HER2/Neu Signaling and Facilitates Repair of Injured Epithelia", The Journal of Pharmacology and Experimental Therapeutics, vol. 316, No. 3, (2006), pp. 983-991.

Krippner-Heidenreich, A., et al: "Single-Chain TNF, a TNF Derivative with Enhanced Stability and Antitumoral Activity", The Journal of Immunology, vol. 180, (2008), pp. 8176-8183.

Masci, P. et al., "New and Modified Interferon alfas: Preclinical and Clinical Data", Current Oncology Reports, vol. 5, (2003), pp. 108-113.

Ngo et al., "Computational Complexity, Protein Structure Prediction, and the Levinthal Paradox. The Protein Folding Problem and Tertiary Structure Prediction", Edited by: Mertz et al., (Birkhauser, Boston), (1994), pp. 492-495.

Pan, M., et al., "Mutation of the IFNAR-1 Receptor Binding Site of Human IFN-[alpha]2 Generates Type I IFN Competitive Antagonists", Biochemistry, vol. 47, (2008), pp. 12018-12027.

Patris, et al., "Nanoimmunoassay onto a screen printed electrode for HER2 breast cancer biomarker determination", Talanta, 2014, vol. 130 pp. 164-170.

Penafuerte, C., et al., "The Human Ortholog of Granulocyte Macrophage Colony-Stimulating Factor and Interleukin-2 Fusion Protein Induces Potent Ex Vivo Natural Killer Cell Activation and Maturation", Cancer Res, vol. 69, No. 23, (2009), pp. 9020-9028.

Rafei, M., et al., "A MCP1 Fusokine with CCR2-Specific Tumoricidal Activity", Molecular Cancer, vol. 10, No. 121, (2011), pp. 1-11.

Rafei, M., et al., "An Engineered GM-CSF-CCL2 Fusokine Is A Potent Inhibitor of CCR2-Driven Inflammation as Demonstrated in a Murine Model of Inflammatory Arthritis", The Journal of Immunology, vol. 183, (2009), pp. 1759-1766.

Roisman, LC., et al., "Structure of the Interferon-Receptor Complex Determined by Distant Constraints from Double Mutant Cycles and Flexible Docking", PNAS, vol. 98, No. 23, (2001), pp. 13231-13236.

Rovero S et al., "Insertion of the DNA for the 163-171 Peptide of IL 1β Enables a DNA Vaccine Encoding p185neu to Inhibit Mammary Carcinogenesis in Her-2/neu Transgenic BALB/c Mice", Gene Therapy, vol. 8, (2001), pp. 447-452.

Schutyser, E., et al., "The CC Chemokine CCL20 and its Receptor CCR6", Cytokine & Growth Factor Reviews, vol. 14, (2003), pp. 409-426.

Vaneycken, et al., "Preclinical Screening of Anti-HER2 Nanobodies for Molecular Imaging of Breast Cancer", The FASEB Journal, 2011, vol. 25, pp. 2433-2446.

Weber, H., et al., "Single Amino Acid Changes that Render Human IFN-[alpha]2 Biologically Active on Mouse Cells", The EMBO Journal, vol. 6, No. 3, (1987), pp. 591-598.

Wells, "Additivity of mutational effects in proteins." Biochemistry, vol. 29, No. 37, (1990), pp. 8509-8517.

Wesolowski et al., "Single Domain Antibodies: Promising Experimental and Therapeutic Tools in Infection and Immunity", Med Microbiol Immunol. 2009, vol. 198 pp. 157-174.

Barbara, J A et al., "Dissociation of TNF-alpha cytotoxic and proinflammatory activities by p55 receptor- and p75 receptor-selective TNF-alpha mutants," EMBO Journal, vol. 13, No. 4, (1994) pp. 843-850.

Garcin, Genevieve et al., "High Efficiency cell-specific targeting of cytokine activity," Nature Communications, vol. 5, No. 8 (2014).

Loetscher, H et al., "Human Tumor Necrosis Factor alpha (TNFalpha) Mutants with Exclusive Specificity for the 55- kDa or 75-kDa TNF Receptors," Journal of Biological Chemistry, American Society For Biochemistry and Molecular Biology, US, vol. 268, No. 35 (1993) pp. 26350-26357.

Idoyaga et al., "Comparable T helper 1 (Th1) and CD8 T-cell immunity by targeting HIV gag p24 to CD8 dendritic cells within antibodies to Langerin, DEC205, and Clec9A," PNAS, vol. 108, No. 6, Jan. 24, 2011, pp. 2384-2389.

International Search Report in PCT/EP2017/052545 mailed Aug. 30, 2017, 17 pages.

Kircheis, et al., "Biological activity of mutants of human tumour necrosis factor-alpha," Immunology, Jul. 1, 1992, pp. 433-438.

(56) References Cited

OTHER PUBLICATIONS

Lahoud et al., "Targeting Antigen to Mouse Dendritic Cells via Clec9A Induces Potent CD4 T Cell Responses Biased toward a Follicular Helper Phenotype," The Journal Of Immunology, vol. 187, No. 2, Jul. 15, 2011, pp. 842-850.
Minn, "Interferons and the Immunogenic Effects of Cancer Therapy," Trends In Immunology, vol. 36, No. 11, Nov. 1, 2015, pp. 725-737.
Picco et al., "Targeting DNGR-1 (CLEC9A) with antibody/MUC1 peptide conjugates as a vaccine for carcinomas", European Journal Of Immunology, vol. 44, No. 7, Apr. 17, 2014, pp. 1947-1955.
Puskas, et al., "Development of an attenuated interleukin-2 fusion protein than can be activated by tumour-expressed proteases," Immunology, vol. 133, No. 2, Jun. 23, 2011, pp. 206-220.
Sancho et al., "Identification of a dendritic cell receptor that couples sensing of necrosis to immunity", Nature, Nature Publishing Group, United Kingdom, vol. 458, No. 7240, Apr. 16, 2009, pp. 899-903.
Zitvogel et al., "Type I interferons in anticancer immunity," The Journal Of Immunology, vol. 15, No. 7, Jun. 1, 2015, pp. 405-414.

* cited by examiner 1 exp, 6 mice

A.

B.

C.

D.

E.

F.

G.

SEQUENCE LISTING

```
Sequence total quantity: 202
SEQ ID NO: 1            moltype = AA  length = 447
FEATURE                 Location/Qualifiers
REGION                  1..447
                        note = Synthetic Sequence
source                  1..447
                        mol_type = protein
                        organism = synthetic construct
SEQUENCE: 1
QVQLVQSGVE VKKPGASVKV SCKASGYTFT NYYMYWVRQA PGQGLEWMGG INPSNGGTNF  60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                    447

SEQ ID NO: 2            moltype = AA  length = 218
FEATURE                 Location/Qualifiers
REGION                  1..218
                        note = Synthetic Sequence
source                  1..218
                        mol_type = protein
```

```
                         organism = synthetic construct
SEQUENCE: 2
EIVLTQSPAT LSLSPGERAT LSCRASKGVS TSGYSYLHWY QQKPGQAPRL LIYLASYLES  60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 3             moltype = AA  length = 440
FEATURE                  Location/Qualifiers
REGION                   1..440
                         note = Synthetic Sequence
source                   1..440
                         mol_type = protein
                         organism = synthetic construct
SEQUENCE: 3
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                             440

SEQ ID NO: 4             moltype = AA  length = 214
FEATURE                  Location/Qualifiers
REGION                   1..214
                         note = Synthetic Sequence
source                   1..214
                         mol_type = protein
                         organism = synthetic construct
SEQUENCE: 4
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 5             moltype = AA  length = 106
FEATURE                  Location/Qualifiers
REGION                   1..106
                         note = Synthetic Sequence
source                   1..106
                         mol_type = protein
                         organism = synthetic construct
SEQUENCE: 5
EIVLTQSPSS LSASVGDRVT ITCSARSSVS YMHWYQQKPG KAPKLLIYRT SNLASGVPSR  60
FSGSGSGTDF TLTINSLQPE DFATYYCQQR SSFPLTFGGG TKLEIK                 106

SEQ ID NO: 6             moltype = AA  length = 106
FEATURE                  Location/Qualifiers
REGION                   1..106
                         note = Synthetic Sequence
source                   1..106
                         mol_type = protein
                         organism = synthetic construct
SEQUENCE: 6
EIVLTQSPSS LSASVGDRVT ITCSARSSVS YMHWFQQKPG KAPKLWIYRT SNLASGVPSR  60
FSGSGSGTDY TLTINSLQPE DFATYYCQQR SSFPLTFGGG TKLEIK                 106

SEQ ID NO: 7             moltype = AA  length = 106
FEATURE                  Location/Qualifiers
REGION                   1..106
                         note = Synthetic Sequence
source                   1..106
                         mol_type = protein
                         organism = synthetic construct
SEQUENCE: 7
EIVLTQSPSS LSASVGDRVT ITCSARSSVS YMHWFQQKPG KAPKLWIYRT SNLASGVPSR  60
FSGSGSGTDY CLTINSLQPE DFATYYCQQR SSFPLTFGGG TKLEIK                 106

SEQ ID NO: 8             moltype = AA  length = 106
FEATURE                  Location/Qualifiers
REGION                   1..106
                         note = Synthetic Sequence
source                   1..106
                         mol_type = protein
                         organism = synthetic construct
SEQUENCE: 8
EIVLTQSPSS LSASVGDRVT ITCSARSSVS YMHWFQQKPG KAPKLWIYRT SNLASGVPSR  60
```

-continued

```
FSGSGSGTSY CLTINSLQPE DFATYYCQQR SSFPLTFGGG TKLEIK                106

SEQ ID NO: 9            moltype = AA  length = 117
FEATURE                 Location/Qualifiers
REGION                  1..117
                        note = Synthetic Sequence
source                  1..117
                        mol_type = protein
                        organism = synthetic construct
SEQUENCE: 9
QVQLVQSGSE LKKPGASVKI SCKASGYSFS NYGMNWVRQA PGQGLQWMGW INTDSGESTY  60
AEEFKGRFVF SLDTSVSTAY LQITSLTAED TGMYFCAKVG YDALDYWGQG TLVTVSS     117

SEQ ID NO: 10           moltype = AA  length = 117
FEATURE                 Location/Qualifiers
REGION                  1..117
                        note = Synthetic Sequence
source                  1..117
                        mol_type = protein
                        organism = synthetic construct
SEQUENCE: 10
QVQLVQSGSE LKKPGASVKI SCKASGYTFT NYGMNWVRQA PGQGLQWMGW INTDSGESTY  60
AEEFKGRFVF SLDTSVSTAY LQITSLTAED TGMYFCAKVG YDALDYWGQG TLVTVSS     117

SEQ ID NO: 11           moltype = AA  length = 117
FEATURE                 Location/Qualifiers
REGION                  1..117
                        note = Synthetic Sequence
source                  1..117
                        mol_type = protein
                        organism = synthetic construct
SEQUENCE: 11
QVQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 12           moltype = AA  length = 117
FEATURE                 Location/Qualifiers
REGION                  1..117
                        note = Synthetic Sequence
source                  1..117
                        mol_type = protein
                        organism = synthetic construct
SEQUENCE: 12
QIQLVQSGSE LKKPGASVKI SCKASGYTFT NYGMNWVRQA PGQGLQWMGW INTDSGESTY  60
AEEFKGRFVF SLDTSVNTAY LQITSLTAED TGMYFCVRVG YDALDYWGQG TLVTVSS     117

SEQ ID NO: 13           moltype = AA  length = 117
FEATURE                 Location/Qualifiers
REGION                  1..117
                        note = Synthetic Sequence
source                  1..117
                        mol_type = protein
                        organism = synthetic construct
SEQUENCE: 13
QIQLVQSGSE LKKPGASVKI SCKASGYTFT NYGMNWVKQA PGQGLKWMGW INTDSGESTY  60
AEEFKGRFAF SLDTSVNTAY LQITSLNAED TGMYFCVRVG YDALDYWGQG TLVTVSS     117

SEQ ID NO: 14           moltype = AA  length = 254
FEATURE                 Location/Qualifiers
REGION                  1..254
                        note = Synthetic Sequence
source                  1..254
                        mol_type = protein
                        organism = synthetic construct
SEQUENCE: 14
LFTVTVPKEL YIIEHGSNVT LECNFDTGSH VNLGAITASL QKVENDTSPH RERATLLEEQ  60
LPLGKASFHI PQVQVRDEGQ YQCIIIYGVA WDYKYLTLKV KASYRKINTH ILKVPETDEV  120
ELTCQATGYP LAEVSWPNVS VPANTSHSRT PEGLYQVTSV LRLKPPPGRN FSCVFWNTHV  180
RELTLASIDL QSQMEPRTHP TWLLHIFIPF CIIAFIFIAT VIALRKQLCQ KLYSSKDTTK  240
RPVTTTKREV NSAI                                                   254

SEQ ID NO: 15           moltype = AA  length = 453
FEATURE                 Location/Qualifiers
REGION                  1..453
                        note = Synthetic Sequence
source                  1..453
                        mol_type = protein
                        organism = synthetic construct
SEQUENCE: 15
```

-continued

```
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT WEPKSCDKTH TCPPCPAPEL  240
LGGPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPAPIEK TISKAKGQPR EPQVYTLPPS  360
RDELTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                              453

SEQ ID NO: 16          moltype = AA  length = 29
FEATURE                Location/Qualifiers
REGION                 1..29
                       note = Synthetic Sequence
REGION                 9..15
                       note = BRANCHED - SNTSESFK(SNTSESF)FRVTQLAPKAQIKE
source                 1..29
                       mol_type = protein
                       organism = synthetic construct
SEQUENCE: 16
SNTSESFKSN TSESFFRVTQ LAPKAQIKE                                   29

SEQ ID NO: 17          moltype = AA  length = 119
FEATURE                Location/Qualifiers
REGION                 1..119
                       note = Synthetic Sequence
source                 1..119
                       mol_type = protein
                       organism = synthetic construct
SEQUENCE: 17
EVQLQQSGPV LVKPGASVKM SCKASGYTFT DYYMNWVKQS HGKSLEWIGN INPYNGGTTY  60
NQKFKGKATL TVDKSSRTAY MEINSLTSED SAVYYCARGR IYDGSLDYWG QGTALTVSS  119

SEQ ID NO: 18          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 18
DIQMTQFPSS LCASQGGKVT VTCKASQDIN NYMAWYQHKP GKGPRLLIHY TSTLLSGIPS  60
RFSGSGSGRD YSFSISNLEP EDIATYYCLQ YDNLWTFGGG TKLEIK                106

SEQ ID NO: 19          moltype = AA  length = 116
FEATURE                Location/Qualifiers
REGION                 1..116
                       note = Synthetic Sequence
source                 1..116
                       mol_type = protein
                       organism = synthetic construct
SEQUENCE: 19
QVQLQQSGAE LAKPGASVRL SCKASGYTFT NYWMHWVKQR PGQGLEWIGH INPSSGFTTY  60
NQNFKDKATL TADKSSNTAY MQLSSLTYED SAVYFCARED YDVDYWGQGT TLTVSS     116

SEQ ID NO: 20          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 20
DIVMTQSQKF MSTSVGDRVS VTCKASQSVD TNVAWYQQKP GQSPKALIFS ASYRYSGVPD  60
RFTGSGSGTD FTLTINSVQS EDLAEYFCQQ YNSYPYTFGS GTKLEIK               107

SEQ ID NO: 21          moltype = AA  length = 122
FEATURE                Location/Qualifiers
REGION                 1..122
                       note = Synthetic Sequence
source                 1..122
                       mol_type = protein
                       organism = synthetic construct
SEQUENCE: 21
EVQLVESGGG LVKPGGSLKL SCAASGFTFS DYGMHWVRQA PEKGLEWVAY ISSGSYTIYY  60
TDTVKGRFTI SRDNAKNTLF LQMTSLRSED TAMYYCARRG YGSFYEYYFD YWGQGTTLTV  120
SS                                                                122

SEQ ID NO: 22          moltype = AA  length = 106
FEATURE                Location/Qualifiers
```

```
REGION                  1..106
                        note = Synthetic Sequence
source                  1..106
                        mol_type = protein
                        organism = synthetic construct
SEQUENCE: 22
QIVLTQSPAL MSASPGEKVT MTCSASSSVS YMYWYQQKPR SSPKPWIYLT SNLASGVPAR  60
FSGSGSGTSY SLTISSMEAE DAATYYCQQW SSNPFTFGSG TKLEIK                 106

SEQ ID NO: 23           moltype = AA  length = 119
FEATURE                 Location/Qualifiers
REGION                  1..119
                        note = Synthetic Sequence
source                  1..119
                        mol_type = protein
                        organism = synthetic construct
SEQUENCE: 23
EVQLVESGGG LVQAGKSLRL SCAASGSIFS IHAMGWFRQA PGKEREFVAA ITWSGGITYY  60
EDSVKGRFTI SRDNAKNTVY LQMNSLKPED TAIYYCAADR AESSWYDYWG QGTQVTVSS   119

SEQ ID NO: 24           moltype = AA  length = 119
FEATURE                 Location/Qualifiers
REGION                  1..119
                        note = Synthetic Sequence
source                  1..119
                        mol_type = protein
                        organism = synthetic construct
SEQUENCE: 24
EVQLVESGGG LVQAGGSLRL SCAASGSIAS IHAMGWFRQA PGKEREFVAV ITWSGGITYY  60
ADSVKGRFTI SRDNAKNTVY LQMNSLKPED TAIYYCAGDK HQSSWYDYWG QGTQVTVSS   119

SEQ ID NO: 25           moltype = AA  length = 119
FEATURE                 Location/Qualifiers
source                  1..119
                        mol_type = protein
                        organism = synthetic construct
SEQUENCE: 25
EVQLVESGGG LVQAGGSLRL SCAASGSISS IHAMGWFRQA PGKEREFVAA ITWSGGITYY  60
ADSLKGRFTI SRDNAKNTGY LQMNSLKPED TAIYYCAADR AQSSWYDYWG QGTQVTVSS   119

SEQ ID NO: 26           moltype = AA  length = 119
FEATURE                 Location/Qualifiers
REGION                  1..119
                        note = Synthetic Sequence
source                  1..119
                        mol_type = protein
                        organism = synthetic construct
SEQUENCE: 26
EVQLVESGGG LVQAGGSLGL SCAASGSIFS INAMAWFRQA PGKEREFVAL ISWSGGSTYY  60
EDSVKGRFTI SRDNAKNTVY LQMNSLKPED TAIYYCAADR VDSNWYDYWG QGTQVTVSS   119

SEQ ID NO: 27           moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 27
EVQLVESGGG LVQAGGSLRL SCAASGRAFS SGTMGWFRRA PGKEREFVAS IPWSGGRIYY  60
ADSVKGRFTI SRDNAQNTVY LQMNSLKPED TAVYYCAVKE RSTGWDFASW GQCTQVTVSS  120

SEQ ID NO: 28           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 28
QVQLVQSGAE LKQPGASVKM SCKASGYSFT SSWIHWVKQA PGQGLEWIGY IYPSTGFTEY  60
NQKFKDRATL TADKSTSTAY MELSSLRSED SAVYYCARWR DSSGYHAMDY WGQGTSVTVS  120
S                                                                  121

SEQ ID NO: 29           moltype = AA  length = 122
FEATURE                 Location/Qualifiers
REGION                  1..122
                        note = Synthetic Sequence
source                  1..122
```

```
                        mol_type = protein
                        organism = synthetic construct
SEQUENCE: 29
QVQLVQSGAE VKQPGASVKM SCKASGYSFT SSWIHWVKQA PGQGLEWIGY IYPSTGFTEY  60
NQKFKDRATL TADKSTSTAY MELSSLRSED TAVYYDCARW RDSSGYHAMD YWGQGTSVTV  120
SS                                                                 122

SEQ ID NO: 30           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 30
QVQLVQSGHE VKQPGASVKM SCKASGYSFT SSWIHWVKQA PGQGLEWIGY IYPSTGFTEY  60
NQKFKDRATL TADKSTSTAY MELSSLRSED TAVYYCARWR DSSGYHAMDY WGQGTLVTVS  120
S                                                                  121

SEQ ID NO: 31           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 31
QVQLVQSGHE VKQPGASVKM SCKASGYSFT SSWIHWVRQA PGQGLEWIGY IYPSTGFTEY  60
NQKFKDRATL TADKSTSTAY MELSSLRSED TAVYYCARWR DSSGYHAMDY WGQGTLVTVS  120
S                                                                  121

SEQ ID NO: 32           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 32
QVQLVQSGHE VKQPGASVKV SCKASGYSFT SSWIHWVRQA PGQGLEWIGY IYPSTGFTEY  60
NQKFKDRATI TADKSTSTAY MELSSLRSED TAVYYCARWR DSSGYHAMDY WGQGTLVTVS  120
S                                                                  121

SEQ ID NO: 33           moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 33
DIVLTQSPAS LTLSPGQRLT ISCRASQSVS TSGYSYMHWY QQKPDQSPKL LIKFGSNLES  60
GIPARFSGSG SGTDFTLTIS SLEEEDFATY YCQHSWEIPY TFGQGTKLEI K          111

SEQ ID NO: 34           moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 34
DIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K          111

SEQ ID NO: 35           moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 35
EIVLTQSPAT LSLSPGQRLT ISCRASQSVS TSGYSYMHWY QQKPDQSPKL LIKFGSNLES  60
GIPARFSGSG SGTDFTLTIS SLEPEDFATY YCQHSWEIPY TFGQGTKLEI K          111

SEQ ID NO: 36           moltype = AA  length = 111
FEATURE                 Location/Qualifiers
REGION                  1..111
```

-continued

```
                         note = Synthetic Sequence
source                   1..111
                         mol_type = protein
                         organism = synthetic construct
SEQUENCE: 36
DIVLTQSPAT LSLSPGQRLT ISCRASQSVS TSGYSYMHWY QQKPDQSPKL LIKFGSNLES  60
GIPARFSGSG SGTDFTLTIS SLEPEDFAVY YCQHSWEIPY TFGQGTKLEI K           111

SEQ ID NO: 37            moltype = AA  length = 451
FEATURE                  Location/Qualifiers
REGION                   1..451
                         note = Synthetic Sequence
source                   1..451
                         mol_type = protein
                         organism = synthetic construct
SEQUENCE: 37
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                                 451

SEQ ID NO: 38            moltype = AA  length = 215
FEATURE                  Location/Qualifiers
REGION                   1..215
                         note = Synthetic Sequence
source                   1..215
                         mol_type = protein
                         organism = synthetic construct
SEQUENCE: 38
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                             215

SEQ ID NO: 39            moltype = AA  length = 121
FEATURE                  Location/Qualifiers
REGION                   1..121
                         note = Synthetic Sequence
source                   1..121
                         mol_type = protein
                         organism = synthetic construct
SEQUENCE: 39
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 40            moltype = AA  length = 108
FEATURE                  Location/Qualifiers
REGION                   1..108
                         note = Synthetic Sequence
source                   1..108
                         mol_type = protein
                         organism = synthetic construct
SEQUENCE: 40
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK               108

SEQ ID NO: 41            moltype = AA  length = 448
FEATURE                  Location/Qualifiers
REGION                   1..448
                         note = Synthetic Sequence
source                   1..448
                         mol_type = protein
                         organism = synthetic construct
SEQUENCE: 41
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYAST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGK                                     448

SEQ ID NO: 42            moltype = AA  length = 214
```

-continued

```
FEATURE                Location/Qualifiers
REGION                 1..214
                       note = Synthetic Sequence
source                 1..214
                       mol_type = protein
                       organism = synthetic construct
SEQUENCE: 42
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 43          moltype = AA  length = 450
FEATURE                Location/Qualifiers
REGION                 1..450
                       note = Synthetic Sequence
source                 1..450
                       mol_type = protein
                       organism = synthetic construct
SEQUENCE: 43
EVQLLESGGG LVQPGGSLRL SCAASGFTFS SYIMMWVRQA PGKGLEWVSS IYPSGGITFY  60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 44          moltype = AA  length = 216
FEATURE                Location/Qualifiers
REGION                 1..216
                       note = Synthetic Sequence
source                 1..216
                       mol_type = protein
                       organism = synthetic construct
SEQUENCE: 44
QSALTQPASV SGSPGQSITI SCTGTSSDVG GYNYVSWYQQ HPGKAPKLMI YDVSNRPSGV  60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 45          moltype = AA  length = 123
FEATURE                Location/Qualifiers
REGION                 1..123
                       note = Synthetic Sequence
source                 1..123
                       mol_type = protein
                       organism = synthetic construct
SEQUENCE: 45
QVQLVQSGAE VKKPGSSVKV SCKTSGDTFS TYAISWVRQA PGQGLEWMGG IIPIFGKAHY  60
AQKFQGRVTI TADESTSTAY MELSSLRSED TAVYFCARKF HFVSGSPFGM DVWGQGTTVT  120
VSS                                                                123

SEQ ID NO: 46          moltype = AA  length = 106
FEATURE                Location/Qualifiers
REGION                 1..106
                       note = Synthetic Sequence
source                 1..106
                       mol_type = protein
                       organism = synthetic construct
SEQUENCE: 46
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                 106

SEQ ID NO: 47          moltype = AA  length = 117
FEATURE                Location/Qualifiers
REGION                 1..117
                       note = Synthetic Sequence
source                 1..117
                       mol_type = protein
                       organism = synthetic construct
SEQUENCE: 47
QVQLVQSGAE VKKPGASVKV SCKASGYTFT DYGFSWVRQA PGQGLEWMGW ITAYNGNTNY  60
AQKLQGRVTM TTDTSTSTVY MELRSLRSDD TAVYYCARDY FYGMDVWGQG TTVTVSS     117

SEQ ID NO: 48          moltype = AA  length = 107
FEATURE                Location/Qualifiers
REGION                 1..107
```

```
                        note = Synthetic Sequence
source                  1..107
                        mol_type = protein
                        organism = synthetic construct
SEQUENCE: 48
EIVLTQSPAT LSLSPGERAT LSCRASQSVS SYLVWYQQKP GQAPRLLIYD ASNRATGIPA  60
RFSGSGSGTD FTLTISSLEP EDFAVYYCQQ RSNWPRTFGQ GTKVEIK                107

SEQ ID NO: 49           moltype = AA  length = 118
FEATURE                 Location/Qualifiers
REGION                  1..118
                        note = Synthetic Sequence
source                  1..118
                        mol_type = protein
                        organism = synthetic construct
SEQUENCE: 49
QVQLVQSGAE VKKPGASVKV SCKASGYTFT SYDVHWVRQA PGQRLEWMGW LHADTGITKF  60
SQKFQGRVTI TRDTSASTAY MELSSLRSED TAVYYCARER IQLWFDYWGQ GTLVTVSS    118

SEQ ID NO: 50           moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 50
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK                107

SEQ ID NO: 51           moltype = AA  length = 120
FEATURE                 Location/Qualifiers
REGION                  1..120
                        note = Synthetic Sequence
source                  1..120
                        mol_type = protein
                        organism = synthetic construct
SEQUENCE: 51
QVQLVQSGAE VKKPGSSVKV SCKVSGGIFS TYAINWVRQA PGQGLEWMGG IIPIFGTANH  60
AQKFQGRVTI TADESTSTAY MELSSLRSED TAVYYCARDQ GIAAALFDYW GQGTLVTVSS  120

SEQ ID NO: 52           moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 52
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK               108

SEQ ID NO: 53           moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 53
EVQLVESGGG LVQPGRSLRL SCAVSGFTFD DYVVHWVRQA PGKGLEWVSG ISGNSGNIGY  60
ADSVKGRFTI SRDNAKNSLY LQMNSLRAED TALYYCAVPF DYWGQGTLVT VSS         113

SEQ ID NO: 54           moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 54
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK                107

SEQ ID NO: 55           moltype = AA  length = 123
FEATURE                 Location/Qualifiers
REGION                  1..123
                        note = Synthetic Sequence
source                  1..123
```

-continued

```
                        mol_type = protein
                        organism = synthetic construct
SEQUENCE: 55
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HFVSGSPFGM DVWGQGTTVT  120
VSS                                                               123

SEQ ID NO: 56           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 56
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 57           moltype = AA  length = 123
FEATURE                 Location/Qualifiers
REGION                  1..123
                        note = Synthetic Sequence
source                  1..123
                        mol_type = protein
                        organism = synthetic construct
SEQUENCE: 57
QVQLVQSGAE VKKPGSSVKV SCKTSGGTFS SYAISWVRQA PGQGLEWMGG IIPIFGKAHY  60
AQKFQGRVTI TADESTTTAY MELSSLRSED TAVYYCARKY DYVSGSPFGM DVWGQGTTVT  120
VSS                                                               123

SEQ ID NO: 58           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 58
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 59           moltype = AA  length = 121
FEATURE                 Location/Qualifiers
REGION                  1..121
                        note = Synthetic Sequence
source                  1..121
                        mol_type = protein
                        organism = synthetic construct
SEQUENCE: 59
QVQLVQSGAE VKKPGSSVKV SCKASGGTFS SYAINWVRQA PGQGLEWMGG IIPIFGSANY  60
AQKFQDRVTI TADESTSAAY MELSSLRSED TAVYYCARDS SGWSRYYMDV WGQGTTVTVS  120
S                                                                 121

SEQ ID NO: 60           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 60
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPFGGG TKVEIK                106

SEQ ID NO: 61           moltype = AA  length = 123
FEATURE                 Location/Qualifiers
REGION                  1..123
                        note = Synthetic Sequence
source                  1..123
                        mol_type = protein
                        organism = synthetic construct
SEQUENCE: 61
QVQLVQSGAE VKEPGSSVKV SCKASGGTFN SYAISWVRQA PGQGLEWMGG IIPLFGIAHY  60
AQKFQGRVTI TADESTNTAY MDLSSLRSED TAVYYCARKY SYVSGSPFGM DVWGQGTTVT  120
VSS                                                               123

SEQ ID NO: 62           moltype = AA  length = 106
FEATURE                 Location/Qualifiers
REGION                  1..106
```

-continued

```
                         note = Synthetic Sequence
source                   1..106
                         mol_type = protein
                         organism = synthetic construct
SEQUENCE: 62
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TRLEIK                106

SEQ ID NO: 63            moltype = AA  length = 121
FEATURE                  Location/Qualifiers
REGION                   1..121
                         note = Synthetic Sequence
source                   1..121
                         mol_type = protein
                         organism = synthetic construct
SEQUENCE: 63
EVQLVESGGG LVQPGRSLRL SCAASGITFD DYGMHWVRQA PGKGLEWVSG ISWNRGRIEY  60
ADSVKGRFTI SRDNAKNSLY LQMNSLRAED TALYYCAKGR FRYFDWFLDY WGQGTLVTVS  120
S                                                                 121

SEQ ID NO: 64            moltype = AA  length = 107
FEATURE                  Location/Qualifiers
REGION                   1..107
                         note = Synthetic Sequence
source                   1..107
                         mol_type = protein
                         organism = synthetic construct
SEQUENCE: 64
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPFTFGP GTKVDIK               107

SEQ ID NO: 65            moltype = AA  length = 118
FEATURE                  Location/Qualifiers
REGION                   1..118
                         note = Synthetic Sequence
source                   1..118
                         mol_type = protein
                         organism = synthetic construct
SEQUENCE: 65
EVKLQESGPS LVKPSQTLSL TCSVTGYSIT SDYWNWIRKF PGNKLEYVGY ISYTGSTYYN  60
PSLKSRISIT RDTSKNQYYL QLNSVTSEDT ATYYCARYGG WLSPFDYWGQ GTTLTVSS    118

SEQ ID NO: 66            moltype = AA  length = 107
FEATURE                  Location/Qualifiers
REGION                   1..107
                         note = Synthetic Sequence
source                   1..107
                         mol_type = protein
                         organism = synthetic construct
SEQUENCE: 66
DIVMTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK               107

SEQ ID NO: 67            moltype = AA  length = 120
FEATURE                  Location/Qualifiers
REGION                   1..120
                         note = Synthetic Sequence
source                   1..120
                         mol_type = protein
                         organism = synthetic construct
SEQUENCE: 67
EVQLQESGPG LVAPSQSLSI TCTVSGFSLT TYSINWIRQP PGKGLEWLGV MWAGGGTNSN  60
SVLKSRLIIS KDNSKSQVFL KMNSLQTDDT ARYYCARYYG NSPYYAIDYW GQGTSVTVSS  120

SEQ ID NO: 68            moltype = AA  length = 107
FEATURE                  Location/Qualifiers
REGION                   1..107
                         note = Synthetic Sequence
source                   1..107
                         mol_type = protein
                         organism = synthetic construct
SEQUENCE: 68
DIVTTQSHKL MSTSVGDRVS ITCKASQDVG TAVAWYQQKP GQSPKLLIYW ASTRHTGVPD  60
RFTGSGSGTD FTLTISNVQS EDLADYFCQQ DSSYPLTFGA GTKVELK               107

SEQ ID NO: 69            moltype = AA  length = 118
FEATURE                  Location/Qualifiers
REGION                   1..118
                         note = Synthetic Sequence
```

```
source                  1..118
                        mol_type = protein
                        organism = synthetic construct
SEQUENCE: 69
EVKLQESGPS LVKPSQTLSL TCSVTGYSII SDYWNWIRKF PGNKLEYLGY ISYTGSTYYN  60
PSLKSRISIT RDTSKNQYYL QLNSVTTEDT ATYYCARRGG WLLPFDYWGQ GTTLTVSS    118

SEQ ID NO: 70           moltype = AA  length = 113
FEATURE                 Location/Qualifiers
REGION                  1..113
                        note = Synthetic Sequence
source                  1..113
                        mol_type = protein
                        organism = synthetic construct
SEQUENCE: 70
DIVMTQSPSS LAVSVGEKVS MGCKSSQSLL YSSNQKNSLA WYQQKPGQSP KLLIDWASTR  60
ESGVPDRFTG SGSGTDFTLT ISSVKAEDLA VYYCQQYYGY PLTFGAGTKL ELK         113

SEQ ID NO: 71           moltype = AA  length = 118
FEATURE                 Location/Qualifiers
REGION                  1..118
                        note = Synthetic Sequence
source                  1..118
                        mol_type = protein
                        organism = synthetic construct
SEQUENCE: 71
EVKLQESGPS LVKPGASVKL SCKASGYTFT SYDINWVKQR PGQGLEWIGW IFPRDNNTKY  60
NENFKGKATL TVDTSSTTAY MELHSLTSED SAVYFCTKEN WVGDFDYWGQ GTTLTLSS    118

SEQ ID NO: 72           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 72
DIVMTQSPAI MSASPGEKVT MTCSASSSIR YMHWYQQKPG TSPKRWISDT SKLTSGVPAR  60
FSGSGSGTSY ALTISSMEAE DAATYYCHQR SSYPWTFGGG TKLEIK                 106

SEQ ID NO: 73           moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 73
EVQLQQSGPD LVTPGASVRI SCQASGYTFP DYYMNWVKQS HGKSLEWIGD IDPNYGGTTY  60
NQKFKGKAIL TVDRSSSTAY MELRSLTSED SAVYYCARGA LTDWGQGTSL TVSS         114

SEQ ID NO: 74           moltype = AA  length = 106
FEATURE                 Location/Qualifiers
REGION                  1..106
                        note = Synthetic Sequence
source                  1..106
                        mol_type = protein
                        organism = synthetic construct
SEQUENCE: 74
QIVLSQSPAI LSASPGEKVT MTCRASSSVS YIYWFQQKPG SSPKPWIYAT FNLASGVPAR  60
FSGSGSGTSY SLTISRVETE DAATYYCQQW SNNPLTFGAG TKLELK                 106

SEQ ID NO: 75           moltype = AA  length = 115
FEATURE                 Location/Qualifiers
REGION                  1..115
                        note = Synthetic Sequence
source                  1..115
                        mol_type = protein
                        organism = synthetic construct
SEQUENCE: 75
EVQLVQSGPE LKKPGASVKM SCKASGYTFT SYVMHWVKQA PGQRLEWIGY VNPFNDGTKY  60
NEMFKGRATL TSDKSTSTAY MELSSLRSED SAVYYCARQA WGYPWGQGTL VTVSS        115

SEQ ID NO: 76           moltype = AA  length = 115
FEATURE                 Location/Qualifiers
REGION                  1..115
                        note = Synthetic Sequence
source                  1..115
                        mol_type = protein
```

-continued

```
                      organism = synthetic construct
SEQUENCE: 76
EVQLVQSGAE VKKPGASVKM SCKASGYTFT SYVMHWVKQA PGQRLEWIGY VNPFNDGTKY  60
NEMFKGRATL TSDKSTSTAY MELSSLRSED TAVYYCARQA WGYPWGQGTL VTVSS       115

SEQ ID NO: 77         moltype = AA  length = 115
FEATURE               Location/Qualifiers
REGION                1..115
                      note = Synthetic Sequence
source                1..115
                      mol_type = protein
                      organism = synthetic construct
SEQUENCE: 77
EVQLVQSGAE VKKPGASVKM SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 78         moltype = AA  length = 115
FEATURE               Location/Qualifiers
REGION                1..115
                      note = Synthetic Sequence
source                1..115
                      mol_type = protein
                      organism = synthetic construct
SEQUENCE: 78
EVQLVQSGAE VKKPGASVKV SCKASGYTFT SYVMHWVRQA PGQRLEWIGY VNPFNDGTKY  60
NEMFKGRATL TSDKSTSTAY MELSSLRSED TAVYYCARQA WGYPWGQGTL VTVSS       115

SEQ ID NO: 79         moltype = AA  length = 115
FEATURE               Location/Qualifiers
REGION                1..115
                      note = Synthetic Sequence
source                1..115
                      mol_type = protein
                      organism = synthetic construct
SEQUENCE: 79
EVQLVQSGAE VKKPGASVKV SCKASGYTFT SYVMHWVRQA PGQRLEWIGY VNPFNDGTKY  60
NEMFKGRATI TSDKSTSTAY MELSSLRSED TAVYYCARQA WGYPWGQGTL VTVSS       115

SEQ ID NO: 80         moltype = AA  length = 111
FEATURE               Location/Qualifiers
REGION                1..111
                      note = Synthetic Sequence
source                1..111
                      mol_type = protein
                      organism = synthetic construct
SEQUENCE: 80
DIVLTQSPAS LALSPGERAT LSCRATESVE YYGTSLVQWY QQKPGQPPKL LIYAASSVDS  60
GVPSRFSGSG SGTDFTLTIN SLEEEDAAMY FCQQSRRVPY TFGQGTKLEI K           111

SEQ ID NO: 81         moltype = AA  length = 111
FEATURE               Location/Qualifiers
REGION                1..111
                      note = Synthetic Sequence
source                1..111
                      mol_type = protein
                      organism = synthetic construct
SEQUENCE: 81
DIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 82         moltype = AA  length = 111
FEATURE               Location/Qualifiers
REGION                1..111
                      note = Synthetic Sequence
source                1..111
                      mol_type = protein
                      organism = synthetic construct
SEQUENCE: 82
EIVLTQSPAT LSLSPGERAT LSCRATESVE YYGTSLVQWY QQKPGQPPKL LIYAASSVDS  60
GVPSRFSGSG SGTDFTLTIN SLEAEDAAMY FCQQSRRVPY TFGQGTKLEI K           111

SEQ ID NO: 83         moltype = AA  length = 111
FEATURE               Location/Qualifiers
REGION                1..111
                      note = Synthetic Sequence
source                1..111
                      mol_type = protein
                      organism = synthetic construct
SEQUENCE: 83
```

```
DIVLTQSPAT LSLSPGERAT LSCRATESVE YYGTSLVQWY QQKPGQPPKL LIYAASSVDS  60
GVPSRFSGSG SGTDFTLTIN SLEAEDAATY FCQQSRRVPY TFGQGTKLEI K           111

SEQ ID NO: 84          moltype = AA  length = 120
FEATURE                Location/Qualifiers
REGION                 1..120
                       note = Synthetic Sequence
source                 1..120
                       mol_type = protein
                       organism = synthetic construct
SEQUENCE: 84
EVQLVESGGG LVKPGGSLRL SCAASGFTFS TYSMNWVRQA PGKGLEWVSS ISSSGDYIYY  60
ADSVKGRFTI SRDNAKNSLF LQMNSLKAED TAVYYCARDL VTSMVAFDYW GQGTLVTVSS  120

SEQ ID NO: 85          moltype = AA  length = 108
FEATURE                Location/Qualifiers
REGION                 1..108
                       note = Synthetic Sequence
source                 1..108
                       mol_type = protein
                       organism = synthetic construct
SEQUENCE: 85
SYELTQPPSV SVSPGQAARI TCSGDALPQK YVFWYQQKSG QAPVLVIYED SKRPSGIPER  60
FSGSSSGTMA TLTISGAQVE DEADYYCYST DRSGNHRVFG GGTRLTVL               108

SEQ ID NO: 86          moltype = AA  length = 120
FEATURE                Location/Qualifiers
REGION                 1..120
                       note = Synthetic Sequence
source                 1..120
                       mol_type = protein
                       organism = synthetic construct
SEQUENCE: 86
EVQLVESGGG LVQPGGSLRL SCAASGFTFS SYWMSWVRQA PGKGLEWVAN IKQDGGEQYY  60
VDSVKGRFTI SRDNAKNSLY LQMNSLRAED TAVYYCARDW NYGYYDMDVW GQGTTVTVSS  120

SEQ ID NO: 87          moltype = AA  length = 108
FEATURE                Location/Qualifiers
REGION                 1..108
                       note = Synthetic Sequence
source                 1..108
                       mol_type = protein
                       organism = synthetic construct
SEQUENCE: 87
EIVLTQSPGT LSLSPGERAT LSCRASQSVS SNYLAWFQQK PGQAPRLLIF GTSSRATGIP  60
DRFSGSGSGT DFTLTISRLE PEDFAVYYCQ QYGSSIFTFG PGTKVDIK               108

SEQ ID NO: 88          moltype = AA  length = 121
FEATURE                Location/Qualifiers
REGION                 1..121
                       note = Synthetic Sequence
source                 1..121
                       mol_type = protein
                       organism = synthetic construct
SEQUENCE: 88
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                  121

SEQ ID NO: 89          moltype = AA  length = 108
FEATURE                Location/Qualifiers
REGION                 1..108
                       note = Synthetic Sequence
source                 1..108
                       mol_type = protein
                       organism = synthetic construct
SEQUENCE: 89
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTEVEIK               108

SEQ ID NO: 90          moltype = AA  length = 121
FEATURE                Location/Qualifiers
REGION                 1..121
                       note = Synthetic Sequence
source                 1..121
                       mol_type = protein
                       organism = synthetic construct
SEQUENCE: 90
EVQLLESGGG LVQPGGSLRL SCAASGFTFS NYAMSWVRQA PGKGLEWVSA IRGSGGSTYY  60
```

-continued

```
ADSVKGRFTI SRDNSKNTLY LQMNSLRAED TAVYYCAKDL HYDSSGYLDY WGQGTLVTVS  120
S                                                                 121

SEQ ID NO: 91          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 91
DIQMTQSPSS VSASVGDRVT ITCRASQGIR SWLAWYQQKP GKAPKLLIYA ISRLQSGVPS  60
RFSGSGSGTD FTLTISSLQP EDFATYYCQQ ANSFPLTFGG GTKVEIK               107

SEQ ID NO: 92          moltype = AA  length = 119
FEATURE                Location/Qualifiers
REGION                 1..119
                       note = Synthetic Sequence
source                 1..119
                       mol_type = protein
                       organism = synthetic construct
SEQUENCE: 92
EVQLVESGGG LVQPGGSLRL SCAASGFTFS SYWMSWVRQA PGKGLEWVAN IKQDGGEKYY  60
VDSVKGRFTI SRDNAKNSLF LQMNSLRAED TAVYYCARVQ LYSDYFDYWG QGTLVTVSS   119

SEQ ID NO: 93          moltype = AA  length = 107
FEATURE                Location/Qualifiers
REGION                 1..107
                       note = Synthetic Sequence
source                 1..107
                       mol_type = protein
                       organism = synthetic construct
SEQUENCE: 93
DIQMTQSPSS VSASVGDRVT ITCRASQGIS SWLAWYQQKS GKAPKLLIYA ASGLQSGVPS  60
RFSGSGSGTD FTLTISSLQP EDLATYYCQQ SHSLPPTFGQ GTKVEIK               107

SEQ ID NO: 94          moltype = AA  length = 121
FEATURE                Location/Qualifiers
REGION                 1..121
                       note = Synthetic Sequence
source                 1..121
                       mol_type = protein
                       organism = synthetic construct
SEQUENCE: 94
EVQLLESGGD LVQPGGSLRL SCAASGFTFN SYAMSWVRQA PGKGLEWVST ISGSGGFTFS  60
ADSVKGRFTI SRDNSKNTLF LQMNSLRVED SAVYSCAKVL VGFNNGCWDY WGQGTLVTVS  120
S                                                                 121

SEQ ID NO: 95          moltype = AA  length = 108
FEATURE                Location/Qualifiers
REGION                 1..108
                       note = Synthetic Sequence
source                 1..108
                       mol_type = protein
                       organism = synthetic construct
SEQUENCE: 95
SYVLTQPPSV SVAPGQTARI TCGGNNIGSK SVHWYQQKPG QAPVLVVYDD SDRPSGIPER  60
FSGSNSGNTA TLTISRVEAG DEADYYCQVW DSSNDHVVFG GGTKLTVL              108

SEQ ID NO: 96          moltype = AA  length = 120
FEATURE                Location/Qualifiers
REGION                 1..120
                       note = Synthetic Sequence
source                 1..120
                       mol_type = protein
                       organism = synthetic construct
SEQUENCE: 96
EVQLVESGGG LVKPGGSLRL SCAASGFTFS TYSMNWVRQA PGKGLEWVSS ISSSGDYIYY  60
ADSVKGRFTI SRDNAKNSLY LQMNSLRAED TAVYYCARDL VTSMVAFDYW GQGTLVTVSS  120

SEQ ID NO: 97          moltype = AA  length = 108
FEATURE                Location/Qualifiers
REGION                 1..108
                       note = Synthetic Sequence
source                 1..108
                       mol_type = protein
                       organism = synthetic construct
SEQUENCE: 97
SYELTQPPSV SVSPGQTARI TCSGDALPQK YVFWYQQKSG QAPVLVIYED SKRPSGIPER  60
```

```
FSGSSSGTMA TLTISGAQVE DEADYYCYST DRSGNHRVFG GGTKLTVL              108

SEQ ID NO: 98          moltype = AA  length = 121
FEATURE                Location/Qualifiers
REGION                 1..121
                       note = Synthetic Sequence
source                 1..121
                       mol_type = protein
                       organism = synthetic construct
SEQUENCE: 98
EVQLVESGGG LVQPGGSLRL SCAASGFTFS RYWMSWVRQA PGKGLEWVAN IKQDGSEKYY  60
VDSVKGRFTI SRDNAKNSLY LQMNSLRAED TAVYYCAREG GWFGELAFDY WGQGTLVTVS  120
S                                                                 121

SEQ ID NO: 99          moltype = AA  length = 108
FEATURE                Location/Qualifiers
REGION                 1..108
                       note = Synthetic Sequence
source                 1..108
                       mol_type = protein
                       organism = synthetic construct
SEQUENCE: 99
EIVLTQSPGT LSLSPGERAT LSCRASQRVS SSYLAWYQQK PGQAPRLLIY DASSRATGIP  60
DRFSGSGSGT DFTLTISRLE PEDFAVYYCQ QYGSLPWTFG QGTKVEIK              108

SEQ ID NO: 100         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 100
QVQLVQSGAE VKKPGASVKV SCKASGYTFT SYWMYWVRQA TGQGLEWMGR IDPNSGSTKY  60
NEKFKNRFTI SRDDSKNTAY LQMNSLKTED TAVYYCARDY RKGLYAMDYW GQGTTVTVSS  120

SEQ ID NO: 101         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 101
EVQLVQSGAE VKKPGATVKI SCKVSGYTFT SYWMYWVRQA TGQGLEWMGR IDPNSGSTKY  60
NEKFKNRVTI TADKSTSTAY MELSSLRSED TAVYYCARDY RKGLYAMDYW GQGTTVTVSS  120

SEQ ID NO: 102         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 102
EVQLVQSGAE VKKPGESLRI SCKGSGYTFT SYWMYWVRQA PGQGLEWMGR IDPNSGSTKY  60
NEKFKNRVTI SVDTSKNQFS LKLSSVTAAD TAVYYCARDY RKGLYAMDYW GQGTTVTVSS  120

SEQ ID NO: 103         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 103
EVQLVQSGAE VKKPGATVKI SCKVSGYTFT SYWMYWIRQS PSRGLEWLGR IDPNSGSTKY  60
NEKFKNRLTI SKDTSKNQVV LTMTNMDPVD TATYYCARDY RKGLYAMDYW GQGTTVTVSS  120

SEQ ID NO: 104         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 104
EVQLVQSGAE VKKPGESLRI SCKGSGYTFT SYWMYWIRQP PGKGLEWIGR IDPNSGSTKY  60
NEKFKNRVTI TADKSTSTAY MELSSLRSED TAVYYCARDY RKGLYAMDYW GQGTTVTVSS  120
```

```
SEQ ID NO: 105         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 105
QVQLVQSGAE VKKPGASVKV SCKASGYTFT SYWMYWIRQS PSRGLEWLGR IDPNSGSTKY  60
NEKFKNRFTI SRDDSKNTAY LQMNSLKTED TAVYYCARDY RKGLYAMDYW GQGTTVTVSS  120

SEQ ID NO: 106         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 106
EVQLVQSGAE VKKPGESLRI SCKGSGYTFT SYWMYWVRQA RGQRLEWIGR IDPNSGSTKY  60
NEKFKNRLTI SKDTSKNQVV LTMTNMDPVD TATYYCARDY RKGLYAMDYW GQGTTVTVSS  120

SEQ ID NO: 107         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 107
QITLKESGPT LVKPTQTLTL TCTFSGYTFT SYWMYWVRQA PGKGLEWVSR IDPNSGSTKY  60
NEKFKNRVTI TADKSTSTAY MELSSLRSED TAVYYCARDY RKGLYAMDYW GQGTTVTVSS  120

SEQ ID NO: 108         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 108
EVQLVQSGAE VKKPGATVKI SCKVSGYTFT SYWMYWVRQA RGQRLEWIGR IDPNSGSTKY  60
NEKFKNRFTI SRDNSKNTLY LQMNSLRAED TAVYYCARDY RKGLYAMDYW GQGTTVTVSS  120

SEQ ID NO: 109         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 109
DIVMTQTPLS LPVTPGEPAS ISCKASQDVG TAVAWYLQKP GQSPQLLIYW ASTRHTGIPA  60
RFSGSGSGTE FTLTISSLQS EDFAVYYCQQ YNSYPLTFGQ GTKVEIK                107

SEQ ID NO: 110         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 110
DIQMTQSPSS LSASVGDRVT ITCKASQDVG TAVAWYLQKP GQSPQLLIYW ASTRHTGVPS  60
RFSGSGSGTD FTLTISSLQP EDFATYYCQQ YNSYPLTFGQ GTKVEIK                107

SEQ ID NO: 111         moltype = AA  length = 107
FEATURE                Location/Qualifiers
REGION                 1..107
                       note = Synthetic Sequence
source                 1..107
                       mol_type = protein
                       organism = synthetic construct
SEQUENCE: 111
EIVLTQSPDF QSVTPKEKVT ITCKASQDVG TAVAWYLQKP GQSPQLLIYW ASTRHTGVPD  60
RFSGSGSGTD FTLKISRVEA EDVGVYYCQQ YNSYPLTFGQ GTKVEIK                107

SEQ ID NO: 112         moltype = AA  length = 107
```

-continued

```
FEATURE                 Location/Qualifiers
REGION                  1..107
                        note = Synthetic Sequence
source                  1..107
                        mol_type = protein
                        organism = synthetic construct
SEQUENCE: 112
EIVLTQSPDF QSVTPKEKVT ITCKASQDVG TAVAWYLQKP GQSPQLLIYW ASTRHTGVPS  60
RFSGSGSGTD FTFTISSLQP EDIATYYCQQ YNSYPLTFGQ GTKVEIK                107

SEQ ID NO: 113          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 113
EIVLTQSPAT LSLSPGERAT LSCKASQDVG TAVAWYLQKP GQSPQLLIYW ASTRHTGIPP  60
RFSGSGYGTD FTLTINNIES EDAAYYFCQQ YNSYPLTFGQ GTKVEIK                107

SEQ ID NO: 114          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 114
DVVMTQSPLS LPVTLGQPAS ISCKASQDVG TAVAWYQQKP GQAPRLLIYW ASTRHTGVPS  60
RFSGSGSGTE FTLTISSLQP DDFATYYCQQ YNSYPLTFGQ GTKVEIK                107

SEQ ID NO: 115          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 115
DIQMTQSPSS LSASVGDRVT ITCKASQDVG TAVAWYQQKP GQAPRLLIYW ASTRHTGVPS  60
RFSGSGSGTD FTFTISSLQP EDIATYYCQQ YNSYPLTFGQ GTKVEIK                107

SEQ ID NO: 116          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 116
AIQLTQSPSS LSASVGDRVT ITCKASQDVG TAVAWYLQKP GQSPQLLIYW ASTRHTGVPS  60
RFSGSGSGTD FTFTISSLEA EDAATYYCQQ YNSYPLTFGQ GTKVEIK                107

SEQ ID NO: 117          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 117
EIVLTQSPDF QSVTPKEKVT ITCKASQDVG TAVAWYQQKP GQAPRLLIYW ASTRHTGVPS  60
RFSGSGSGTE FTLTISSLQP DDFATYYCQQ YNSYPLTFGQ GTKVEIK                107

SEQ ID NO: 118          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 118
EVKLVESGGG LVKPGGSLKL SCAASGFIFR SYGMSWVRQT PEKRLEWVAS ISSGGSTYYP  60
DSVKGRFTIS RDNARNILYL QMSSLRSEDT AMYDCARGYD SGFAYWGQGT LVTVSE      116

SEQ ID NO: 119          moltype = AA  length = 116
FEATURE                 Location/Qualifiers
REGION                  1..116
```

```
                         note = Synthetic Sequence
source                   1..116
                         mol_type = protein
                         organism = synthetic construct
SEQUENCE: 119
EVKLVESGGG LVKPGGSLKL SCAASGFTFR SYGMSWVRQT PEKRLEWVAS ISSGGTTYYP  60
DSVKGRFIIS RDNARNILYL QMSSLRSEDT AMYYCAKGYD SGFAYWGQGT LVIVSA      116

SEQ ID NO: 120           moltype = AA  length = 116
FEATURE                  Location/Qualifiers
REGION                   1..116
                         note = Synthetic Sequence
source                   1..116
                         mol_type = protein
                         organism = synthetic construct
SEQUENCE: 120
QVQLKQSGPG LVQPSQSLSI TCTVSGFSLT TYGVHWVRQS PGKGLEWLGV IWRGVTTDYN  60
AAFMSRLTIT KDNSKSQVFF KMNSLQANDT AIYYCARLGF YAMDYWGQGT SVTVSS      116

SEQ ID NO: 121           moltype = AA  length = 116
FEATURE                  Location/Qualifiers
REGION                   1..116
                         note = Synthetic Sequence
source                   1..116
                         mol_type = protein
                         organism = synthetic construct
SEQUENCE: 121
QVQLKQSGPG LVQPSQSLSI TCTVSGFSLT SYGVHWVRQS PGKGLEWLGV IWSGGVTDYN  60
AAFISRLSIS KDNSKSQVFF KMNSLQANDT AIYYCARLGF YAMDYWGQGT SVTVSS      116

SEQ ID NO: 122           moltype = AA  length = 119
FEATURE                  Location/Qualifiers
REGION                   1..119
                         note = Synthetic Sequence
source                   1..119
                         mol_type = protein
                         organism = synthetic construct
SEQUENCE: 122
EVKLFESGGG LVQPGGSLKL SCVASGFDFS TYWMHWVRQA PGQGLEWIGQ INPDSTTINY  60
APSLKDRFII SRDNAKNTLF LQMSKVRSED TALYYCAKPG DYGYDFDCWG QGTTLTVSS   119

SEQ ID NO: 123           moltype = AA  length = 119
FEATURE                  Location/Qualifiers
REGION                   1..119
                         note = Synthetic Sequence
source                   1..119
                         mol_type = protein
                         organism = synthetic construct
SEQUENCE: 123
EVQLQESGPS LVKPSQTLSL TCSVTGDSIT SGYWNWIRKF PGNKLEYMGY ISYSGSTYYN  60
PSLKSRISIT RDTSKNQYYL QLNSVTTEDT ATYYCARSLL WFSTGFAYWG QGTLVTVSA   119

SEQ ID NO: 124           moltype = AA  length = 116
FEATURE                  Location/Qualifiers
REGION                   1..116
                         note = Synthetic Sequence
source                   1..116
                         mol_type = protein
                         organism = synthetic construct
SEQUENCE: 124
QVQLKQSGPG LVQPSQSLSI TCTVSGFSLT SYGVHWVRQS PGKGLEWLGV IWSGGITDYN  60
AAFKSRLSIS KDNSKSQVFF KMNSLQANDT AIYFCARLGF YAMDYWGQGT SVTVSS      116

SEQ ID NO: 125           moltype = AA  length = 116
FEATURE                  Location/Qualifiers
REGION                   1..116
                         note = Synthetic Sequence
REGION                   9..15
                         note = BRANCHED - SNTSESFK(SNTSESF)FRVTQLAPKAQIKE
source                   1..116
                         mol_type = protein
                         organism = synthetic construct
SEQUENCE: 125
EVKLVESGGG LVKPGGSLKL SCAASGFTFR SYGMSWARQI PEKRLEWVAS ISSGGTTYYL  60
GSVQGRFTIS RDNARNILYL QMSSLRSEDT AMYYCARGYD AGFAYWGQGT LVSVSE      116

SEQ ID NO: 126           moltype = AA  length = 117
FEATURE                  Location/Qualifiers
REGION                   1..117
```

```
                        note = Synthetic Sequence
source                  1..117
                        mol_type = protein
                        organism = synthetic construct
SEQUENCE: 126
EVQLQESGPS LVKPSQTLSL TCSVTGDSIT SGYWTWIRKF PGNKLEYMGY ISYTGSTYYN  60
PSLKSRISIS RDTSKSQYYL QLNSVTTEDT ATYYCARQRD WLGFAYWGQG TLVTVSA     117

SEQ ID NO: 127          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 127
EEKLVESGGG LVKPGGSLKL SCAASGFSFS SYGMSWVRQT PEKRLEWVAS ISSGGSIYYP  60
DSVKGRFTIS RDNARNILYL QMSSLRSEDT AMYYCARGYD AGFAFWGQGT LVTASA      116

SEQ ID NO: 128          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 128
QITLKESGPT LVKPTQTLTL TCTVSGFSLS TYGVHWIRQP PGKALEWLGV IWRGVTTDYN  60
AAFMSRLTIT KDNSKNQVVL TMNNMDPVDT ATYYCARLGF YAMDYWGQGT LVTVSS      116

SEQ ID NO: 129          moltype = AA  length = 116
FEATURE                 Location/Qualifiers
REGION                  1..116
                        note = Synthetic Sequence
source                  1..116
                        mol_type = protein
                        organism = synthetic construct
SEQUENCE: 129
EVQLVESGGG LVKPGGSLRL SCAASGFIFR SYGMSWVRQA PGKGLEWVAS ISSGGSTYYP  60
DSVKGRFTIS RDNAKNSLYL QMNSLRAEDT AVYDCARGYD SGFAYWGQGT LVTVSS      116

SEQ ID NO: 130          moltype = AA  length = 112
FEATURE                 Location/Qualifiers
REGION                  1..112
                        note = Synthetic Sequence
source                  1..112
                        mol_type = protein
                        organism = synthetic construct
SEQUENCE: 130
DIVLTQSPAS LAVSLGQRAT ISCRASQSVS TSSSSFMHWY QQKPGQPPKL LIKYASNLES  60
GVPARFSGSG SGTDFTLNIH PVEEEDTATY YCQHSWEIPY TFGGGTKLEI KR          112

SEQ ID NO: 131          moltype = AA  length = 111
FEATURE                 Location/Qualifiers
REGION                  1..111
                        note = Synthetic Sequence
source                  1..111
                        mol_type = protein
                        organism = synthetic construct
SEQUENCE: 131
DIVLTQSPPS LAVSLGQRAT ISCRASQSVS TSSSSYMHWY QQKPGQPPKL LIKYASNLES  60
GVPARFSGSG SGTDFTLNIH PVEEEDTATY YCQHSWEIPY TFGGGTKLEI K           111

SEQ ID NO: 132          moltype = AA  length = 107
FEATURE                 Location/Qualifiers
REGION                  1..107
                        note = Synthetic Sequence
source                  1..107
                        mol_type = protein
                        organism = synthetic construct
SEQUENCE: 132
SIVMTQTPKF LLVSAGDRVT ITCKASQSVS NDVAWYQQKP GQSPKLLIYY AANRYTGVPD  60
RFTGSGYGTD FTFTISIVQA EDLAVYFCQQ DYTSPYTFGG GTKLEIK                107

SEQ ID NO: 133          moltype = AA  length = 107
FEATURE                 Location/Qualifiers
REGION                  1..107
                        note = Synthetic Sequence
source                  1..107
```

```
                         mol_type = protein
                         organism = synthetic construct
SEQUENCE: 133
SIVMTQTPKF LLVSAGDRVT ITCKASQSVS NDVGWYQQKP GQSPKLLIYY ASNRYSGVPD  60
RFTGSGYGTD FTFTISTVQA EDLAVYFCQQ DYTSPYTFGG GTKLEIK               107

SEQ ID NO: 134           moltype = AA  length = 112
FEATURE                  Location/Qualifiers
REGION                   1..112
                         note = Synthetic Sequence
source                   1..112
                         mol_type = protein
                         organism = synthetic construct
SEQUENCE: 134
DVLMTQTPLY LPVSLGDQAS ISCRSSQIIV HSNANTYLEW FLQKPGQSPK LLIYKVSNRF  60
SGVPDRFSGS GSGTDFTLKI SRVEAEDLGV YYCFQGSHVP YTFGGGTKLE IK         112

SEQ ID NO: 135           moltype = AA  length = 108
FEATURE                  Location/Qualifiers
REGION                   1..108
                         note = Synthetic Sequence
source                   1..108
                         mol_type = protein
                         organism = synthetic construct
SEQUENCE: 135
QIVLTQSPAI MSASPGEKVT LTCSASSSVS SSYLYWNQQK PGSSPKVWIY NTSNLASGVP  60
ARFSGSGSGT SYSLTISSME AEDAASYFCH QWRSYPPTLG AGTKLELK             108

SEQ ID NO: 136           moltype = AA  length = 106
FEATURE                  Location/Qualifiers
REGION                   1..106
                         note = Synthetic Sequence
source                   1..106
                         mol_type = protein
                         organism = synthetic construct
SEQUENCE: 136
QIVLTQSPAI MSASPGEKVT MTCSANSSVS YMHWYQQKSG TSPKRWIYDT SKLASGVPAR  60
FSGSGSGTSY SLTISSMGAE DAATYYCQQW SSNPWTFGGG TKLEIK               106

SEQ ID NO: 137           moltype = AA  length = 111
FEATURE                  Location/Qualifiers
REGION                   1..111
                         note = Synthetic Sequence
source                   1..111
                         mol_type = protein
                         organism = synthetic construct
SEQUENCE: 137
DIVLTQSPAS LAVSLGQRAT ISCRASQSVS TSSYSYMHWY QQKPGQPPKL LIKYASNLES  60
GVPARFSGSG SGTDFTLNIH PVEEEDTATY YCQNSWEIPY TFGGGTKLEI K          111

SEQ ID NO: 138           moltype = AA  length = 113
FEATURE                  Location/Qualifiers
REGION                   1..113
                         note = Synthetic Sequence
source                   1..113
                         mol_type = protein
                         organism = synthetic construct
SEQUENCE: 138
DIVMTQTPSS LAVSLGEKVT MSCKSSQSLL YSSNQKNSLA WYQQKPGQSP KLLIYWASNR  60
ESGVPDRFTG SSSGTDFTLT ISSVKAEDLA VYYCQQYYSY PLTFGAGTKL ELK        113

SEQ ID NO: 139           moltype = AA  length = 111
FEATURE                  Location/Qualifiers
REGION                   1..111
                         note = Synthetic Sequence
source                   1..111
                         mol_type = protein
                         organism = synthetic construct
SEQUENCE: 139
DIVLTQSPAS LAVSLGQRAT ISCRASQSVS TSSYSYVHWY QQKPGQPPKL LIKYASNLES  60
GVPARFSGSG SGTDFTLNIH PVEEEDTATY YCQHSWEIPY TFGGGTKLEI K          111

SEQ ID NO: 140           moltype = AA  length = 107
FEATURE                  Location/Qualifiers
REGION                   1..107
                         note = Synthetic Sequence
source                   1..107
                         mol_type = protein
                         organism = synthetic construct
```

-continued

```
SEQUENCE: 140
DIQMTQSPSS LSASVGDRVT ITCKASQSVS NDVAWYQQKP GKAPKLLIYY AANRYTGVPD  60
RFSGSGYGTD FTFTISSLQP EDIATYFCQQ DYTSPYTFGQ GTKLEIK                107

SEQ ID NO: 141         moltype = AA  length = 111
FEATURE                Location/Qualifiers
REGION                 1..111
                       note = Synthetic Sequence
source                 1..111
                       mol_type = protein
                       organism = synthetic construct
SEQUENCE: 141
DIVLTQSPAS LAVSPGQRAT ITCRASQSVS TSSSSFMHWY QQKPGQPPKL LIKYASNLES  60
GVPARFSGSG SGTDFTLTIN PVEANDTANY YCQHSWEIPY TFGQGTKLEI K           111

SEQ ID NO: 142         moltype = AA  length = 117
FEATURE                Location/Qualifiers
REGION                 1..117
                       note = Synthetic Sequence
source                 1..117
                       mol_type = protein
                       organism = synthetic construct
SEQUENCE: 142
EVQLVQSGAE VKKPGESLRI SCKGSGYTFT TYWMHWVRQA TGQGLEWMGN IYPGTGGSNF  60
DEKFKNRVTI TADKSTSTAY MELSSLRSED TAVYYCTRWT TGTGAYWGQG TTVTVSS     117

SEQ ID NO: 143         moltype = AA  length = 117
FEATURE                Location/Qualifiers
REGION                 1..117
                       note = Synthetic Sequence
source                 1..117
                       mol_type = protein
                       organism = synthetic construct
SEQUENCE: 143
EVQLVQSGAE VKKPGESLRI SCKGSGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 144         moltype = AA  length = 117
FEATURE                Location/Qualifiers
REGION                 1..117
                       note = Synthetic Sequence
source                 1..117
                       mol_type = protein
                       organism = synthetic construct
SEQUENCE: 144
QVQLVQSGAE VKKPGASVKV SCKASGYTFT TYWMHWIRQS PSRGLEWLGN IYPGTGGSNF  60
DEKFKNRFTI SRDNSKNTLY LQMNSLRAED TAVYYCTRWT TGTGAYWGQG TTVTVSS     117

SEQ ID NO: 145         moltype = AA  length = 117
FEATURE                Location/Qualifiers
REGION                 1..117
                       note = Synthetic Sequence
source                 1..117
                       mol_type = protein
                       organism = synthetic construct
SEQUENCE: 145
EVQLVQSGAE VKKPGESLRI SCKGSGYTFT TYWMHWVRQA PGQGLEWMGN IYPGTGGSNF  60
DEKFKNRFTI SRDNSKNTLY LQMNSLRAED TAVYYCTRWT TGTGAYWGQG TTVTVSS     117

SEQ ID NO: 146         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 146
EIVLTQSPAT LSLSPGERAT LSCKSSQSLL DSGNQKNFLT WYQQKPGQAP RLLIYWASTR  60
ESGVPSRFSG SGSGTEFTLT ISSLQPDDFA TYYCQNDYSY PYTFGQGTKV EIK         113

SEQ ID NO: 147         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 147
DIQMTQSPSS LSASVGDRVT ITCKSSQSLL DSGNQKNFLT WYQQKPGQAP RLLIYWASTR  60
```

-continued

```
ESGIPPRFSG SGYGTDFTLT INNIESEDAA YYFCQNDYSY PYTFGQGTKV EIK         113

SEQ ID NO: 148         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 148
EIVLTQSPAT LSLSPGERAT LSCKSSQSLL DSGNQKNFLT WYQQKPGKAP KLLIYWASTR  60
ESGVPSRFSG SGSGTDFTFT ISSLQPEDIA TYYCQNDYSY PYTFGQGTKV EIK         113

SEQ ID NO: 149         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 149
DIVMTQTPLS LPVTPGEPAS ISCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 150         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 150
EIVLTQSPAT LSLSPGERAT LSCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113

SEQ ID NO: 151         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 151
EIVLTQSPDF QSVTPKEKVT ITCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 152         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 152
EIVLTQSPAT LSLSPGERAT LSCKSSQSLL DSGNQKNFLT WYQQKPGQAP RLLIYWASTR  60
ESGVPSRFSG SGSGTDFTFT ISSLEAEDAA TYYCQNDYSY PYTFGQGTKV EIK         113

SEQ ID NO: 153         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 153
DIQMTQSPSS LSASVGDRVT ITCKSSQSLL DSGNQKNFLT WYLQKPGQSP QLLIYWASTR  60
ESGVPSRFSG SGSGTDFTFT ISSLEAEDAA TYYCQNDYSY PYTFGQGTKV EIK         113

SEQ ID NO: 154         moltype = AA  length = 113
FEATURE                Location/Qualifiers
REGION                 1..113
                       note = Synthetic Sequence
source                 1..113
                       mol_type = protein
                       organism = synthetic construct
SEQUENCE: 154
DVVMTQSPLS LPVTLGQPAS ISCKSSQSLL DSGNQKNFLT WYQQKPGKAP KLLIYWASTR  60
ESGVPSRFSG SGSGTDFTFT ISSLEAEDAA TYYCQNDYSY PYTFGQGTKV EIK         113
```

-continued

```
SEQ ID NO: 155          moltype = AA  length = 118
FEATURE                 Location/Qualifiers
REGION                  1..118
                        note = Synthetic Sequence
source                  1..118
                        mol_type = protein
                        organism = synthetic construct
SEQUENCE: 155
EVQLVESGGG LVQPGGSLRL SCAASGFTFS DSWIHWVRQA PGKGLEWVAW ISPYGGSTYY  60
ADSVKGRFTI SADTSKNTAY LQMNSLRAED TAVYYCARRH WPGGFDYWGQ GTLVTVSA    118

SEQ ID NO: 156          moltype = AA  length = 108
FEATURE                 Location/Qualifiers
REGION                  1..108
                        note = Synthetic Sequence
source                  1..108
                        mol_type = protein
                        organism = synthetic construct
SEQUENCE: 156
DIQMTQSPSS LSASVGDRVT ITCRASQDVS TAVAWYQQKP GKAPKLLIYS ASFLYSGVPS  60
RFSGSGSGTD FTLTISSLQP EDFATYYCQQ YLYHPATFGQ GTKVEIKR               108

SEQ ID NO: 157          moltype = AA  length = 126
FEATURE                 Location/Qualifiers
REGION                  1..126
                        note = Synthetic Sequence
source                  1..126
                        mol_type = protein
                        organism = synthetic construct
SEQUENCE: 157
EVQLVESGGG LVQPGGSLRL SCAASGFTLD YYAIGWFRQA PGKEREWASS ISSSDGSTYY  60
ADSVKGRFTI SRDNAKNTVF LQMNSLKPED TAVYSCAASQ APITIATMMK PFYDYWGQGT  120
QVTVSS                                                             126

SEQ ID NO: 158          moltype = AA  length = 123
FEATURE                 Location/Qualifiers
REGION                  1..123
                        note = Synthetic Sequence
source                  1..123
                        mol_type = protein
                        organism = synthetic construct
SEQUENCE: 158
EVQLVESGGG LVQPGGSLRL SCAASGFTLD YYAKCWFRQA PGKEREWVSC ISSSDGSTYY  60
ADSVKGRFTI SRDNAKNTVY LQMNSLKPED TAVYFCAARH GGPLTVEYFF DYWGQGTQVT  120
VSS                                                                123

SEQ ID NO: 159          moltype = AA  length = 124
FEATURE                 Location/Qualifiers
REGION                  1..124
                        note = Synthetic Sequence
source                  1..124
                        mol_type = protein
                        organism = synthetic construct
SEQUENCE: 159
EVQLVESGGG LVQPGGSLRL SCAASGFTFD YYAIGWFRQA PGKAREGVSC ISGGDNSTYY  60
ADSVKGRFTI SRDNAKNTVY LQMNSLKPED TAVYYCATGG WKYCSGYDPE YIYWGQGTQV  120
TVSS                                                               124

SEQ ID NO: 160          moltype = AA  length = 115
FEATURE                 Location/Qualifiers
REGION                  1..115
                        note = Synthetic Sequence
source                  1..115
                        mol_type = protein
                        organism = synthetic construct
SEQUENCE: 160
EVQLVESGGG LVQAGGSLRL SCAASGSTFS QYDVGWYRQA PGKQRELVAF SSSGGRTIYP  60
DSVKGRFTFS RDNTKNTVYL QMTSLKPEDT AVYYCKIDWY LNSYWGQGTQ VTVSS       115

SEQ ID NO: 161          moltype = AA  length = 114
FEATURE                 Location/Qualifiers
REGION                  1..114
                        note = Synthetic Sequence
source                  1..114
                        mol_type = protein
                        organism = synthetic construct
SEQUENCE: 161
EVQLVESGGG LVQAGGSLRL SCAASGVDAS NSAMGWYRQA PGKQREWVAR ITGGGLIAYT  60
DSVKGRFTIS RDNAKSTVYL QMNSLEPEDT AVYYCNTINS RDGWGQGTQV TVSS        114
```

```
SEQ ID NO: 162         moltype = AA  length = 111
FEATURE                Location/Qualifiers
REGION                 1..111
                       note = Synthetic Sequence
source                 1..111
                       mol_type = protein
                       organism = synthetic construct
SEQUENCE: 162
EVQLVESGGG LVQAGGSLTI SCAASGITFS DSIVSWYRRA RGKQREWVAG ISNGGTTKYA  60
ESVLGRFTIS RDNAKNNVYL QMNGLNPEDT AVYLCKVRQY WGQGTQVTVS S           111

SEQ ID NO: 163         moltype = AA  length = 130
FEATURE                Location/Qualifiers
REGION                 1..130
                       note = Synthetic Sequence
source                 1..130
                       mol_type = protein
                       organism = synthetic construct
SEQUENCE: 163
EVQLVESGGG LVQAGGSLRL SCAASESTVL INAMGWYRQA PGKQRELVAS ISSGGSTNYA  60
DSVKGRFTIS RDNAKNTVYL QMNSLKPEDT AVYYCNADVY PQDYGLGYVE GKVYYGHDYW  120
GTGTLVTVSS                                                         130

SEQ ID NO: 164         moltype = AA  length = 119
FEATURE                Location/Qualifiers
REGION                 1..119
                       note = Synthetic Sequence
source                 1..119
                       mol_type = protein
                       organism = synthetic construct
SEQUENCE: 164
EVQLVESGGG LVQAGGSLRL SCAASGSTFS NYVSNYAMGW GRQAPGTQRE LVASISNGDT  60
TNYADSVKGR FTISRDNAKN TVYLQMNSLK PEDTAVYYCF EHQVAGLTWG QGTQVTVSS   119

SEQ ID NO: 165         moltype = AA  length = 118
FEATURE                Location/Qualifiers
REGION                 1..118
                       note = Synthetic Sequence
SITE                   27
                       note = misc_feature - Xaa can be any naturally occurring
                        amino acid
SITE                   32
                       note = misc_feature - Xaa can be any naturally occurring
                        amino acid
SITE                   75
                       note = misc_feature - Xaa can be any naturally occurring
                        amino acid
source                 1..118
                       mol_type = protein
                       organism = synthetic construct
SEQUENCE: 165
EVQLVESGGG LVQAGGSLRL SCVASGXALK IXVMGWYRQA PGKQRELVAA ITSGGRTNYS  60
DSVKGRFTIS GDNAXNTVYL QMNSLKSEDT AVYYCREWNS GYPPVDYWGQ GTQVTVSS    118

SEQ ID NO: 166         moltype = AA  length = 120
FEATURE                Location/Qualifiers
REGION                 1..120
                       note = Synthetic Sequence
source                 1..120
                       mol_type = protein
                       organism = synthetic construct
SEQUENCE: 166
EVQLVESGGG LVQAGGSLRL SCAASGRTFS SGTMGWFRRA PGKEREFVAS IPWSGGRTYY  60
ADSVKDRFTI SRDNAQNTVF LQMNSLKPED TAVYYCAFKE RSTGWDFASW GQGIQVTVSS  120

SEQ ID NO: 167         moltype = AA  length = 127
FEATURE                Location/Qualifiers
REGION                 1..127
                       note = Synthetic Sequence
source                 1..127
                       mol_type = protein
                       organism = synthetic construct
SEQUENCE: 167
EVQLVESGGG LVQTGGSLRL SCAASGFTLD YYGIGWFRQA PGKEREGVSF ISGSDGSTYY  60
AESVKGRFTI SRDKAKNTVY LQMNSLKPED TAVYYCAADP WGPPSIATMT SYEYKHWGQG  120
TQVTVSS                                                            127

SEQ ID NO: 168         moltype = AA  length = 113
```

```
FEATURE                Location/Qualifiers
REGION                 1..113
                       note = Synthetic Sequence
source                 1..113
                       mol_type = protein
                       organism = synthetic construct
SEQUENCE: 168
EVQLVESGGG LVQPGGSLRL SCAASGFTFS TYTMIWLRRA PGKGFEWVST IDKDGNTNYV  60
DSVKGRFAVS RDNTKNTLYL QMNSLKPEDT AMYYCTKHGS SARGQGTRVT VSS         113

SEQ ID NO: 169         moltype = AA  length = 114
FEATURE                Location/Qualifiers
REGION                 1..114
                       note = Synthetic Sequence
source                 1..114
                       mol_type = protein
                       organism = synthetic construct
SEQUENCE: 169
EVQLVESGGG LVEPGGSLRL SCVASGFTFS SYDMSWVRQA PGKGLEWVST INSGGGITYR  60
GSVKGRFTIS RDNAKNTLYL QMNSLKPEDT AVYYCENGGS SYRRGQGTQV TVSS        114

SEQ ID NO: 170         moltype = AA  length = 114
FEATURE                Location/Qualifiers
REGION                 1..114
                       note = Synthetic Sequence
source                 1..114
                       mol_type = protein
                       organism = synthetic construct
SEQUENCE: 170
QVQLVQSGAE LKKPGASVKM SCKASGYTFT GYTMHWVKQA PGQGLEWIGY INPRSGYTEY  60
NQKFKDRTTL TADKSTSTAY MELSSLRSED SAVYYCARPW FAYWGQGTLV TVSS        114

SEQ ID NO: 171         moltype = AA  length = 114
FEATURE                Location/Qualifiers
REGION                 1..114
                       note = Synthetic Sequence
source                 1..114
                       mol_type = protein
                       organism = synthetic construct
SEQUENCE: 171
QVQLVQSGAE VKKPGASVKM SCKASGYTFT GYTMHWVKQA PGQGLEWIGY INPRSGYTEY  60
NQKFKDRTTL TADKSTSTAY MELSSLRSED TAVYYCARPW FAYWGQGTLV TVSS        114

SEQ ID NO: 172         moltype = AA  length = 114
FEATURE                Location/Qualifiers
REGION                 1..114
                       note = Synthetic Sequence
source                 1..114
                       mol_type = protein
                       organism = synthetic construct
SEQUENCE: 172
QVQLVQSGAE VKKPGASVKM SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 173         moltype = AA  length = 114
FEATURE                Location/Qualifiers
REGION                 1..114
                       note = Synthetic Sequence
source                 1..114
                       mol_type = protein
                       organism = synthetic construct
SEQUENCE: 173
QVQLVQSGAE VKKPGASVKV SCKASGYTFT GYTMHWVRQA PGQGLEWIGY INPRSGYTEY  60
NQKFKDRTTL TADKSTSTAY MELSSLRSED TAVYYCARPW FAYWGQGTLV TVSS        114

SEQ ID NO: 174         moltype = AA  length = 114
FEATURE                Location/Qualifiers
REGION                 1..114
                       note = Synthetic Sequence
source                 1..114
                       mol_type = protein
                       organism = synthetic construct
SEQUENCE: 174
QVQLVQSGAE VKKPGASVKV SCKASGYTFT GYTMHWVRQA PGQGLEWIGY INPRSGYTEY  60
NQKFKDRTTI TADKSTSTAY MELSSLRSED TAVYYCARPW FAYWGQGTLV TVSS        114

SEQ ID NO: 175         moltype = AA  length = 113
FEATURE                Location/Qualifiers
REGION                 1..113
```

```
                         note = Synthetic Sequence
source                   1..113
                         mol_type = protein
                         organism = synthetic construct
SEQUENCE: 175
DIVMTQSPAS LTVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 176           moltype = AA  length = 113
FEATURE                  Location/Qualifiers
REGION                   1..113
                         note = Synthetic Sequence
source                   1..113
                         mol_type = protein
                         organism = synthetic construct
SEQUENCE: 176
DIVMTQSPAS LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 177           moltype = AA  length = 113
FEATURE                  Location/Qualifiers
REGION                   1..113
                         note = Synthetic Sequence
source                   1..113
                         mol_type = protein
                         organism = synthetic construct
SEQUENCE: 177
DIVMTQSPAF LSVTPGEKVT ITCKSSQSLL NSGNQKNYLT WYQQKPGQPP KLLIYWASTR  60
ESGVPDRFTG SGSGTDFTLT ISSLQAEDVA VYYCQNDYSY PLTFGQGTKL EIK         113

SEQ ID NO: 178           moltype = AA  length = 113
FEATURE                  Location/Qualifiers
REGION                   1..113
                         note = Synthetic Sequence
source                   1..113
                         mol_type = protein
                         organism = synthetic construct
SEQUENCE: 178
DIVMTQSPAF LSVTPGEKVT ITCKSSQSLL NSGNQKNYLT WYQQKPGQPP KLLIYWASTR  60
ESGVPDRFSG SGSGTDFTLT ISSLQAEDVA VYYCQNDYSY PLTFGQGTKL EIK         113

SEQ ID NO: 179           moltype = AA  length = 165
FEATURE                  Location/Qualifiers
REGION                   1..165
                         note = Synthetic Sequence
source                   1..165
                         mol_type = protein
                         organism = synthetic construct
SEQUENCE: 179
CDLPQTHSLG SRRTLMLLAQ MRKISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 180           moltype = AA  length = 165
FEATURE                  Location/Qualifiers
REGION                   1..165
                         note = Synthetic Sequence
source                   1..165
                         mol_type = protein
                         organism = synthetic construct
SEQUENCE: 180
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 181           moltype = AA  length = 157
FEATURE                  Location/Qualifiers
REGION                   1..157
                         note = Synthetic Sequence
source                   1..157
                         mol_type = protein
                         organism = synthetic construct
SEQUENCE: 181
VRSSSRTPSD KPVAHVVANP QAEGQLQWLN RRANALLANG VELRDNQLVV PSEGLYLIYS  60
QVLFKGQGCP STHVLLTHTI SRIAVSYQTK VNLLSAIKSP CQRETPEGAE AKPWYEPIYL  120
GGVFQLEKGD RLSAEINRPD YLDFAESGQV YFGIIAL                           157

SEQ ID NO: 182           moltype = AA  length = 171
FEATURE                  Location/Qualifiers
```

-continued

```
REGION                1..171
                      note = Synthetic Sequence
source                1..171
                      mol_type = protein
                      organism = synthetic construct
SEQUENCE: 182
LPGVGLTPSA AQTARQHPKM HLAHSNLKPA AHLIGDPSKQ NSLLWRANTD RAFLQDGFSL  60
SNNSLLVPTS GIYFVYSQVV FSGKAYSPKA TSSPLYLAHE VQLFSSQYPF HVPLLSSQKM  120
VYPGLQEPWL HSMYHGAAFQ LTQGDQLSTH TDGIPHLVLS PSTVFFGAFA L           171

SEQ ID NO: 183        moltype = AA  length = 153
FEATURE               Location/Qualifiers
REGION                1..153
                      note = Synthetic Sequence
source                1..153
                      mol_type = protein
                      organism = synthetic construct
SEQUENCE: 183
APVRSLNCTL RDSQQKSLVM SGPYELKALH LQGQDMEQQV VFSMSFVQGE ESNDKIPVAL  60
GLKEKNLYLS CVLKDDKPTL QLESVDPKNY PKKKMEKRFV FNKIEINNKL EFESAQFPNW  120
YISTSQAENM PVFLGGTKGG QDITDFTMQF VSS                               153

SEQ ID NO: 184        moltype = AA  length = 133
FEATURE               Location/Qualifiers
REGION                1..133
                      note = Synthetic Sequence
source                1..133
                      mol_type = protein
                      organism = synthetic construct
SEQUENCE: 184
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 185        moltype = AA  length = 129
FEATURE               Location/Qualifiers
REGION                1..129
                      note = Synthetic Sequence
source                1..129
                      mol_type = protein
                      organism = synthetic construct
SEQUENCE: 185
HKCDITLQEI IKTLNSLTEQ KTLCTELTVT DIFAASKNTT EKETFCRAAT VLRQFYSHHE  60
KDTRCLGATA QQFHRHKQLI RFLKRLDRNL WGLAGLNSCP VKEANQSTLE NFLERLKTIM  120
REKYSKCSS                                                          129

SEQ ID NO: 186        moltype = AA  length = 185
FEATURE               Location/Qualifiers
REGION                1..185
                      note = Synthetic Sequence
source                1..185
                      mol_type = protein
                      organism = synthetic construct
SEQUENCE: 186
APVPPGEDSK DVAAPHRQPL TSSERIDKQI RYILDGISAL RKETCNKSNM CESSKEALAE  60
NNLNLPKMAE KDGCFQSGFN EETCLVKIIT GLLEFEVYLE YLQNRFESSE EQARAVQMST  120
KVLIQFLQKK AKNLDAITTP DPTTNASLTT KLQAQNQWLQ DMTTHLILRS FKEFLQSSLR  180
ALRQM                                                              185

SEQ ID NO: 187        moltype = AA  length = 114
FEATURE               Location/Qualifiers
REGION                1..114
                      note = Synthetic Sequence
source                1..114
                      mol_type = protein
                      organism = synthetic construct
SEQUENCE: 187
SPGPVPPSTA LRELIEELVN ITQNQKAPLC NGSMVWSINL TAGMYCAALE SLINVSGCSA  60
IEKTQRMLSG FCPHKVSAGQ FSSLHVRDTK IEVAQFVKDL LLHLKKLFRE GRFN        114

SEQ ID NO: 188        moltype = AA  length = 194
FEATURE               Location/Qualifiers
REGION                1..194
                      note = Synthetic Sequence
source                1..194
                      mol_type = protein
                      organism = synthetic construct
SEQUENCE: 188
MAAEPVEDNC INFVAMKFID NTLYFIAEDD ENLESDYFGK LESKLSVIRN LNDQVLFIDQ  60
```

-continued

```
GNRPLFEDMT DSDCRDNAPR TIFIISMYKD SQPRGMAVTI SVKCEKISTL SCENKIISFK  120
EMNPPDNIKD TKSDIIFFQR SVPGHDNKMQ FESSSYEGYF LACEKERDLF KLILKKEDEL  180
GDRSIMFTVQ NEDL                                                    194

SEQ ID NO: 189          moltype = AA  length = 270
FEATURE                 Location/Qualifiers
REGION                  1..270
                        note = Synthetic Sequence
source                  1..270
                        mol_type = protein
                        organism = synthetic construct
SEQUENCE: 189
MKPKMKYSTN KISTAKWKNT ASKALCFKLG KSQQKAKEVC PMYFMKLRSG LMIKKEACYF  60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
GVKDNHLALI KVDSSENLCT ENILFKLSET                                   270

SEQ ID NO: 190          moltype = AA  length = 16
FEATURE                 Location/Qualifiers
REGION                  1..16
                        note = Synthetic Sequence
source                  1..16
                        mol_type = protein
                        organism = synthetic construct
SEQUENCE: 190
GGSGGSGGGG SGGGGS                                                  16

SEQ ID NO: 191          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 191
GGGGS                                                              5

SEQ ID NO: 192          moltype = AA  length = 20
FEATURE                 Location/Qualifiers
REGION                  1..20
                        note = Synthetic Sequence
REPEAT                  1..5
                        note = (GGGGS)n (n=1-4)
source                  1..20
                        mol_type = protein
                        organism = synthetic construct
SEQUENCE: 192
GGGGSGGGGS GGGGSGGGGS                                              20

SEQ ID NO: 193          moltype = AA  length = 24
FEATURE                 Location/Qualifiers
REGION                  1..24
                        note = Synthetic Sequence
source                  1..24
                        mol_type = protein
                        organism = synthetic construct
SEQUENCE: 193
GLYGLYGLYG LYGLYGLYGL YGLY                                         24

SEQ ID NO: 194          moltype = AA  length = 18
FEATURE                 Location/Qualifiers
REGION                  1..18
                        note = Synthetic Sequence
source                  1..18
                        mol_type = protein
                        organism = synthetic construct
SEQUENCE: 194
GLYGLYGLYG LYGLYGLY                                                18

SEQ ID NO: 195          moltype = AA  length = 15
FEATURE                 Location/Qualifiers
REGION                  1..15
                        note = Synthetic Sequence
REPEAT                  1..5
                        note = (EAAAK)n (n=1-3)
source                  1..15
                        mol_type = protein
                        organism = synthetic construct
```

```
SEQUENCE: 195
EAAAKEAAAK EAAAK                                                  15

SEQ ID NO: 196          moltype = AA  length = 28
FEATURE                 Location/Qualifiers
REGION                  1..28
                        note = Synthetic Sequence
REPEAT                  2..6
                        note = A(EAAAK)nA (n = 2-5)
source                  1..28
                        mol_type = protein
                        organism = synthetic construct
SEQUENCE: 196
AEAAAKEAAA KEAAAKEAAA KEAAAKNA                                    28

SEQ ID NO: 197          moltype = AA  length = 12
FEATURE                 Location/Qualifiers
REGION                  1..12
                        note = Synthetic Sequence
source                  1..12
                        mol_type = protein
                        organism = synthetic construct
SEQUENCE: 197
AEAAAKEAAA KA                                                     12

SEQ ID NO: 198          moltype = AA  length = 46
FEATURE                 Location/Qualifiers
REGION                  1..46
                        note = Synthetic Sequence
source                  1..46
                        mol_type = protein
                        organism = synthetic construct
SEQUENCE: 198
AEAAAKEAAA KEAAAKEAAA KALEAEAAAK EAAAKEAAAK EAAAKA                46

SEQ ID NO: 199          moltype = AA  length = 5
FEATURE                 Location/Qualifiers
REGION                  1..5
                        note = Synthetic Sequence
source                  1..5
                        mol_type = protein
                        organism = synthetic construct
SEQUENCE: 199
PAPAP                                                             5

SEQ ID NO: 200          moltype = AA  length = 18
FEATURE                 Location/Qualifiers
REGION                  1..18
                        note = Synthetic Sequence
source                  1..18
                        mol_type = protein
                        organism = synthetic construct
SEQUENCE: 200
KESGSVSSEQ LAQFRSLD                                               18

SEQ ID NO: 201          moltype = AA  length = 14
FEATURE                 Location/Qualifiers
REGION                  1..14
                        note = Synthetic Sequence
source                  1..14
                        mol_type = protein
                        organism = synthetic construct
SEQUENCE: 201
EGKSSGSGSE SKST                                                   14

SEQ ID NO: 202          moltype = AA  length = 12
FEATURE                 Location/Qualifiers
REGION                  1..12
                        note = Synthetic Sequence
source                  1..12
                        mol_type = protein
                        organism = synthetic construct
SEQUENCE: 202
GSAGSAAGSG EF                                                     12
```

METHODS OF CANCER TREATMENT WITH PD-L1 TARGETED INTERFERON THERAPEUTIC AGENTS

CROSS-REFERENCE TO RELATED APPLICATIONS

This application is a continuation of U.S. application Ser. No. 16/075,323, filed Aug. 3, 2018 (now U.S. Pat. No. 11,661,455), which is a National Stage Entry of PCT/EP2017/052545, filed Feb. 6, 2017, which claims the benefit of U.S. Provisional Patent Application Nos. 62/291,769, filed Feb. 5, 2016; 62/335,880, filed May 13, 2016; 62/411,805, filed Oct. 24, 2016; 62/291,772, filed Feb. 5, 2016; 62/291,774, filed Feb. 5, 2016; 62/335,965, filed May 13, 2016; 62/291,776, filed Feb. 5, 2016; 62/335,968, filed May 13, 2016; 62/335,979, filed May 13, 2016; 62/336,030, filed May 13, 2016, 62/353,607, filed Jun. 23, 2016; and 62/291,779, filed Feb. 5, 2016, the entire contents of all of which are herein incorporated by reference.

FIELD

The present invention relates, in part, to targeted therapeutic agents and their use in the treatment of diseases such as cancer.

SEQUENCE LISTING

This application contains a Sequence Listing in XML format submitted electronically herewith via Patent Center. The contents of the XML copy, created on Aug. 29, 2023, is named "ORN-021C1_114384-5021.xml" and is 278,832 bytes in size. The Sequence Listing is incorporated herein by reference in its entirety.

BACKGROUND

In contrast to conventional cancer therapies such as chemotherapy and radiation, immunotherapies provide the advantage of cell specificity against cancer cells. Specifically, immunotherapies directly target cancer cells by inducing, enhancing, or suppressing a patient's own immune response. As such, methods for enhancing the efficacy of immune-based therapies can be clinically beneficial. However, despite impressive patient responses to agents targeting the immune costimulatory and coinhibitory molecules, including, for example, clinical trials that led to the approval of YERVOY, KEYTRUDA, and OPDIVO, immunotherapies such as checkpoint inhibition therapy still fails in the overwhelming majority of patients. Further still, many immunotherapies are complicated by side effects that significantly narrows a patient's therapeutic window for treatment and makes the patient more susceptible to other diseases.

Accordingly, there remains a need for improved immunotherapeutic agents that can provide targeted therapy against cancers while causing minimal side effects.

SUMMARY

In some aspects, the present invention relates to chimeric proteins having one targeting moiety which has a recognition domain (e.g. antigen recognition domains, including without limitation, various antibody formats, inclusive of single-domain antibodies) which specifically bind to a target (e.g. antigen, receptor) of interest. In various embodiments, the targeting moiety has a recognition domain that bind to a checkpoint protein selected from programmed cell death protein 1 (PD-1), PD-1 ligand 1 (PD-L1; also known as B7-H1 and CD274), and PD-1 ligand 2 (PD-L2; also known as B7-DC and CD273).

In various embodiments, the chimeric protein further comprises a modified (e.g. mutant) signaling agent (for instance, an immune-modulating agent). In various embodiments, the modified (e.g. mutant) signaling agent has one or more modifications (e.g. mutations) that provide improved safety as compared to an unmodified (e.g. wild type) signaling agent. In various embodiments, the modified signaling agent is selected from one or more of an interleukin, interferon, and tumor necrosis factor. In an embodiment, the modified signaling agent is human interferon-α2. In another embodiment, the modified signaling agent is human TNF-α. In a further embodiment, the modified signaling agent is human IL-13.

In some embodiments, the targeting moiety and the modified (e.g. mutant) signaling agent are connected by one or more linkers.

In various embodiments, the present chimeric proteins find use in the treatment of various diseases or disorders such as cancer, infections, immune disorders, and autoimmune diseases, and the present invention encompasses various methods of treatment.

DETAILED DESCRIPTION

Figure 1:
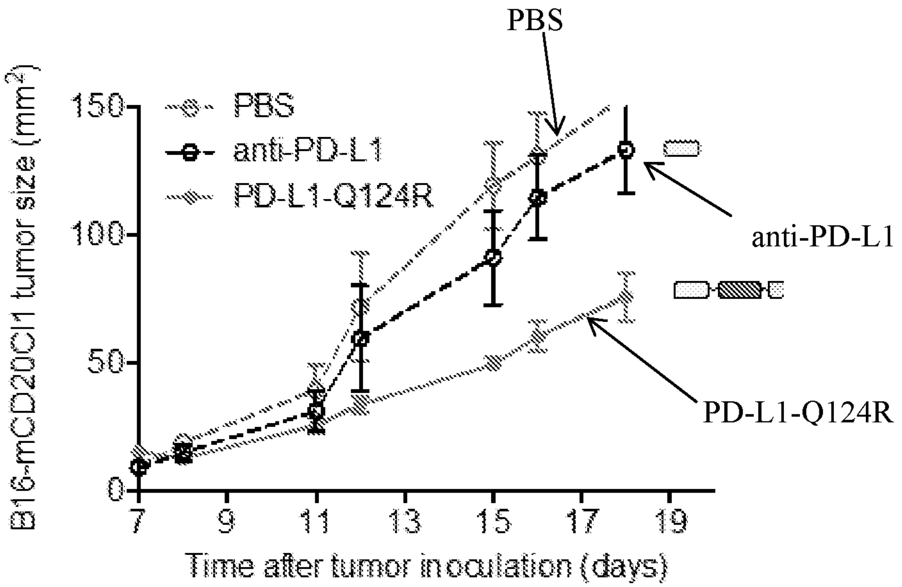
FIG. 1 shows C57BL/6 mice were inoculated subcutaneously (50 μl) with $6\times10^5$ B16mCD20c11 melanoma tumor cells. Perilesional treatment with 120 μg of an anti-PD-L1 VHH (120 μl) or a fusion of an anti-PD-L1 VHH to human IFNalpha, Q124R mutant was started when tumors reached a size of ±10 mm 2 as measured by caliper. The curves are in the same order (top to bottom) as in the figure legend identifying the treatment types (e.g. PBS is the top curve, anti-PD-L1 is the middle curve, and the bottom curve is the fusion of an anti-PD-L1 VHH to human IFNalpha, Q124R mutant).
Figure 1:
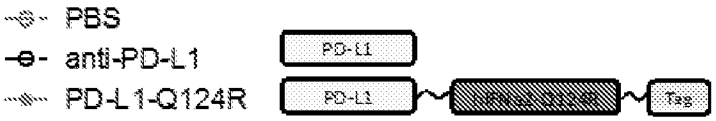

The present invention provides chimeric proteins with a signaling agent bearing therapeutically beneficial mutations and a targeting moiety that targets the signaling agent to sites in need of therapeutic action (e.g. a tumor cell) or that are appropriate for therapeutic action (e.g. an immune cell). The present invention provides pharmaceutical compositions comprising the chimeric proteins and their use in the treatment of various diseases. Administration of the chimeric proteins and pharmaceutical compositions of the invention achieves significantly reduced side effects compared to the wild type signaling agent.

Targeting Moieties

In various embodiments, the present chimeric protein has one targeting moiety directed against an immune checkpoint protein. In various embodiments, the immune checkpoint protein is selected from programmed cell death protein 1 (PD-1), PD-1 ligand 1 (PD-L1; also known as B7-H1 and CD274), and PD-1 ligand 2 (PD-L2; also known as B7-DC and CD273).

In various embodiments, the targeting moiety of the present chimeric protein is a protein-based agent capable of specific binding, such as an antibody or derivatives thereof. In an embodiment, the targeting moiety comprises an antibody. In various embodiments, the antibody is a full-length multimeric protein that includes two heavy chains and two light chains. Each heavy chain includes one variable region (e.g., $V_H$) and at least three constant regions (e.g., $CH_1$, $CH_2$ and $CH_3$), and each light chain includes one variable region ($V_L$) and one constant region ($C_L$). The variable regions determine the specificity of the antibody. Each variable region comprises three hypervariable regions also known as complementarity determining regions (CDRs) flanked by four relatively conserved framework regions (FRs). The three CDRs, referred to as CDR1, CDR2, and CDR3, contribute to the antibody binding specificity. In some embodiments, the antibody is a chimeric antibody. In some embodiments, the antibody is a humanized antibody.

In some embodiments, the targeting moiety comprises antibody derivatives or formats. In some embodiments, the targeting moiety of the present chimeric protein is a single-domain antibody, a recombinant heavy-chain-only antibody (VHH), a single-chain antibody (scFv), a shark heavy-chain-only antibody (VNAR), a microprotein (cysteine knot protein, knottin), a DARPin; a Tetranectin; an Affibody; a Transbody; an Anticalin; an AdNectin; an Affilin; a Microbody; a peptide aptamer; an alterase; a plastic antibody; a phylomer; a stradobody; a maxibody; an evibody; a fynomer, an armadillo repeat protein, a Kunitz domain, an avimer, an atrimer, a probody, an immunobody, a triomab, a troybody; a pepbody; a vaccibody, a UniBody; Affimers, a DuoBody, a Fv, a Fab, a Fab', a $F(ab')_2$, a peptide mimetic molecule, or a synthetic molecule, as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

In one embodiment, the targeting moiety comprises a single-domain antibody, such as VHH from, for example, an organism that produces VHH antibody such as a camelid, a shark, or a designed VHH. VHHs are antibody-derived therapeutic proteins that contain the unique structural and functional properties of naturally-occurring heavy-chain antibodies. VHH technology is based on fully functional antibodies from camelids that lack light chains. These heavy-chain antibodies contain a single variable domain (VHH) and two constant domains (CH2 and CH3). VHHs are commercially available under the trademark of NANOBODIES.

In various embodiments, the present chimeric protein has one targeting moiety directed against PD-1. PD-1 is expressed on a large proportion of tumor-infiltrating lymphocytes from many different tumor types. For example, PD-1 is highly expressed on CD4+ and CD8+ T cells. PD-1 is also expressed on other activated non-T lymphocytes, including B cells and natural killer (NK) cells. In some embodiments, the chimeric protein comprises a targeting moiety directed against PD-1 and a modified IFN-α comprising one or more mutations as described herein (e.g. the human IFN-α2 mutation described herein). In some embodiments, the chimeric protein comprises: a targeting moiety directed against PD-1 and a modified TNF-α comprising one or more mutations as described herein. In some embodiments, the chimeric protein comprises: a targeting moiety directed against PD-1 and a modified IL-1β comprising one or more mutations as described herein.

In various embodiments, the present chimeric protein has a targeting moiety directed against PD-1. In some embodiments, the chimeric protein has a targeting moiety which selectively bind a PD-1 polypeptide. In some embodiments, the chimeric protein comprises an antibody, an antibody derivative or format, a peptide or polypeptide, or a fusion protein that selectively binds a PD-1 polypeptide.

In an embodiment, the targeting moiety comprises the anti-PD-1 antibody pembrolizumab (aka MK-3475, KEYTRUDA), or fragments thereof. Pembrolizumab and other humanized anti-PD-1 antibodies are disclosed in Hamid, et al. (2013) New England Journal of Medicine 369 (2): 134-44, U.S. Pat. No. 8,354,509, and WO 2009/114335, the entire disclosures of which are hereby incorporated by reference. In illustrative embodiments, pembrolizumab or an antigen-binding fragment thereof for use in the methods provided herein comprises a heavy chain comprising the amino acid sequence of:

(SEQ ID NO: 1)
QVQLVQSGVEVKKPGASVKVSCKASGYTFTNYYMYWVRQAPGQGLEWMGGI

NPSNGGTNFNEKFKNRVTLTTDSSTTTAYMELKSLQFDDTAVYYCARRDYR

FDMGFDYWGQGTTVTVSSASTKGPSVFPLAPCSRSTSESTAALGCLVKDYF

PEPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMISR

TPEVTCVVVDVSQEDPEVQFNWYVDGVEVHNAKTKPREEQFNSTYRVVSVL

TVLHQDWLNGKEYKCKVSNKGLPSSIEKTISKAKGQPREPQVYTLPPSQEE

-continued

MTKNQVSLTCLVKGFYPSDIAVEWESNGQPENNYKTTPPVLDSDGSFFLYS

RLTVDKSRWQEGNVFSCSVMHEALHNHYTQKSLSLSLGK;

and/or a light chain comprising the amino acid sequence of:

(SEQ ID NO: 2)
EIVLTQSPATLSLSPGERATLSCRASKGVSTSGYSYLHWYQQKPGQAPRLL

IYLASYLESGVPARFSGSGSGTDFTLTISSLEPEDFAVYYCQHSRDLPLTF

GGGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQG

LSSPVTKSFNRGEC.

In an embodiment, the targeting moiety comprises the anti-PD-1 antibody, nivolumab (aka BMS-936558, MDX-1106, ONO-4538, OPDIVO), or fragments thereof. Nivolumab (clone 5C4) and other human monoclonal antibodies that specifically bind to PD-1 are disclosed in U.S. Pat. No. 8,008,449 and WO 2006/121168, the entire disclosures of which are hereby incorporated by reference. In illustrative embodiments, nivolumab or an antigen-binding fragment thereof comprises a heavy chain comprising the amino acid sequence of:

(SEQ ID NO: 3)
QVQLVESGGG VVQPGRSLRL DCKASGITFS NSGMHWVRQA

PGKGLEWVAV IWYDGSKRYY ADSVKGRFTI SRDNSKNTLF

LQMNSLRAED TAVYYCATND DYWGQGTLVT VSSASTKGPS

VFPLAPCSRS TSESTAALGC LVKDYFPEPV TVSWNSGALT

SGVHTFPAVL QSSGLYSLSS VVTVPSSSLG TKTYTCNVDH

KPSNTKVDKR VESKYGPPCP PCPAPEFLGG PSVFLFPPKP

KDTLMISRTP EVTCVVVDVS QEDPEVQFNW YVDGVEVHNA

KTKPREEQFN STYRVVSVLT VLHQDWLNGK EYKCKVSNKG

LPSSIEKTIS KAKGQPREPQ VYTLPPSQEE MTKNQVSLTC

LVKGFYPSDI AVEWESNGQP ENNYKTTPPV LDSDGSFFLY

SRLTVDKSRW QEGNVFSCSV MHEALHNHYT QKSLSLSLGK;

and/or a light chain comprising the amino acid sequence of:

(SEQ ID NO: 4)
EIVLTQSPAT LSLSPGERAT LSCRASQSVS SYLAWYQQKP

GQAPRLLIYD ASNRATGIPA RFSGSGSGTD FTLTISSLEP

EDFAVYYCQQ SSNWPRTFGQ GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.

In an embodiment, the targeting moiety comprises the anti-PD-1 antibody pidilizumab (aka CT-011, hBAT or hBAT-1), or fragments thereof. Pidilizumab and other humanized anti-PD-I monoclonal antibodies are disclosed in US 2008/0025980 and WO 2009/101611, the entire disclosures of which are hereby incorporated by reference. In illustrative embodiments, the anti-PD-1 antibody or an antigen-binding fragment thereof for use in the methods provided herein comprises a light chain variable regions comprising an amino acid sequence selected from SEQ ID NOS: 15-18 of US 2008/0025980:

SEQ ID No: 15 of US 2008/0025980 (SEQ ID NO: 5):
EIVLTQSPSSLSASVGDRVTITCSARSSVSYMHWYQQKPGKAPKLLIYRTS

NLASGVPSRFSGSGSGTDFTLTINSLQPEDFATYYCQQRSSFPLTFGGGTK

LEIK;

SEQ ID No: 16 of US 2008/0025980 (SEQ ID NO: 6):
EIVLTQSPSSLSASVGDRVTITCSARSSVSYMHWFQQKPGKAPKLWIYRTS

NLASGVPSRFSGSGSGTDYTLTINSLQPEDFATYYCQQRSSFPLTFGGGTK

LEIK;

SEQ ID No: 17 of US 2008/0025980 (SEQ ID NO: 7):
EIVLTQSPSSLSASVGDRVTITCSARSSVSYMHWFQQKPGKAPKLWIYRTS

NLASGVPSRFSGSGSGTDYCLTINSLQPEDFATYYCQQRSSFPLTFGGGTK

LEIK;

SEQ ID No: 18 of US 2008/0025980 (SEQ ID NO: 8):
EIVLTQSPSSLSASVGDRVTITCSARSSVSYMHWFQQKPGKAPKLWIYRTS

NLASGVPSRFSGSGSGTSYCLTINSLQPEDFATYYCQQRSSFPLTFGGGTK

LEIK;

and/or a heavy chain comprising an amino acid sequence selected from SEQ ID NOS: 20-24 of US 2008/0025980:

SEQ ID No: 20 of US 2008/0025980 (SEQ ID NO: 9):
QVQLVQSGSELKKPGASVKISCKASGYSFSNYGMNWVRQAPGQGLQWMGWI

NTDSGESTYAEEFKGRFVFSLDTSVSTAYLQITSLTAEDTGMYFCAKVGYD

ALDYWGQGTLVTVSS;

SEQ ID No: 21 of US 2008/0025980 (SEQ ID NO: 10):
QVQLVQSGSELKKPGASVKISCKASGYTFTNYGMNWVRQAPGQGLQWMGWI

NTDSGESTYAEEFKGRFVFSLDTSVSTAYLQITSLTAEDTGMYFCAKVGYD

ALDYWGQGTLVTVSS;

SEQ ID No: 22 of US 2008/0025980 (SEQ ID NO: 11):
QVQLVQSGSELKKPGASVKISCKASGYTFTNYGMNWVRQAPGQGLQWMGWI

NTDSGESTYAEEFKGRFVFSLDTSVNTAYLQITSLTAEDTGMYFCVRVGYD

ALDYWGQGTLVTVSS;

SEQ ID No: 23 of US 2008/0025980 (SEQ ID NO: 12):
QIQLVQSGSELKKPGASVKISCKASGYTFTNYGMNWVRQAPGQGLQWMGWI

NTDSGESTYAEEFKGRFVFSLDTSVNTAYLQITSLTAEDTGMYFCVRVGYD

ALDYWGQGTLVTVSS;

SEQ ID No: 24 of US 2008/0025980 (SEQ ID NO: 13):
QIQLVQSGSELKKPGASVKISCKASGYTFTNYGMNWVKQAPGQGLKWMGWI

NTDSGESTYAEEFKGRFAFSLDTSVNTAYLQITSLNAEDTGMYFCVRVGYD

ALDYWGQGTLVTVSS.

In an embodiment, the targeting moiety comprises a light chain comprising SEQ ID NO:18 of US 2008/0025980 and a heavy chain comprising SEQ ID NO:22 of US 2008/0025980.

In an embodiment, the targeting moiety comprises AMP-514 (aka MEDI-0680).

In an embodiment, the targeting moiety comprises the PD-L2-Fc fusion protein AMP-224, which is disclosed in WO2010/027827 and WO 2011/066342, the entire disclosures of which are hereby incorporated by reference. In such an embodiment, the targeting moiety may include a targeting domain which comprises SEQ ID NO:4 of WO2010/027827:

```
                                        (SEQ ID NO: 14)
LFTVTVPKELYIIEHGSNVTLECNFDTGSHVNLGAITASLQKVENDTSPHR

ERATLLEEQLPLGKASFHIPQVQVRDEGQYQCIIIYGVAWDYKYLTLKVKA

SYRKINTHILKVPETDEVELTCQATGYPLAEVSWPNVSVPANTSHSRTPEG

LYQVTSVLRLKPPPGRNFSCVFWNTHVRELTLASIDLQSQMEPRTHPTWLL

HIFIPFCIIAFIFIATVIALRKQLCQKLYSSKDTTKRPVTTTKREVNSAI
```

and/or the B7-DC fusion protein which comprises SEQ ID NO:83 of WO2010/027827:

```
                                        (SEQ ID NO: 15)
MIFLLLMLSLELQLHQTAALFTVTVPKELYIIEHGSNVTLECNFDTGSHVN

LGAITASLQKVENDTSPHRERATLLEEQLPLGKASFHIPQVQVRDEGQYQC

IIIYGVAWDYKYLTLKVKASYRKINTHILKVPETDEVELTCQATGYPLAEV

SWPNVSVPANTSHSRTPEGLYQVTSVLRLKPPPGRNFSCVFWNTHVRELTL

ASIDLQSQMEPRTHPTWEPKSCDKTHTCPPCPAPELLGGPSVFLFPPKPKD

TLMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

In an embodiment, the targeting moiety comprises the peptide AUNP 12 or any of the other peptides disclosed in US 2011/0318373 or 8,907,053. For example, the targeting moiety may comprise AUNP 12 (i.e., Compound 8 or SEQ ID NO:49 of US 2011/0318373) which has the sequence of:

SNTSESFK (SNTSESF) FRVTQLAPKAQIKE-NH2 (SEQ ID NO: 16)

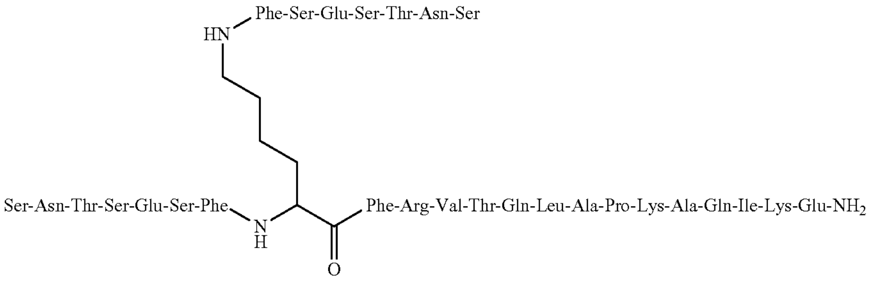

or:

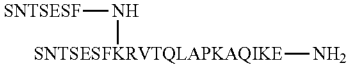

In an embodiment, the targeting moiety comprises the anti-PD-1 antibody 1E3, or fragments thereof, as disclosed in US 2014/0044738, the entire disclosures of which are hereby incorporated by reference. In illustrative embodiments, 1E3 or an antigen-binding fragment thereof for use in the methods provided herein comprises a heavy chain variable region comprising the amino acid sequence of:

```
                                        (SEQ ID NO: 17)
EVQLQQSGPV LVKPGASVKM SCKASGYTFT DYYMNWVKQS

HGKSLEWIGN INPYNGGTTY NQKFKGKATL TVDKSSRTAY

MEINSLTSED SAVYYCARGR IYDGSLDYWG QGTALTVSS;
```

and/or a light chain variable region comprising the amino acid sequence of:

```
                                        (SEQ ID NO: 18)
DIQMTQFPSS LCASQGGKVT VTCKASQDIN NYMAWYQHKP

GKGPRLLIHY TSTLLSGIPS RFSGSGSGRD YSFSISNLEP

EDIATYYCLQ YDNLWTFGGG TKLEIK.
```

In an embodiment, the targeting moiety comprises the anti-PD-1 antibody 1E8, or fragments thereof, as disclosed in US 2014/0044738, the entire disclosures of which are hereby incorporated by reference. In illustrative embodiments, 1E8 or an antigen-binding fragment thereof for use in the methods provided herein comprises a heavy chain variable region comprising the amino acid sequence of:

```
                                        (SEQ ID NO: 19)
QVQLQQSGAE LAKPGASVRL SCKASGYTFT NYWMHWVKQR

PGQGLEWIGH INPSSGFTTY NQNFKDKATL TADKSSNTAY

MQLSSLTYED SAVYFCARED YDVDYWGQGT TLTVSS;
```

and/or a light chain variable region comprising the amino acid sequence of:

```
                                        (SEQ ID NO: 20)
DIVMTQSQKF MSTSVGDRVS VTCKASQSVD TNVAWYQQKP

GQSPKALIFS ASYRYSGVPD RFTGSGSGTD FTLTINSVQS

EDLAEYFCQQ YNSYPYTFGS GTKLEIK.
```

In an embodiment, the targeting moiety comprises the anti-PD-1 antibody 1H3, or fragments thereof, as disclosed in US 2014/0044738, the entire disclosures of which are hereby incorporated by reference. In illustrative embodiments, 1H3 or an antigen-binding fragment thereof for use in the methods provided herein comprises a heavy chain variable region comprising the amino acid sequence of:

```
                                    (SEQ ID NO: 21)
EVQLVESGGG LVKPGGSLKL SCAASGFTFS DYGMHWVRQA

PEKGLEWVAY ISSGSYTIYY TDTVKGRFTI SRDNAKNTLF

LQMTSLRSED TAMYYCARRG YGSFYEYYFD YWGQGTTLTV SS;
```

and/or light chain variable region comprising the amino acid sequence of:

```
                                    (SEQ ID NO: 22)
QIVLTQSPAL MSASPGEKVT MTCSASSSVS YMYWYQQKPR

SSPKPWIYLT SNLASGVPAR FSGSGSGTSY SLTISSMEAE

DAATYYCQQW SSNPFTFGSG TKLEIK.
```

In an embodiment, the targeting moiety comprises a VHH directed against PD-1 as disclosed, for example, in U.S. Pat. No. 8,907,065 and WO 2008/071447, the entire disclosures of which are hereby incorporated by reference. In illustrative embodiments, the VHHs against PD-1 comprise SEQ ID NOS: 347-351 of U.S. Pat. No. 8,907,065:

```
SEQ ID No: 347 of U.S. Pat. No. 8,907,065
(SEQ ID NO: 23):
EVQLVESGGGLVQAGKSLRLSCAASGSIFSIHAMGWFRQAPGKEREFVAA

ITWSGGITYYEDSVKGRFTISRDNAKNTVYLQMNSLKPEDTAIYYCAADR

AESSWYDYWGQGTQVTVSS;

SEQ ID No: 348 of U.S. Pat. No. 8,907,065
(SEQ ID NO: 24):
EVQLVESGGGLVQAGGSLRLSCAASGSIASIHAMGWFRQAPGKEREFVAV

ITWSGGITYYADSVKGRFTISRDNAKNTVYLQMNSLKPEDTAIYYCAGDK

HQSSWYDYWGQGTQVTVSS;

SEQ ID No: 349 of U.S. Pat. No. 8,907,065
(SEQ ID NO: 25):
EVQLVESGGGLVQAGGSLRLSCAASGSISSIHAMGWFRQAPGKEREFVAA

ITWSGGITYYADSLKGRFTISRDNAKNTGYLQMNSLKPEDTAIYYCAADR

AQSSWYDYWGQGTQVTVSS;

SEQ ID No: 350 of U.S. Pat. No. 8,907,065
(SEQ ID NO: 26):
EVQLVESGGGLVQAGGSLGLSCAASGSIFSINAMAWFRQAPGKEREFVAL

ISWSGGSTYYEDSVKGRFTISRDNAKNTVYLQMNSLKPEDTAIYYCAADR

VDSNWYDYWGQGTQVTVSS;

SEQ ID No: 351 of U.S. Pat. No. 8,907,065
(SEQ ID NO: 27):
EVQLVESGGGLVQAGGSLRLSCAASGRAFSSGTMGWFRRAPGKEREFVA

SIPWSGGRIYYADSVKGRFTISRDNAQNTVYLQMNSLKPEDTAVYYCAVK

ERSTGWDFASWGQCTQVTVSS.
```

In an embodiment, the targeting moiety comprises any one of the anti-PD-1 antibodies, or fragments thereof, as disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID NOS: 25-29 of US2011/0271358:

```
SEQ ID No: 25 of US2011/0271358 (SEQ ID NO: 28):
QVQLVQSGAELKQPGASVKMSCKASGYSFTSSWIHWVKQAPGQGLEWIGYI

YPSTGFTEYNQKFKDRATLTADKSTSTAYMELSSLRSEDSAVYYCARWRDS

SGYHAMDYWGQGTSVTVSS;

SEQ ID No: 26 of US2011/0271358 (SEQ ID NO: 29):
QVQLVQSGAEVKQPGASVKMSCKASGYSFTSSWIHWVKQAPGQGLEWIGYI

YPSTGFTEYNQKFKDRATLTADKSTSTAYMELSSLRSEDTAVYY3/d10CA

RWRDSSGYHAMDYWGQGTSVTVSS;

SEQ ID No: 27 of US2011/0271358 (SEQ ID NO: 30):
QVQLVQSGHEVKQPGASVKMSCKASGYSFTSSWIHWVKQAPGQGLEWIGYI

YPSTGFTEYNQKFKDRATLTADKSTSTAYMELSSLRSEDTAVYYCARWRDS

SGYHAMDYWGQGTLVTVSS;

SEQ ID No: 28 of US2011/0271358 (SEQ ID NO: 31):
QVQLVQSGHEVKQPGASVKMSCKASGYSFTSSWIHWVRQAPGQGLEWIGYI

YPSTGFTEYNQKFKDRATLTADKSTSTAYMELSSLRSEDTAVYYCARWRDS

SGYHAMDYWGQGTLVTVSS;

SEQ ID No: 29 of US2011/0271358 (SEQ ID NO: 32):
QVQLVQSGHEVKQPGASVKVSCKASGYSFTSSWIHWVRQAPGQGLEWIGYI

YPSTGFTEYNQKFKDRATITADKSTSTAYMELSSLRSEDTAVYYCARWRDS

SGYHAMDYWGQGTLVTVSS;
```

and/or a light chain comprising an amino acid sequence selected from SEQ ID NOS: 30-33 of US2011/0271358:

```
SEQ ID No: 30 of US2011/0271358 (SEQ ID NO: 33):
DIVLTQSPASLTLSPGQRLTISCRASQSVSTSGYSYMHWYQQKPDQSPK

LLIKFGSNLESGIPARFSGSGSGTDFTLTISSLEEEDFATYYCQHSWEI

PYTFGQGTKLEIK;

SEQ ID No: 31 of US2011/0271358 (SEQ ID NO: 34):
DIVLTQSPATLSLSPGQRLTISCRASQSVSTSGYSYMHWYQQKPDQSPK

LLIKFGSNLESGIPARFSGSGSGTDFTLTISSLEPEDFATYYCQHSWEI

PYTFGQGTKLEIK;

SEQ ID No: 32 of US2011/0271358 (SEQ ID NO: 35):
EIVLTQSPATLSLSPGQRLTISCRASQSVSTSGYSYMHWYQQKPDQSPK

LLIKFGSNLESGIPARFSGSGSGTDFTLTISSLEPEDFATYYCQHSWEI

PYTFGQGTKLEIK;

SEQ ID No: 33 of US2011/0271358 (SEQ ID NO: 36):
DIVLTQSPATLSLSPGQRLTISCRASQSVSTSGYSYMHWYQQKPDQSPK

LLIKFGSNLESGIPARFSGSGSGTDFTLTISSLEPEDFAVYYCQHSWEI

PYTFGQGTKLEIK.
```

In various embodiments, the present chimeric protein comprises an antibody directed against PD-1, or an antibody fragment thereof, selected from TSR-042 (Tesaro, Inc.), REGN2810 (Regeneron Pharmaceuticals, Inc.), PDR001 (Novartis Pharmaceuticals), and BGB-A317 (BeiGene Ltd.) In various embodiments, the present chimeric protein has one targeting moiety directed against PD-L1. In some embodiments, the chimeric protein has one targeting moiety which selectively bind a PD-L1 polypeptide. In some embodiments, the chimeric protein include an antibody, an antibody derivative or format, a peptide or polypeptide, or a fusion proteins that selectively binds a PD-L1 polypeptide.

In an embodiment, the targeting moiety comprises the anti-PD-L1 antibody MEDI4736 (aka durvalumab), or fragments thereof. MEDI4736 is selective for PD-L1 and blocks the binding of PD-L1 to the PD-1 and CD80 receptors. MEDI4736 and antigen-binding fragments thereof for use in the methods provided herein comprises a heavy chain and a light chain or a heavy chain variable region and a light chain variable region. The sequence of MEDI4736 is disclosed in WO/2016/06272, the entire contents of which are hereby incorporated by reference. In illustrative embodiments, MEDI4736 or an antigen-binding fragment thereof for use in the methods provided herein comprises a heavy chain comprising the amino acid sequence of:

```
                                            (SEQ ID NO: 37)
EVQLVESGGG LVQPGGSLRL SCAASGFTFS RYWMSWVRQA
PGKGLEWVAN IKQDGSEKYY VDSVKGRFTI SRDNAKNSLY
LQMNSLRAED TAVYYCAREG GWFGELAFDY WGQGTLVTVS
SASTKGPSVF PLAPSSKSTS GGTAALGCLV KDYFPEPVTV
SWNSGALTSG VHTFPAVLQS SGLYSLSSVV TVPSSSLGTQ
TYICNVNHKP SNTKVDKRVE PKSCDKTHTC PPCPAPEFEG
GPSVFLFPPK PKDTLMISRT PEVTCVVVDV SHEDPEVKFN
WYVDGVEVHN AKTKPREEQY NSTYRVVSVL TVLHQDWLNG
KEYKCKVSNK ALPASIEKTI SKAKGQPREP QVYTLPPSRE
EMTKNQVSLT CLVKGFYPSD IAVEWESNGQ PENNYKTTPP
VLDSDGSFFL YSKLTVDKSR WQQGNVFSCS VMHEALHNHY
TQKSLSLSPG K;
```

and/or a light chain comprising the amino acid sequence of:

```
                                            (SEQ ID NO: 38)
EIVLTQSPGT LSLSPGERAT LSCRASQRVS SSYLAWYQQK
PGQAPRLLIY DASSRATGIP DRFSGSGSGT DFTLTISRLE
PEDFAVYYCQ QYGSLPWTFG QGTKVEIKRT VAAPSVFIFP
PSDEQLKSGT ASVVCLLNNF YPREAKVQWK VDNALQSGNS
QESVTEQDSK DSTYSLSSTL TLSKADYEKH KVYACEVTHQ
GLSSPVTKSF NRGEC.
```

In illustrative embodiments, the MED14736 or an antigen-binding fragment thereof for use in the methods provided herein comprises a heavy chain variable region comprising the amino acid sequence of SEQ ID NO:4 of WO/2016/06272:

```
                                            (SEQ ID NO: 39)
EVQLVESGGGLVQPGGSLRLSCAASGFTFSRYWMSWVRQAPGKGLEWVA
NIKQDGSEKYYVDSVKGRFTISRDNAKNSLYLQMNSLRAEDTAVYYCAR
EGGWFGELAFDYWGQGTLVTVSS;
```

and/or a light chain variable region comprising the amino acid sequence of SEQ ID NO:3 of WO/2016/06272:

```
                                            (SEQ ID NO: 40)
EIVLTQSPGTLSLSPGERATLSCRASQRVSSSYLAWYQQKPGQAPRLLI
YDASSRATGIPDRFSGSGSGTDFTLTISRLEPEDFAVYYCQQYGSLPWT
FGQGTKVEIK
```

In an embodiment, the targeting moiety comprises the anti-PD-L1 antibody atezolizumab (aka MPDL3280A, RG7446), or fragments thereof. In illustrative embodiments, atezolizumab or an antigen-binding fragment thereof for use in the methods provided herein comprises a heavy chain comprising the amino acid sequence of:

```
                                            (SEQ ID NO: 41)
EVQLVESGGGLVQPGGSLRLSCAASGFTFSDSWIHWVRQAPGKGLEWVAWI
SPYGGSTYYADSVKGRFTISADTSKNTAYLQMNSLRAEDTAVYYCARRHWP
GGFDYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVN
HKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYASTYRVVSV
LTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLY
SKLTVDKSRWQQGNVFSCSVMHEALHNHYTQKSLSLSPGK;
```

and/or a light chain comprising the amino acid sequence of:

```
                                            (SEQ ID NO: 42)
DIQMTQSPSSLSASVGDRVTITCRASQDVSTAVAWYQQKPGKAPKLLIY
SASFLYSGVPSRFSGSGSGTDFTLTISSLQPEDFATYYCQQYLYHPATF
GQGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC.
```

In an embodiment, the targeting moiety comprises the anti-PD-L1 antibody avelumab (aka MSB0010718C), or fragments thereof. In illustrative embodiments, avelumab or an antigen-binding fragment thereof for use in the methods provided herein comprises a heavy chain comprising the amino acid sequence of:

```
                                            (SEQ ID NO: 43)
EVQLLESGGG LVQPGGSLRL SCAASGFTFS SYIMMWVRQA
PGKGLEWVSS IYPSGGITFY ADTVKGRFTI SRDNSKNTLY
LQMNSLRAED TAVYYCARIK LGTVTTVDYW GQGTLVTVSS
ASTKGPSVFP LAPSSKSTSG GTAALGCLVK DYFPEPVTVS
WNSGALTSGV HTFPAVLQSS GLYSLSSVVT VPSSSLGTQT
YICNVNHKPS NTKVDKKVEP KSCDKTHTCP PCPAPELLGG
```

-continued

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK;

and/or a light chain comprising the amino acid sequence of:

(SEQ ID NO: 44)

QSALTQPASV SGSPGQSITI SCTGTSSDVG GYNYVSWYQQ

HPGKAPKLMI YDVSNRPSGV SNRFSGSKSG NTASLTISGL

QAEDEADYYC SSYTSSSTRV FGTGTKVTVL GQPKANPTVT

LFPPSSEELQ ANKATLVCLI SDFYPGAVTV AWKADGSPVK

AGVETTKPSK QSNNKYAASS YLSLTPEQWK SHRSYSCQVT

HEGSTVEKTV APTECS.

In an embodiment, the targeting moiety comprises the anti-PD-L1 antibody BMS-936559 (aka 12A4, MDX-1105), or fragments thereof, as disclosed in US 2013/0309250 and WO2007/005874, the entire disclosures of which are hereby incorporated by reference. In illustrative embodiments, BMS-936559 or an antigen-binding fragment thereof for use in the methods provided herein comprises a heavy chain variable region comprising the amino acid sequence of:

(SEQ ID NO: 45)

QVQLVQSGAEVKKPGSSVKVSCKTSGDTFSTYAISWVRQAPGQGLEWMG

GIIPIFGKAHYAQKFQGRVTITADESTSTAYMELSSLRSEDTAVYFCAR

KFHFVSGSPFGMDVWGQGTTVTVSS;

and/or a light chain variable region comprising the amino acid sequence of:

(SEQ ID NO: 46)

EIVLTQSPATLSLSPGERATLSCRASQSVSSYLAWYQQKPGQAPRLLIY

DASNRATGIPARFSGSGSGTDFTLTISSLEPEDFAVYYCQQRSNWPTFG

QGTKVEIK.

In an embodiment, the targeting moiety comprises the anti-PD-L1 antibody 3G10, or fragments thereof, as disclosed in US 2013/0309250 and WO2007/005874, the entire disclosures of which are hereby incorporated by reference. In illustrative embodiments, 3G10 or an antigen-binding fragment thereof for use in the methods provided herein comprises a heavy chain variable region comprising the amino acid sequence of:

(SEQ ID NO: 47)

QVQLVQSGAEVKKPGASVKVSCKASGYTFTDYGFSWVRQAPGQGLEWMGW

ITAYNGNTNYAQKLQGRVTMTTDTSTSTVYMELRSLRSDDTAVYYCARDY

FYGMDVWGQGTTVTVSS;

and/or a light chain variable region comprising the amino acid sequence of:

(SEQ ID NO: 48)

EIVLTQSPATLSLSPGERATLSCRASQSVSSYLVWYQQKPGQAPRLLIY

DASNRATGIPARFSGSGSGTDFTLTISSLEPEDFAVYYCQQRSNWPRTF

GQGTKVEIK.

In an embodiment, the targeting moiety comprises the anti-PD-L1 antibody 10A5, or fragments thereof, as disclosed in US 2013/0309250 and WO2007/005874, the entire disclosures of which are hereby incorporated by reference. In illustrative embodiments, 10A5 or an antigen-binding fragment thereof for use in the methods provided herein comprises a heavy chain variable region comprising the amino acid sequence of:

(SEQ ID NO: 49)

QVQLVQSGAEVKKPGASVKVSCKASGYTFTSYDVHWVRQAPGQRLEWMG

WLHADTGITKFSQKFQGRVTITRDTSASTAYMELSSLRSEDTAVYYCAR

ERIQLWFDYWGQGTLVTVSS;

and/or a light chain variable region comprising the amino acid sequence of:

(SEQ ID NO: 50)

DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK.

In an embodiment, the targeting moiety comprises the anti-PD-L1 antibody 5F8, or fragments thereof, as disclosed in US 2013/0309250 and WO2007/005874, the entire disclosures of which are hereby incorporated by reference. In illustrative embodiments, 5F8 or an antigen-binding fragment thereof for use in the methods provided herein comprises a heavy chain variable region comprising the amino acid sequence of:

(SEQ ID NO: 51)

QVQLVQSGAEVKKPGSSVKVSCKVSGGIFSTYAINWVRQAPGQGLEWMGG

IIPIFGTANHAQKFQGRVTITADESTSTAYMELSSLRSEDTAVYYCARDQ

GIAAALFDYWGQGTLVTVSS;

and/or a light chain variable region comprising the amino acid sequence of:

(SEQ ID NO: 52)

EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPWTFG

QGTKVEIK.

In an embodiment, the targeting moiety comprises the anti-PD-L1 antibody 10H10, or fragments thereof, as disclosed in US 2013/0309250 and WO2007/005874, the entire disclosures of which are hereby incorporated by reference. In illustrative embodiments, 10H10 or an antigen-binding fragment thereof for use in the methods provided herein comprises a heavy chain variable region comprising the amino acid sequence of:

```
                                        (SEQ ID NO: 53)
EVQLVESGGGLVQPGRSLRLSCAVSGFTFDDYVVHWVRQAPGKGLEWVSG

ISGNSGNIGYADSVKGRFTISRDNAKNSLYLQMNSLRAEDTALYYCAVPF

DYWGQGTLVTVSS;
```

and/or a light chain variable region comprising the amino acid sequence of:

```
                                        (SEQ ID NO: 54)
DIQMTQSPSSLSASVGDRVTITCRASQGISSWLAWYQQKPEKAPKSLIYA

ASSLQSGVPSRFSGSGSGTDFTLTISSLQPEDFATYYCQQYNSYPYTFGQ

GTKLEIK.
```

In an embodiment, the targeting moiety comprises the anti-PD-L1 antibody 1B12, or fragments thereof, as disclosed in US 2013/0309250 and WO2007/005874, the entire disclosures of which are hereby incorporated by reference. In illustrative embodiments, 1B12 or an antigen-binding fragment thereof for use in the methods provided herein comprises a heavy chain variable region comprising the amino acid sequence of:

```
                                        (SEQ ID NO: 55)
QVQLVQSGAEVKKPGSSVKVSCKTSGDTFSSYAISWVRQAPGQGLEWMGG

IIPIFGRAHYAQKFQGRVTITADESTSTAYMELSSLRSEDTAVYFCARKF

HFVSGSPFGMDVWGQGTTVTVSS;
```

and/or a light chain variable region comprising the amino acid sequence of:

```
                                        (SEQ ID NO: 56)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPTFGQG

TKVEIK.
```

In an embodiment, the targeting moiety comprises the anti-PD-L1 antibody 7H1, or fragments thereof, as disclosed in US 2013/0309250 and WO2007/005874, the entire disclosures of which are hereby incorporated by reference. In illustrative embodiments, 7H1 or an antigen-binding fragment thereof for use in the methods provided herein comprises a heavy chain variable region comprising the amino acid sequence of:

```
                                        (SEQ ID NO: 57)
QVQLVQSGAEVKKPGSSVKVSCKTSGGTFSSYAISWVRQAPGQGLEWMGG

IIPIFGKAHYAQKFQGRVTITADESTTTAYMELSSLRSEDTAVYYCARKY

DYVSGSPFGMDVWGQGTTVTVSS;
```

and/or a light chain variable region comprising the amino acid sequence of:

```
                                        (SEQ ID NO: 58)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPTFGQG

TKVEIK.
```

In an embodiment, the targeting moiety comprises the anti-PD-L1 antibody 11E6, or fragments thereof, as disclosed in US 2013/0309250 and WO2007/005874, the entire disclosures of which are hereby incorporated by reference. In illustrative embodiments, 11E6 or an antigen-binding fragment thereof for use in the methods provided herein comprises a heavy chain variable region comprising the amino acid sequence of:

```
                                        (SEQ ID NO: 59)
QVQLVQSGAEVKKPGSSVKVSCKASGGTFSSYAINWVRQAPGQGLEWMGG

IIPIFGSANYAQKFQDRVTITADESTSAAYMELSSLRSEDTAVYYCARDS

SGWSRYYMDVWGQGTTVTVSS;
```

and/or a light chain variable region comprising the amino acid sequence of:

```
                                        (SEQ ID NO: 60)
EIVLTQSPGTLSLSPGERATLSCRASQSVSSSYLAWYQQKPGQAPRLLIY

GASSRATGIPDRFSGSGSGTDFTLTISRLEPEDFAVYYCQQYGSSPFGGG

TKVEIK.
```

In an embodiment, the targeting moiety comprises the anti-PD-L1 antibody 12B7, or fragments thereof, as disclosed in US 2013/0309250 and WO2007/005874, the entire disclosures of which are hereby incorporated by reference. In illustrative embodiments, 12B7 or an antigen-binding fragment thereof for use in the methods provided herein comprises a heavy chain variable region comprising the amino acid sequence of:

```
                                        (SEQ ID NO: 61)
QVQLVQSGAEVKEPGSSVKVSCKASGGTENSYAISWVRQAPGQGLEWMGG

IIPLFGIAHYAQKFQGRVTITADESTNTAYMDLSSLRSEDTAVYYCARKY

SYVSGSPFGMDVWGQGTTVTVSS;
```

and/or a light chain variable region comprising the amino acid sequence of:

```
                                        (SEQ ID NO: 62)
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPTFGQG

TRLEIK.
```

In an embodiment, the targeting moiety comprises the anti-PD-L1 antibody 13G4, or fragments thereof, as disclosed in US 2013/0309250 and WO2007/005874, the entire disclosures of which are hereby incorporated by reference. In illustrative embodiments, 13G4 or an antigen-binding fragment thereof for use in the methods provided herein comprises a heavy chain variable region comprising the amino acid sequence of:

```
                                        (SEQ ID NO: 63)
EVQLVESGGGLVQPGRSLRLSCAASGITFDDYGMHWVRQAPGKGLEWVSG

ISWNRGRIEYADSVKGRFTISRDNAKNSLYLQMNSLRAEDTALYYCAKGR

FRYFDWFLDYWGQGTLVIVSS;
```

and/or a light chain variable region comprising the amino acid sequence of:

(SEQ ID NO: 64)
AIQLTQSPSSLSASVGDRVTITCRASQGISSALAWYQQKPGKAPKLLIYD
ASSLESGVPSRFSGSGSGTDFTLTISSLQPEDFATYYCQQFNSYPFTFGP
GTKVDIK.

In an embodiment, the targeting moiety comprises the anti-PD-L1 antibody 1E12, or fragments thereof, as disclosed in US 2014/0044738, the entire disclosures of which are hereby incorporated by reference. In illustrative embodiments, 1E12 or an antigen-binding fragment thereof for use in the methods provided herein comprises a heavy chain variable region comprising the amino acid sequence of:

(SEQ ID NO: 65)
EVKLQESGPS LVKPSQTLSL TCSVTGYSIT SDYWNWIRKF
PGNKLEYVGY ISYTGSTYYN PSLKSRISIT RDTSKNQYYL
QLNSVTSEDT ATYYCARYGG WLSPFDYWGQ GTTLTVSS;

and/or a light chain variable region comprising the amino acid sequence of:

(SEQ ID NO: 66)
DIVMTQSHKL MSTSVGDRVS ITCKASQDVG TAVAWYQQKP
GQSPKLLIYW ASTRHTGVPD RFTGSGSGTD FTLTISNVQS
EDLADYFCQQ DSSYPLTFGA GTKVELK.

In an embodiment, the targeting moiety comprises the anti-PD-L1 antibody 1F4, or fragments thereof, as disclosed in US 2014/0044738, the entire disclosures of which are hereby incorporated by reference. In illustrative embodiments, 1F4 or an antigen-binding fragment thereof for use in the methods provided herein comprises a heavy chain variable region comprising the amino acid sequence of:

(SEQ ID NO: 67)
EVQLQESGPG LVAPSQSLSI TCTVSGFSLT TYSINWIRQP
PGKGLEWLGV MWAGGGTNSN SVLKSRLIIS KDNSKSQVFL
KMNSLQTDDT ARYYCARYYG NSPYYAIDYW GQGTSVTVSS;

and/or a light chain variable region comprising the amino acid sequence of:

(SEQ ID NO: 68)
DIVTTQSHKL MSTSVGDRVS ITCKASQDVG TAVAWYQQKP
GQSPKLLIYW ASTRHTGVPD RFTGSGSGTD FTLTISNVQS
EDLADYFCQQ DSSYPLTFGA GTKVELK.

In an embodiment, the targeting moiety comprises the anti-PD-L1 antibody 2G11, or fragments thereof, as disclosed in US 2014/0044738, the entire disclosures of which are hereby incorporated by reference. In illustrative embodiments, 2G11 or an antigen-binding fragment thereof for use in the methods provided herein comprises a heavy chain variable region comprising the amino acid sequence of:

(SEQ ID NO: 69)
EVKLQESGPS LVKPSQTLSL TCSVTGYSII SDYWNWIRKF
PGNKLEYLGY ISYTGSTYYN PSLKSRISIT RDTSKNQYYL
QLNSVTTEDT ATYYCARRGG WLLPFDYWGQ GTTLTVSS;

and/or a light chain variable region comprising the amino acid sequence of:

(SEQ ID NO: 70)
DIVMTQSPSS LAVSVGEKVS MGCKSSQSLL YSSNQKNSLA
WYQQKPGQSP KLLIDWASTR ESGVPDRFTG SGSGTDFTLT
ISSVKAEDLA VYYCQQYYGY PLTFGAGTKL ELK.

In an embodiment, the targeting moiety comprises the anti-PD-L1 antibody 3B6, or fragments thereof, as disclosed in US 2014/0044738, the entire disclosures of which are hereby incorporated by reference. In illustrative embodiments, 3B6 or an antigen-binding fragment thereof for use in the methods provided herein comprises a heavy chain variable region comprising the amino acid sequence of:

(SEQ ID NO: 71)
EVKLQESGPS LVKPGASVKL SCKASGYTFT SYDINWVKQR
PGQGLEWIGW IFPRDNNTKY NENFKGKATL TVDTSSTTAY
MELHSLTSED SAVYFCTKEN WVGDFDYWGQ GTTLTLSS;

and/or a light chain variable region comprising the amino acid sequence of:

(SEQ ID NO: 72)
DIVMTQSPAI MSASPGEKVT MTCSASSSIR YMHWYQQKPG
TSPKRWISDT SKLTSGVPAR FSGSGSGTSY ALTISSMEAE
DAATYYCHQR SSYPWTFGGG TKLEIK.

In an embodiment, the targeting moiety comprises the anti-PD-L1 antibody 3D10, or fragments thereof, as disclosed in US 2014/0044738 and WO2012/145493, the entire disclosures of which are hereby incorporated by reference. In illustrative embodiments, 3D10 or an antigen-binding fragment thereof for use in the methods provided herein comprises a heavy chain variable region comprising the amino acid sequence of:

(SEQ ID NO: 73)
EVQLQQSGPD LVTPGASVRI SCQASGYTFP DYYMNWVKQS
HGKSLEWIGD IDPNYGGTTY NQKFKGKAIL TVDRSSSTAY
MELRSLTSED SAVYYCARGA LTDWGQGTSL TVSS;

and/or a light chain variable region comprising the amino acid sequence of:

(SEQ ID NO: 74)
QIVLSQSPAI LSASPGEKVT MTCRASSSVS YIYWFQQKPG
SSPKPWIYAT FNLASGVPAR FSGSGSGTSY SLTISRVETE
DAATYYCQQW SNNPLTFGAG TKLELK.

In an embodiment, the targeting moiety comprises any one of the anti-PD-L1 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 34-38 of US2011/0271358:

SEQ ID No: 34 of US2011/0271358
(SEQ ID NO: 75):
EVQLVQSGPELKKPGASVKNISCKASGYTFTSYVMHWVKQAPG

QRLEWIGYVNPFNDGTKYNEMFKGRATLTSDKSTSTAYMELSS

LRSEDSAVYYCARQAWGYPWGQGTLVTVSS;

SEQ ID No: 35 of US2011/0271358
(SEQ ID NO: 76):
EVQLVQSGAEVKKPGASVKNISCKASGYTFTSYVMHWVKQAPG

QRLEWIGYVNPFNDGTKYNEMFKGRATLTSDKSTSTAYMELSS

LRSEDTAVYYCARQAWGYPWGQGTLVTVSS;

SEQ ID No: 36 of US2011/0271358
(SEQ ID NO: 77):
EVQLVQSGAEVKKPGASVKMSCKASGYTFTSYVMHWVRQAPGQ

RLEWIGYVNPFNDGTKYNEMFKGRATLTSDKSTSTAYMELSSL

RSEDTAVYYCARQAWGYPWGQGTLVTVSS;

SEQ ID No: 37 of US2011/0271358
(SEQ ID NO: 78):
EVQLVQSGAEVKKPGASVKVSCKASGYTFTSYVMHWVRQAPG

QRLEWIGYVNPFNDGTKYNEMFKGRATLTSDKSTSTAYMELSS

LRSEDTAVYYCARQAWGYPWGQGTLVTVSS;

SEQ ID No: 38 of US2011/0271358
(SEQ ID NO: 79):
EVQLVQSGAEVKKPGASVKVSCKASGYTFTSYVMHWVRQAPG

QRLEWIGYVNPFNDGTKYNEMFKGRATITSDKSTSTAYMELS

SLRSEDTAVYYCARQAWGYPWGQGTLVTVSS;

and/or a light chain comprising an amino acid sequence selected from SEQ ID Nos: 39-42 of US2011/0271358:

SEQ ID No: 39 of US2011/0271358
(SEQ ID NO: 80):
DIVLTQSPASLALSPGERATLSCRATESVEYYGTSLVQWYQQ

KPGQPPKLLIYAASSVDSGVPSRFSGSGSGTDFTLTINSLEE

EDAAMYFCQQSRRVPYTFGQGTKLEIK;

SEQ ID No: 40 of US2011/0271358
(SEQ ID NO: 81):
DIVLTQSPATLSLSPGERATLSCRATESVEYYGTSLVQWYQQ

KPGQPPKLLIYAASSVDSGVPSRFSGSGSGTDFTLTINSLEA

EDAAMYFCQQSRRVPYTFGQGTKLEIK;

SEQ ID No: 41 of US2011/0271358
(SEQ ID NO: 82):
EIVLTQSPATLSLSPGERATLSCRATESVEYYGTSLVQWYQQ

KPGQPPKLLIYAASSVDSGVPSRFSGSGSGTDFTLTINSLEA

EDAAMYFCQQSRRVPYTFGQGTKLEIK;

-continued

SEQ ID No: 42 of US2011/0271358
(SEQ ID NO: 83):
DIVLTQSPATLSLSPGERATLSCRATESVEYYGTSLVQWYQQ

KPGQPPKLLIYAASSVDSGVPSRFSGSGSGTDFTLTINSLEA

EDAATYFCQQSRRVPYTFGQGTKLEIK.

In an embodiment, the targeting moiety comprises the anti-PD-L1 antibody 2.7A4, or fragments thereof, as disclosed in WO 2011/066389, U.S. Pat. No. 8,779,108, and US2014/0356353, the entire disclosures of which are hereby incorporated by reference. In illustrative embodiments, 2.7A4 or an antigen-binding fragment thereof for use in the methods provided herein comprises a heavy chain variable region comprising the amino acid sequence of:

SEQ ID No: 2 of WO 2011/066389 (SEQ ID NO: 84):
EVQLVESGGGLVKPGGSLRLSCAASGFTFSTYSMNWVRQAPGKGLEWVSS

ISSSGDYIYYADSVKGRFTISRDNAKNSLFLQMNSLKAEDTAVYYCARDL

VTSMVAFDYWGQGTLVTVSS;

and/or a light chain variable region comprising the amino acid sequence of:

SEQ ID No: 7 of WO 2011/066389 (SEQ ID NO: 85):

SYELTQPPSVSVSPGQAARITCSGDALPQKYVFWYQQKSGQAPVLVIYED

SKRPSGIPERFSGSSSGTMATLTISGAQVEDEADYYCYSTDRSGNHRVFG

GGTRLTVL.

In an embodiment, the targeting moiety comprises the anti-PD-L1 antibody 2.9D10, or fragments thereof, as disclosed in WO 2011/066389, U.S. Pat. No. 8,779,108, and US2014/0356353, the entire disclosures of which are hereby incorporated by reference. In illustrative embodiments, 2.9D10 or an antigen-binding fragment thereof for use in the methods provided herein comprises a heavy chain variable region comprising the amino acid sequence of:

SEQ ID No: 12 of WO 2011/066389 (SEQ ID NO: 86):
EVQLVESGGGLVQPGGSLRLSCAASGFTFSSYWMSWVRQAPGKGLEWVA

NIKQDGGEQYYVDSVKGRFTISRDNAKNSLYLQMNSLRAEDTAVYYCAR

DWNYGYYDMDVWGQGTTVTVSS;

and/or a light chain variable region comprising the amino acid sequence of:

SEQ ID No: 17 of WO 2011/066389 (SEQ ID NO: 87):
EIVLTQSPGTLSLSPGERATLSCRASQSVSSNYLAWFQQKPGQAPRLL

IFGTSSRATGIPDRFSGSGSGTDFTLTISRLEPEDFAVYYCQQYGSSI

FTFGPGTKVDIK.

In an embodiment, the targeting moiety comprises the anti-PD-L1 antibody 2.14H9, or fragments thereof, as disclosed in WO 2011/066389, U.S. Pat. No. 8,779,108, and US2014/0356353, the entire disclosures of which are hereby incorporated by reference. In illustrative embodiments, 2.14H9 or an antigen-binding fragment thereof for use in the methods provided herein comprises a heavy chain variable region comprising the amino acid sequence of:

SEQ ID No: 22 of WO 2011/066389 (SEQ ID NO: 88):
EVQLVESGGGLVQPGGSLRLSCAASGFTFSRYWMSWVRQAPGKGLEWVANI

KQDGSEKYYVDSVKGRFTISRDNAKNSLYLQMNSLRAEDTAVYYCAREGGW

FGELAFDYWGQGTLVTVSS;

and/or a light chain variable region comprising the amino acid sequence of:

SEQ ID No: 27 of WO 2011/066389 (SEQ ID NO: 89):
EIVLTQSPGTLSLSPGERATLSCRASQRVSSSYLAWYQQKPGQAPRLLIYD

ASSRATGIPDRFSGSGSGTDFTLTISRLEPEDFAVYYCQQYGSLPWTFGQG

TEVEIK.

In an embodiment, the targeting moiety comprises the anti-PD-L1 antibody 2.20A8, or fragments thereof, as disclosed in WO 2011/066389, U.S. Pat. No. 8,779,108, and US2014/0356353, the entire disclosures of which are hereby incorporated by reference. In illustrative embodiments, 2.20A8 or an antigen-binding fragment thereof for use in the methods provided herein comprises a heavy chain variable region comprising the amino acid sequence of:

SEQ ID No: 32 of WO 2011/066389 (SEQ ID NO: 90):
EVQLLESGGGLVQPGGSLRLSCAASGFTFSNYAMSWVRQAPGKGLEWVSAI

RGSGGSTYYADSVKGRFTISRDNSKNTLYLQMNSLRAEDTAVYYCAKDLHY

DSSGYLDYWGQGTLVTVSS;

and/or a light chain variable region comprising the amino acid sequence of:

SEQ ID No: 37 of WO 2011/066389 (SEQ ID NO: 91):
DIQMTQSPSSVSASVGDRVTITCRASQGIRSWLAWYQQKPGKAPKLLIYAI

SRLQSGVPSRFSGSGSGTDFTLTISSLQPEDFATYYCQQANSFPLTFGGGT

KVEIK.

In an embodiment, the targeting moiety comprises the anti-PD-L1 antibody 3.15G8, or fragments thereof, as disclosed in WO 2011/066389, U.S. Pat. No. 8,779,108, and US2014/0356353, the entire disclosures of which are hereby incorporated by reference. In illustrative embodiments, 3.15G8 or an antigen-binding fragment thereof for use in the methods provided herein comprises a heavy chain variable region comprising the amino acid sequence of:

SEQ ID No: 42 of WO 2011/066389 (SEQ ID NO: 92):
EVQLVESGGGLVQPGGSLRLSCAASGFTFSSYWMSWVRQAPGKGLEWVANI

KQDGGEKYYVDSVKGRFTISRDNAKNSLFLQMNSLRAEDTAVYYCARVQLY

SDYFDYWGQGTLVTVSS;

and/or a light chain variable region comprising the amino acid sequence of:

SEQ ID No: 47 of WO 2011/066389 (SEQ ID NO: 93):
DIQMTQSPSSVSASVGDRVTITCRASQGISSWLAWYQQKSGKAPKLLIYAA

SGLQSGVPSRFSGSGSGTDFTLTISSLQPEDLATYYCQQSHSLPPTFGQGT

KVEIK.

In an embodiment, the targeting moiety comprises the anti-PD-L1 antibody 3.18G1, or fragments thereof, as disclosed in WO 2011/066389, U.S. Pat. No. 8,779,108, and US2014/0356353, the entire disclosures of which are hereby incorporated by reference. In illustrative embodiments, 3.18G1 or an antigen-binding fragment thereof for use in the methods provided herein comprises a heavy chain variable region comprising the amino acid sequence of:

SEQ ID No: 52 of WO 2011/066389 (SEQ ID NO: 94):
EVQLLESGGDLVQPGGSLRLSCAASGFTFNSYAMSWVRQAPGKGLEWVSTI

SGSGGFTFSADSVKGRFTISRDNSKNTLFLQMNSLRVEDSAVYSCAKVLVG

FNNGCWDYWGQGTLVTVSS;

and/or a light chain variable region comprising the amino acid sequence of:

SEQ ID No: 57 of WO 2011/066389 (SEQ ID NO: 95):
SYVLTQPPSVSVAPGQTARITCGGNNIGSKSVHWYQQKPGQAPVLVVYDDS

DRPSGIPERFSGSNSGNTATLTISRVEAGDEADYYCQVWDSSNDHVVFGGG

TKLTVL.

In an embodiment, the targeting moiety comprises the anti-PD-L1 antibody 2.7A40PT, or fragments thereof, as disclosed in WO 2011/066389, U.S. Pat. No. 8,779,108, and US2014/0356353, and US2014/0356353, the entire disclosures of which are hereby incorporated by reference. In illustrative embodiments, 2.7A40PT or an antigen-binding fragment thereof for use in the methods provided herein comprises a heavy chain variable region comprising the amino acid sequence of:

SEQ ID No: 62 of WO 2011/066389 (SEQ ID NO: 96):
EVQLVESGGGLVKPGGSLRLSCAASGFTFSTYSMNWVRQAPGKGLEWVSSI

SSSGDYIYYADSVKGRFTISRDNAKNSLYLQMNSLRAEDTAVYYCARDLVT

SMVAFDYWGQGTLVTVSS;

and/or a light chain variable region comprising the amino acid sequence of:

SEQ ID No: 67 of WO 2011/066389 (SEQ ID NO: 97):
SYELTQPPSVSVSPGQTARITCSGDALPQKYVFWYQQKSGQAPVLVIYEDS

KRPSGIPERFSGSSSGTMATLTISGAQVEDEADYYCYSTDRSGNHRVFGGG

TKLTVL.

In an embodiment, the targeting moiety comprises the anti-PD-L1 antibody 2.14H90PT, or fragments thereof, as disclosed in WO 2011/066389, U.S. Pat. No. 8,779,108, and US2014/0356353, the entire disclosures of which are hereby incorporated by reference. In illustrative embodiments, 2.14H90PT or an antigen-binding fragment thereof for use in the methods provided herein comprises a heavy chain variable region comprising the amino acid sequence of:

SEQ ID No: 72 of WO 2011/066389 (SEQ ID NO: 98):
EVQLVESGGGLVQPGGSLRLSCAASGFTFSRYWMSWVRQAPGKGLEWVANI

KQDGSEKYYVDSVKGRFTISRDNAKNSLYLQMNSLRAEDTAVYYCAREGGW

FGELAFDYWGQGTLVTVSS;

and/or a light chain variable region comprising the amino acid sequence of:

SEQ ID No: 77 of WO 2011/066389 (SEQ ID NO: 99):
EIVLTQSPGTLSLSPGERATLSCRASQRVSSSYLAWYQQKPGQAPRLLIYD

ASSRATGIPDRFSGSGSGTDFTLTISRLEPEDFAVYYCQQYGSLPWTFGQG

TKVEIK.

In an embodiment, the targeting moiety comprises any one of the anti-PD-L1 antibodies disclosed in WO2016/061142, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 18, 30, 38, 46, 50, 54, 62, 70, and 78 of WO2016/061142:

SEQ ID No: 18 of WO2016/061142 (SEQ ID NO: 100):
QVQLVQSGAEVKKPGASVKVSCKASGYTFTSYWMYWVRQATGQGLEWMGRI

DPNSGSTKYNEKFKNRFTISRDDSKNTAYLQMNSLKTEDTAVYYCARDYRK

GLYAMDYWGQGTTVTVSS;

SEQ ID No: 30 of WO2016/061142 (SEQ ID NO: 101):
EVQLVQSGAEVKKPGATVKISCKVSGYTFTSYWMYWVRQATGQGLEWMGRI

DPNSGSTKYNEKFKNRVTITADKSTSTAYMELSSLRSEDTAVYYCARDYRK

GLYAMDYWGQGTTVTVSS;

SEQ ID No: 38 of WO2016/061142 (SEQ ID NO: 102):
EVQLVQSGAEVKKPGESLRISCKGSGYTFTSYWMYWVRQAPGQGLEWMGRI

DPNSGSTKYNEKFKNRVTISVDTSKNQFSLKLSSVTAADTAVYYCARDYRK

GLYAMDYWGQGTTVTVSS;

SEQ ID No: 46 of WO2016/061142 (SEQ ID NO: 103):
EVQLVQSGAEVKKPGATVKISCKVSGYTFTSYWMYWIRQSPSRGLEWLGRI

DPNSGSTKYNEKFKNRLTISKDTSKNQVVLTMTNMDPVDTATYYCARDYRK

GLYAMDYWGQGTTVTVSS;

SEQ ID No: 50 of WO2016/061142 (SEQ ID NO: 104):
EVQLVQSGAEVKKPGESLRISCKGSGYTFTSYWMYWIRQPPGKGLEWIGRI

DPNSGSTKYNEKFKNRVTITADKSTSTAYMELSSLRSEDTAVYYCARDYRK

GLYAMDYWGQGTTVTVSS;

SEQ ID No: 54 of WO2016/061142 (SEQ ID NO: 105):
QVQLVQSGAEVKKPGASVKVSCKASGYTFTSYWMYWIRQSPSRGLEWLGRI

DPNSGSTKYNEKEKNRFTISRDDSKNTAYLQMNSLKTEDTAVYYCARDYRK

GLYAMDYWGQGTTVTVSS;

-continued

SEQ ID No: 62 of WO2016/061142 (SEQ ID NO: 106):
EVQLVQSGAEVKKPGESLRISCKGSGYTFTSYWMYWVRQARGQRLEWIGRI

DPNSGSTKYNEKFKNRLTISKDTSKNQVVLIMINMDPVDTATYYCARDYRK

GLYAMDYWGQGTTVTVSS;

SEQ ID No: 70 of WO2016/061142 (SEQ ID NO: 107):
QITLKESGPTLVKPTQTLTLICTFSGYTFTSYWMYWVRQAPGKGLEWVSRI

DPNSGSTKYNEKFKNRVTITADKSTSTAYMELSSLRSEDTAVYYCARDYRK

GLYAMDYWGQGTTVTVSS;

SEQ ID No: 78 of WO2016/061142 (SEQ ID NO: 108):
EVQLVQSGAEVKKPGATVKISCKVSGYTFTSYWMYWVRQARGQRLEWIGRI

DPNSGSTKYNEKEKNRFTISRDNSKNTLYLQMNSLRAEDTAVYYCARDYRK

GLYAMDYWGQGTTVTVSS;

and/or a light chain comprising an amino acid sequence selected from SEQ ID Nos: 22, 26, 34, 42, 58, 66, 74, 82, and 86 of WO2016/061142:

SEQ ID No: 22 of WO2016/061142 (SEQ ID NO: 109):
DIVMTQTPLSLPVTPGEPASISCKASQDVGTAVAWYLQKPGQSPQLLIYW

ASTRHTGIPARFSGSGSGTEFTLTISSLQSEDFAVYYCQQYNSYPLTFGQ

GTKVEIK;

SEQ ID No: 26 of WO2016/061142 (SEQ ID NO: 110):
DIQMTQSPSSLSASVGDRVTITCKASQDVGTAVAWYLQKPGQSPQLLIYW

ASTRHTGVPSRFSGSGSGTDFTLTISSLQPEDFATYYCQQYNSYPLTFGQ

GTKVEIK;

SEQ ID No: 34 of WO2016/061142 (SEQ ID NO: 111):
EIVLTQSPDFQSVTPKEKVTITCKASQDVGTAVAWYLQKPGQSPQLLIYW

ASTRHTGVPDRFSGSGSGTDFTLKISRVEAEDVGVYYCQQYNSYPLTFGQ

GTKVEIK;

SEQ ID No: 42 of WO2016/061142 (SEQ ID NO: 112):
EIVLTQSPDFQSVTPKEKVTITCKASQDVGTAVAWYLQKPGQSPQLLIYW

ASTRHTGVPSRFSGSGSGTDFTFTISSLQPEDIATYYCQQYNSYPLTFGQ

GTKVEIK.

SEQ ID No: 58 of WO2016/061142 (SEQ ID NO: 113):
EIVLTQSPATLSLSPGERATLSCKASQDVGTAVAWYLQKPGQSPQLLIYW

ASTRHIGIPPRFSGSGYGTDFILTINNIESEDAAYYFCQQYNSYPLTEGQ

GTKVEIK;

SEQ ID No: 66 of WO2016/061142 (SEQ ID NO: 114):
DVVMTQSPLSLPVTLGQPASISCKASQDVGTAVAWYQQKPGQAPRLLIYW

ASTRHTGVPSRFSGSGSGTEFTLTISSLQPDDFATYYCQQYNSYPLIFGQ

GTKVEIK;

SEQ ID No: 74 of WO2016/061142 (SEQ ID NO: 115):
DIQMTQSPSSLSASVGDRVTITCKASQDVGTAVAWYQQKPGQAPRLLIYW

ASTRHTGVPSRFSGSGSGTDFTFTISSLQPEDIATYYCQQYNSYPLIFGQ

GTKVEIK;

-continued

SEQ ID No: 82 of WO2016/061142 (SEQ ID NO: 116):
AIQLTQSPSSLSASVGDRVTITCKASQDVGTAVAWYLQKPGQSPQLLIYW

ASTRHTGVPSRFSGSGSGTDFTFTISSLEAEDAATYYCQQYNSYPLTFGQ

GTKVEIK;

SEQ ID No: 86 of WO2016/061142 (SEQ ID NO: 117):
EIVLTQSPDFQSVTPKEKVTITCKASQDVGTAVAWYQQKPGQAPRLLIYW

ASTRHTGVPSRFSGSGSGTEFTLTISSLQPDDFATYYCQQYNSYPLIFGQ

GTKVEIK.

In an embodiment, the targeting moiety comprises any one of the anti-PD-L1 antibodies disclosed in WO2016/022630, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 2, 6, 10, 14, 18, 22, 26, 30, 34, 38, 42, and 46 of WO2016/022630:

SEQ ID No: 2 of WO2016/022630 (SEQ ID NO: 118):
EVKLVESGGGLVKPGGSLKLSCAASGFIFRSYGMSWVRQTPEKRLEWVASI

SSGGSTYYPDSVKGRFTISRDNARNILYLQMSSLRSEDTAMYDCARGYDSG

FAYWGQGTLVTVSE;

SEQ ID No: 6 of WO2016/022630 (SEQ ID NO: 119):
EVKLVESGGGLVKPGGSLKLSCAASGFTFRSYGMSWVRQTPEKRLEWVASI

SSGGTTYYPDSVKGRFIISRDNARNILYLQMSSLRSEDTAMYYCAKGYDSG

FAYWGQGTLVIVSA;

SEQ ID No: 10 of WO2016/022630 (SEQ ID NO: 120):
QVQLKQSGPGLVQPSQSLSITCTVSGESLTTYGVHWVRQSPGKGLEWLGVI

WRGVTTDYNAAFMSRLTITKDNSKSQVFFKMNSLQANDTAIYYCARLGFYA

MDYWGQGTSVTVSS;

SEQ ID No: 14 of WO2016/022630 (SEQ ID NO: 121):
QVQLKQSGPGLVQPSQSLSITCTVSGFSLTSYGVHWVRQSPGKGLEWLGVI

WSGGVTDYNAAFISRLSISKDNSKSQVFFKMNSLQANDTAIYYCARLGFYA

MDYWGQGTSVTVSS;

SEQ ID No: 18 of WO2016/022630 (SEQ ID NO: 122):
EVKLFESGGGLVQPGGSLKLSCVASGEDFSTYWMHWVRQAPGQGLEWIGQI

NPDSTTINYAPSLKDRFIISRDNAKNTLFLQMSKVRSEDTALYYCAKPGDY

GYDFDCWGQGTTLTVSS;

SEQ ID No: 22 of WO2016/022630 (SEQ ID NO: 123):
EVQLQESGPSLVKPSQTLSLTCSVTGDSITSGYWNWIRKFPGNKLEYMGYI

SYSGSTYYNPSLKSRISITRDTSKNQYYLQLNSVTTEDTATYYCARSLLWF

STGFAYWGQGTLVTVSA;

SEQ ID No: 26 of WO2016/022630 (SEQ ID NO: 124):
QVQLKQSGPGLVQPSQSLSITCTVSGFSLTSYGVHWVRQSPGKGLEWLGVI

WSGGITDYNAAFKSRLSISKDNSKSQVFFKMNSLQANDTAIYFCARLGFYA

MDYWGQGTSVTVSS;

SEQ ID No: 30 of WO2016/022630 (SEQ ID NO: 125):
EVKLVESGGGLVKPGGSLKLSCAASGFTFRSYGMSWARQIPEKRLEWVASI

SSGGTTYYLGSVQGRFTISRDNARNILYLQMSSLRSEDTAMYYCARGYDAG

FAYWGQGTLVSVSE;

-continued

SEQ ID No: 34 of WO2016/022630 (SEQ ID NO: 126):
EVQLQESGPSLVKPSQTLSLTCSVTGDSITSGYWTWIRKFPGNKLEYMGYI

SYTGSTYYNPSLKSRISISRDTSKSQYYLQLNSVITEDTATYYCARQRDWL

GFAYWGQGTLVTVSA;

SEQ ID No: 38 of WO2016/022630 (SEQ ID NO: 127):
EEKLVESGGGLVKPGGSLKLSCAASGFSFSSYGMSWVRQTPEKRLEWVASI

SSGGSIYYPDSVKGRFTISRDNARNILYLQMSSLRSEDTAMYYCARGYDAG

FAFWGQGTLVTASA;

SEQ ID No: 42 of WO2016/022630 (SEQ ID NO: 128):
QITLKESGPTLVKPTQTLTLTCTVSGESLSTYGVHWIRQPPGKALEWLGVI

WRGVTTDYNAAFMSRLTITKDNSKNQVVLIMNNMDPVDTATYYCARLGFYA

MDYWGQGTLVTVSS;

SEQ ID No: 46 of WO2016/022630 (SEQ ID NO: 129):
EVQLVESGGGLVKPGGSLRLSCAASGFIFRSYGMSWVRQAPGKGLEWVASI

DSSGGSTYYPSVKGRFTISRDNAKNSLYLQMNSLRAEDTAVYDCARGYDSG

FAYWGQGTLVTVSS;

and/or a light chain comprising an amino acid sequence selected from SEQ ID Nos: 4, 8, 12, 16, 20, 24, 28, 32, 36, 40, 44, and 48 of WO2016/022630:

SEQ ID No: 4 of WO2016/022630 (SEQ ID NO: 130):
DIVLTQSPASLAVSLGQRATISCRASQSVSTSSSSFMHWYQQKPGQPPKL

LIKYASNLESGVPARFSGSGSGTDFTLNIHPVEEEDTATYYCQHSWEIPY

TFGGGTKLEIKR;

SEQ ID No: 8 of WO2016/022630 (SEQ ID NO: 131):
DIVLTQSPPSLAVSLGQRATISCRASQSVSTSSSSYMHWYQQKPGQPPKL

LIKYASNLESGVPARFSGSGSGTDFTLNIHPVEEEDTATYYCQHSWEIPY

TFGGGTKLEIK;

SEQ ID No: 12 of WO2016/022630 (SEQ ID NO: 132):
SIVMTQTPKFLLVSAGDRVTITCKASQSVSNDVAWYQQKPGQSPKLLIYY

AANRYTGVPDRFTGSGYGTDFTFTISIVQAEDLAVYFCQQDYTSPYTFGG

GTKLEIK;

SEQ ID No: 16 of WO2016/022630 (SEQ ID NO: 133):
SIVMTQTPKFLLVSAGDRVTITCKASQSVSNDVGWYQQKPGQSPKLLIYY

ASNRYSGVPDRFTGSGYGTDFTFTISTVQAEDLAVYFCQQDYTSPYTFGG

GTKLEIK;

SEQ ID No: 20 of WO2016/022630 (SEQ ID NO: 134):
DVLMTQTPLYLPVSLGDQASISCRSSQIIVHSNANTYLEWELQKPGQSPK

LLIYKVSNRFSGVPDRFSGSGSGTDFTLKISRVEAEDLGVYYCFQGSHVP

YTFGGGTKLEIK;

SEQ ID No: 24 of WO2016/022630 (SEQ ID NO: 135):
QIVLTQSPAIMSASPGEKVTLTCSASSSVSSSYLYWNQQKPGSSPKVWIY

NTSNLASGVPARFSGSGSGTSYSLTISSMEAEDAASYFCHQWRSYPPTLG

AGTKLELK;

-continued

SEQ ID No: 28 of WO2016/022630 (SEQ ID NO: 136):
QIVLTQSPAIMSASPGEKVTMTCSANSSVSYMHWYQQKSGTSPKRWIYDT

SKLASGVPARFSGSGSGTSYSLTISSMGAEDAATYYCQQWSSNPWTFGGG

TKLEIK;

SEQ ID No: 32 of WO2016/022630 (SEQ ID NO: 137):
DIVLTQSPASLAVSLGQRATISCRASQSVSTSSYSYMHWYQQKPGQPPKL

LIKYASNLESGVPARFSGSGSGTDFTLNIHPVEEEDTATYYCQNSWEIPY

TFGGGTKLEIK;

SEQ ID No: 36 of WO2016/022630 (SEQ ID NO: 138):
DIVMTQTPSSLAVSLGEKVTMSCKSSQSLLYSSNQKNSLAWYQQKPGQSP

KLLIYWASNRESGVPDRFTGSSSGTDFTLTISSVKAEDLAVYYCQQYYSY

PLTFGAGTKLELK;

SEQ ID No: 40 of WO2016/022630 (SEQ ID NO: 139):
DIVLTQSPASLAVSLGQRATISCRASQSVSTSSYSYVHWYQQKPGQPPKL

LIKYASNLESGVPARFSGSGSGTDFTLNIHPVEEEDTATYYCQHSWEIPY

TFGGGTKLEIK;

SEQ ID No: 44 of WO2016/022630 (SEQ ID NO: 140):
DIQMTQSPSSLSASVGDRVTITCKASQSVSNDVAWYQQKPGKAPKLLIYY

AANRYTGVPDRFSGSGYGTDFTFTISSLQPEDIATYFCQQDYTSPYTFGQ

GTKLEIK;

SEQ ID No: 48 of WO2016/022630 (SEQ ID NO: 141):
DIVLTQSPASLAVSPGQRATITCRASQSVSTSSSSFMHWYQQKPGQPPKL

LIKYASNLESGVPARFSGSGSGTDFTLTINPVEANDTANYYCQHSWEIPY

TFGQGTKLEIK.

In an embodiment, the targeting moiety comprises any one of the anti-PD-L1 antibodies disclosed in WO2015/112900, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 38, 50, 82, and 86 of WO 2015/112900:

SEQ ID No: 38 of WO2015/112900 (SEQ ID NO: 142):
EVQLVQSGAEVKKPGESLRISCKGSGYTFTTYWMHWVRQATGQGLEWMGNI

YPGTGGSNFDEKFKNRVTITADKSTSTAYMELSSLRSEDTAVYYCTRWTTG

TGAYWGQGTTVTVSS;

SEQ ID No: 50 of WO 2015/112900 (SEQ ID NO: 143):
EVQLVQSGAEVKKPGESLRISCKGSGYTFTTYWMHWIRQSPSRGLEWLGNI

YPGTGGSNFDEKFKNRFTISRDNSKNTLYLQMNSLRAEDTAVYYCTRWTTG

TGAYWGQGTTVTVSS;

SEQ ID No: 82 of WO 2015/112900 (SEQ ID NO: 144):
QVQLVQSGAEVKKPGASVKVSCKASGYTFTTYWMHWIRQSPSRGLEWLGNI

YPGTGGSNFDEKFKNRFTISRDNSKNTLYLQMNSLRAEDTAVYYCTRWTTG

TGAYWGQGTTVTVSS;

SEQ ID No: 86 of WO 2015/112900 (SEQ ID NO: 145):
EVQLVQSGAEVKKPGESLRISCKGSGYTFTTYWMHWVRQAPGQGLEWMGNI

YPGTGGSNFDEKFKNRFTISRDNSKNTLYLQMNSLRAEDTAVYYCTRWTTG

TGAYWGQGTTVTVSS;

and/or a light chain comprising an amino acid sequence selected from SEQ ID Nos: 42, 46, 54, 58, 62, 66, 70, 74, and 78 of WO 2015/112900:

SEQ ID No: 42 of WO2015/112900 (SEQ ID NO: 146):
EIVLTQSPATLSLSPGERATLSCKSSQSLLDSGNQKNFLTWYQQKPGQAP

RLLIYWASTRESGVPSRFSGSGSGTEFTLTISSLQPDDFATYYCQNDYSY

PYTFGQGTKVEIK;

SEQ ID No: 46 of WO2015/112900 (SEQ ID NO: 147):
DIQMTQSPSSLSASVGDRVTITCKSSQSLLDSGNQKNFLTWYQQKPGQAP

RLLIYWASTRESGIPPRFSGSGYGTDFTLTINNIESEDAAYYFCQNDYSY

PYTFGQGTKVEIK;

SEQ ID No: 54 of WO2015/112900 (SEQ ID NO: 148):
EIVLTQSPATLSLSPGERATLSCKSSQSLLDSGNQKNFLTWYQQKPGKAP

KLLIYWASTRESGVPSRFSGSGSGTDFTFTISSLQPEDIATYYCQNDYSY

PYTFGQGTKVEIK;

SEQ ID No: 58 of WO2015/112900 (SEQ ID NO: 149):
DIVMTQTPLSLPVTPGEPASISCKSSQSLLDSGNQKNFLTWYQQKPGQAP

RLLIYWASTRESGVPSRFSGSGSGTDFTFTISSLEAEDAATYYCQNDYSY

PYTFGQGTKVEIK;

SEQ ID No: 62 of WO2015/112900 (SEQ ID NO: 150):
EIVLTQSPATLSLSPGERATLSCKSSQSLLDSGNQKNFLTWYQQKPGKAP

KLLIYWASTRESGVPSRFSGSGSGTDFTFTISSLEAEDAATYYCQNDYSY

PYTFGQGTKVEIK;

SEQ ID No: 66 of WO2015/112900 (SEQ ID NO: 151):
EIVLTQSPDFQSVTPKEKVTITCKSSQSLLDSGNQKNFLTWYQQKPGQAP

RLLIYWASTRESGVPSRFSGSGSGTDFTFTISSLEAEDAATYYCQNDYSY

PYTFGQGTKVEIK;

SEQ ID No: 70 of WO2015/112900 (SEQ ID NO: 152):
EIVLTQSPATLSLSPGERATLSCKSSQSLLDSGNQKNFLTWYQQKPGQAP

RLLIYWASTRESGVPSRFSGSGSGTDFTFTISSLEAEDAATYYCQNDYSY

PYTFGQGTKVEIK;

SEQ ID No: 74 of WO2015/112900 (SEQ ID NO: 153):
DIQMTQSPSSLSASVGDRVTITCKSSQSLLDSGNQKNFLTWYLQKPGQSP

QLLIYWASTRESGVPSRFSGSGSGTDFTFTISSLEAEDAATYYCQNDYSY

PYTFGQGTKVEIK;

SEQ ID No: 78 of WO2015/112900 (SEQ ID NO: 154):
DVVMTQSPLSLPVTLGQPASISCKSSQSLLDSGNQKNFLTWYQQKPGKAP

KLLIYWASTRESGVPSRFSGSGSGTDFTFTISSLEAEDAATYYCQNDYSY

PYTFGQGTKVEIK.

In an embodiment, the targeting moiety comprises any one of the anti-PD-L1 antibodies disclosed in WO 2010/077634 and U.S. Pat. No. 8,217,149, the entire disclosures of which are hereby incorporated by reference. In illustrative embodiments, the anti-PD-L1 antibody or an antigen-binding fragment thereof for use in the methods provided herein comprises a heavy chain region comprising the amino acid sequence of:

SEQ ID No: 20 of WO 2010/077634 (SEQ ID NO: 155):
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSA;

and/or a light chain variable region comprising the amino acid sequence of:

SEQ ID No: 21 of WO 2010/077634 (SEQ ID NO: 156):
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR.

In an embodiment, the targeting moiety comprises any one of the anti-PD-L1 antibodies obtainable from the hybridoma accessible under CNCM deposit numbers CNCM I-4122, CNCM I-4080 and CNCM I-4081 as disclosed in US 20120039906, the entire disclosures of which are hereby incorporated by reference.

In an embodiment, the targeting moiety comprises a VHH directed against PD-L1 as disclosed, for example, in U.S. Pat. No. 8,907,065 and WO 2008/071447, the entire disclosures of which are hereby incorporated by reference. In illustrative embodiments, the VHHs against PD-L1 comprise SEQ ID NOS: 394-399 of U.S. Pat. No. 8,907,065:

SEQ ID No: 394 of U.S. Pat No. 8,907,065
(SEQ ID NO: 157):
EVQLVESGGGLVQPGGSLRLSCAASGFTLDYYAIGWFRQAPGKEREWASS

ISSSDGSTYYADSVKGRFTISRDNAKNTVFLQMNSLKPEDTAVYSCAASQ

APITIATMMKPFYDYWGQGTQVTVSS;

SEQ ID No: 395 of U.S. Pat No. 8,907,065
(SEQ ID NO: 158):
EVQLVESGGGLVQPGGSLRLSCAASGFTLDYYAKCWFRQAPGKEREWVSC

ISSSDGSTYYADSVKGRFTISRDNAKNTVYLQMNSLKPEDTAVYFCAARH

GGPLTVEYFFDYWGQGTQVTVSS;

SEQ ID No: 396 of U.S. Pat No. 8,907,065
(SEQ ID NO: 159):
EVQLVESGGGLVQPGGSLRLSCAASGFTFDYYAIGWFRQAPGKAREGVSC

ISGGDNSTYYADSVKGRFTISRDNAKNTVYLQMNSLKPEDTAVYYCATGG

WKYCSGYDPEYIYWGQGTQVTVSS;

SEQ ID No: 397 of U.S. Pat No. 8,907,065
(SEQ ID NO: 160):
EVQLVESGGGLVQAGGSLRLSCAASGSTFSQYDVGWYRQAPGKQRELVA

FSSSGGRTIYPDSVKGRFTFSRDNIKNIVYLQMTSLKPEDTAVYYCKIDW

YLNSYWGQGTQVTVSS;

SEQ ID No: 398 of U.S. Pat No. 8,907,065
(SEQ ID NO: 161):
EVQLVESGGGLVQAGGSLRLSCAASGVDASNSAMGWYRQAPGKQREWVAR

ITGGGLIAYTDSVKGRFTISRDNAKSTVYLQMNSLEPEDTAVYYCNTINS

RDGWGQGTQVTVSS;

-continued

SEQ ID No: 399 of U.S. Pat No. 8,907,065
(SEQ ID NO: 162):
EVQLVESGGGLVQAGGSLTISCAASGITFSDSIVSWYRRARGKQREWVAG

ISNGGTTKYAESVLGRFTISRDNAKNNVYLQMNGLNPEDTAVYLCKVRQY

WGQGTQVTVSS.

In various embodiments, the present chimeric protein has one targeting moiety directed against PD-L2. In some embodiments, the chimeric protein include a targeting moiety which selectively bind a PD-L2 polypeptide. In some embodiments, the chimeric protein comprises an antibody, an antibody derivative or format, a peptide or polypeptide, or a fusion protein that selectively binds a PD-L2 polypeptide.

In an embodiment, the targeting moiety comprises a VHH directed against PD-L2 as disclosed, for example, in U.S. Pat. No. 8,907,065 and WO 2008/071447, the entire disclosures of which are hereby incorporated by reference. In illustrative embodiments, the VHHs against PD-1 comprise SEQ ID Nos: 449-455 of U.S. Pat. No. 8,907,065:

SEQ ID No: 449 of U.S. Pat No. 8,907,065
(SEQ ID NO: 163):
EVQLVESGGGLVQAGGSLRLSCAASESTVLINAMGWYRQAPGKQRELVAS

ISSGGSTNYADSVKGRFTISRDNAKNTVYLQMNSLKPEDTAVYYCNADVY

PQDYGLGYVEGKVYYGHDYWGTGTLVTVSS;

SEQ ID No: 450 of U.S. Pat No. 8,907,065
(SEQ ID NO: 164):
EVQLVESGGGLVQAGGSLRLSCAASGSTFSNYVSNYAMGWGRQAPGTQ

RELVASISNGDTTNYADSVKGRFTISRDNAKNTVYLQMNSLKPEDTAVYY

CFEHQVAGLTWGQGTQVTVSS;

SEQ ID No: 451 of U.S. Pat No. 8,907,065
(SEQ ID NO: 165):
EVQLVESGGGLVQAGGSLRLSCVASGXALKIXVMGWYRQAPGKQRELV

AAITSGGRTNYSDSVKGRFTISGDNAXNTVYLQMNSLKSEDTAVYYCRE

WNSGYPPVDYWGQGTQVTVSS;

SEQ ID No: 452 of U.S. Pat No. 8,907,065
(SEQ ID NO: 166):
EVQLVESGGGLVQAGGSLRLSCAASGRTFSSGTMGWFRRAPGKEREFV

ASIPWSGGRTYYADSVKDRFTISRDNAQNTVFLQMNSLKPEDTAVYYCAF

KERSTGWDFASWGQGIQVTVSS;

SEQ ID No: 453 of U.S. Pat No. 8,907,065
(SEQ ID NO: 167):
EVQLVESGGGLVQTGGSLRLSCAASGFTLDYYGIGWFRQAPGKEREGVS

FISGSDGSTYYAESVKGRFTISRDKAKNTVYLQMNSLKPEDTAVYYCAAD

PWGPPSIATMTSYEYKHWGQGTQVTVSS;

SEQ ID No: 454 of U.S. Pat No. 8,907,065
(SEQ ID NO: 168):
EVQLVESGGGLVQPGGSLRLSCAASGFTFSTYTMIWLRRAPGKGFEWV

STIDKDGNTNYVDSVKGRFAVSRDNTKNTLYLQMNSLKPEDTAMYYCTK

HGSSARGQGTRVTVSS;

-continued

```
SEQ ID No: 455 of U.S. Pat No. 8,907,065
(SEQ ID NO: 169):
EVQLVESGGGLVEPGGSLRLSCVASGFTFSSYDMSWVRQAPGKGLE

WVSTINSGGGITYRGSVKGRFTISRDNAKNTLYLQMNSLKPEDTAVYY

CENGGSSYRRGQGTQVTVSS.
```

In an embodiment, the targeting moiety comprises any one of the anti-PD-L2 antibodies disclosed in US2011/0271358 and WO2010/036959, the entire contents of which are hereby incorporated by reference. In illustrative embodiments, the antibody or an antigen-binding fragment thereof for use in the methods provided herein comprises a heavy chain comprising an amino acid sequence selected from SEQ ID Nos: 43-47 of US2011/0271358:

```
SEQ ID No: 43 of US2011/0271358 (SEQ ID NO 170):
QVQLVQSGAELKKPGASVKMSCKASGYTFTGYTMHWVKQAPGQGLEWIG

YINPRSGYTEYNQKFKDRTTLTADKSTSTAYMELSSLRSEDSAVYYCAR

PWFAYWGQGTLVTVSS;

SEQ ID No: 44 of US2011/0271358 (SEQ ID NO: 171):
QVQLVQSGAEVKKPGASVKMSCKASGYTFTGYTMHWVKQAPGQGLEWIG

YINPRSGYTEYNQKFKDRTTLTADKSTSTAYMELSSLRSEDTAVYYCAR

PWFAYWGQGTLVTVSS;

SEQ ID No: 45 of US2011/0271358 (SEQ ID NO: 172):
QVQLVQSGAEVKKPGASVKMSCKASGYTFTGYTMHWVRQAPGQGLEWIG

YINPRSGYTEYNQKFKDRTTLTADKSTSTAYMELSSLRSEDTAVYYCAR

PWFAYWGQGTLVTVSS;

SEQ ID No: 46 of US2011/0271358 (SEQ ID NO: 173):
QVQLVQSGAEVKKPGASVKVSCKASGYTFTGYTMHWVRQAPGQGLEWIG

YINPRSGYTEYNQKFKDRTTLTADKSTSTAYMELSSLRSEDTAVYYCAR

PWFAYWGQGTLVTVSS;

SEQ ID No: 47 of US2011/0271358 (SEQ ID NO: 174):
QVQLVQSGAEVKKPGASVKVSCKASGYTFTGYTMHWVRQAPGQGLEWIG

YINPRSGYTEYNQKFKDRTTITADKSTSTAYMELSSLRSEDTAVYYCAR

PWFAYWGQGTLVTVSS;
```

and/or a light chain comprising an amino acid sequence selected from SEQ ID Nos: 4851 of US2011/0271358:

```
SEQ ID No: 48 of US2011/0271358 (SEQ ID NO: 175):
DIVMTQSPASLTVTPGEKVTITCKSSQSLLNSGNQKNYLTWYQQKPGQPP
KLLIYWASTRESGVPDRFTGSGSGTDFTLTISSLQAEDVAVYYCQNDYSY
PLTFGQGTKLEIK;

SEQ ID No: 49 of US2011/0271358 (SEQ ID NO: 176):
DIVMTQSPASLSVTPGEKVTITCKSSQSLLNSGNQKNYLTWYQQKPGQPP
KLLIYWASTRESGVPDRFTGSGSGTDFTLTISSLQAEDVAVYYCQNDYSY
PLTFGQGTKLEIK;

SEQ ID No: 50 of US2011/0271358 (SEQ ID NO: 177):
DIVMTQSPAFLSVTPGEKVTITCKSSQSLLNSGNQKNYLTWYQQKPGQPP
KLLIYWASTRESGVPDRFTGSGSGTDFTLTISSLQAEDVAVYYCQNDYSY
PLTFGQGTKLEIK;

SEQ ID No: 51 of US2011/0271358 (SEQ ID NO: 178):
DIVMTQSPAFLSVTPGEKVTITCKSSQSLLNSGNQKNYLTWYQQKPGQPP
KLLIYWASTRESGVPDRFSGSGSGTDFTLTISSLQAEDVAVYYCQNDYSY
PLTFGQGTKLEIK.
```

In various embodiments, the targeting moieties of the invention may comprise a sequence that targets PD-1, PD-1, and/or PD-L2 which is at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or 100% identical to any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, about 99% or about 100% sequence identity with any of the sequences disclosed herein).

In various embodiments, the targeting moieties of the invention may comprise any combination of heavy chain, light chain, heavy chain variable region, light chain variable region, complementarity determining region (CDR), and framework region sequences that target PD-1, PD-L1, and/or PD-L2 as disclosed herein.

Additional antibodies, antibody derivatives or formats, peptides or polypeptides, or fusion proteins that selectively bind or target PD-1, PD-L1 and/or PD-L2 are disclosed in WO 2011/066389, US 2008/0025980, US 2013/0034559, U.S. Pat. No. 8,779,108, US 2014/0356353, U.S. Pat. No. 8,609,089, US 2010/028330, US 2012/0114649, WO 2010/027827, WO 2011/066342, U.S. Pat. No. 8,907,065, WO 2016/062722, WO 2009/101611, WO2010/027827, WO 2011/066342, WO 2007/005874, WO 2001/014556, US2011/0271358, WO 2010/036959, WO 2010/077634, U.S. Pat. No. 8,217,149, US 2012/0039906, WO 2012/145493, US 2011/0318373, U.S. Pat. No. 8,779,108, US 20140044738, WO 2009/089149, WO 2007/00587, WO 2016061142, WO 2016,02263, WO 2010/077634, and WO 2015/112900, the entire disclosures of which are hereby incorporated by reference.

Modified Signaling Agents

In one aspect, the present invention provides a chimeric protein that includes a signaling agent (for instance, an immune-modulating agent). In various embodiments, the signaling agent is modified to have reduced activity. In some embodiments, the signaling agent is modified to have reduced affinity for one or more of its receptors which allows for attenuation of activity and/or prevents non-specific signaling or undesirable sequestration of the chimeric protein. In various embodiments, the activity of the modified signaling agent is restored in the context of the chimeric protein which further comprises a targeting moiety that targets specific cell types. Particularly, the activity of the modified signaling agent is restored towards targeted cells but not towards non-targeted cells. Accordingly, in various embodiments, the chimeric proteins of the invention offer therapeutic advantages such as enhanced specificity and efficacy at targeted cells as well as reduced side effects including lower systemic toxicity.

In various embodiments, the signaling agent is selected from modified versions of an immune-modulating agent, e.g. one or more of an interleukin, interferon, and tumor necrosis factor.

In some embodiments, the signaling agent is a modified version of an interleukin, including for example IL-1; IL-2; IL-3; IL-4; IL-5; IL-6; IL-7; IL-8; IL-9; IL-10; IL-11; IL-12; IL-13; IL-14; IL-15; IL-16; IL-17; IL-18; IL-19; IL-20; IL-21; IL-22; IL-23; IL-24; IL-25; IL-26; IL-27; IL-28; IL-29; IL-30; IL-31; IL-32; IL-33; IL-35; IL-36 or a fragment, variant, analogue, or family-member thereof.

In some embodiments, the signaling agent is a modified version of an interferon such as interferon types I, II, and III. Illustrative interferons, include for example, interferon-α-1, 2, 4, 5, 6, 7, 8, 10, 13, 14, 16, 17, and 21, interferon-β and interferon-γ, interferon κ, interferon ε, interferon τ, and interferon ω.

In some embodiments, the signaling agent is a modified version of a tumor necrosis factor (TNF) or a protein in the TNF family, including but not limited to, TNF-α, TNF-β, LT-β, CD40L, CD27L, CD30L, FASL, 4-1BBL, OX40L, and TRAIL.

In various embodiments, the signaling agent is a modified (e.g. mutant) form of the signaling agent having one or more mutations. In various embodiments, the mutations allow for the modified signaling agent to have one or more of attenuated activity such as one or more of reduced binding affinity, reduced endogenous activity, and reduced specific bioactivity relative to unmodified or unmutated, i.e. the wild type form of the signaling agent (e.g. comparing the same signaling agent in a wild type form versus a modified (e.g. mutant) form). In some embodiments, the mutations which attenuate or reduce binding or affinity include those mutations which substantially reduce or ablate binding or activity. In some embodiments, the mutations which attenuate or reduce binding or affinity are different than those mutations which substantially reduce or ablate binding or activity. Consequentially, in various embodiments, the mutations allow for the signaling agent to be more safe, e.g. have reduced systemic toxicity, reduced side effects, and reduced off-target effects relative to unmutated, i.e. wild type, signaling agent (e.g. comparing the same signaling agent in a wild type form versus a modified (e.g. mutant) form). As described herein, the signaling agent may have improved safety due to one of more modifications, e.g. mutations. In various embodiments, improved safety means that the present chimeric protein provides lower toxicity (e.g. systemic toxicity and/or tissue/organ-associated toxicities); and/or lessened or substantially eliminated side effects; and/or increased tolerability, lessened or substantially eliminated adverse events; and/or reduced or substantially eliminated off-target effects; and/or an increased therapeutic window.

In various embodiments, the signaling agent is modified to have one or more mutations that reduce its binding affinity or activity for one or more of its receptors. In some embodiments, the signaling agent is modified to have one or more mutations that substantially reduce or ablate binding affinity or activity for the receptors. In some embodiments, the activity provided by the wild type signaling agent is agonism at the receptor (e.g. activation of a cellular effect at a site of therapy). For example, the wild type signaling agent may activate its receptor. In such embodiments, the mutations result in the modified signaling agent to have reduced or ablated activating activity at the receptor. For example, the mutations may result in the modified signaling agent to deliver a reduced activating signal to a target cell or the activating signal could be ablated. In some embodiments, the activity provided by the wild type signaling agent is antagonism at the receptor (e.g. blocking or dampening of a cellular effect at a site of therapy). For example, the wild type signaling agent may antagonize or inhibit the receptor. In these embodiments, the mutations result in the modified signaling agent to have a reduced or ablated antagonizing activity at the receptor. For example, the mutations may result in the modified signaling agent to deliver a reduced inhibitory signal to a target cell or the inhibitory signal could be ablated. In various embodiments, the signaling agent is antagonistic due to one or more mutations, e.g. an agonistic signaling agent is converted to an antagonistic signaling agent (e.g. as described in WO 2015/007520, the entire contents of which are hereby incorporated by reference) and, such a converted signaling agent, optionally, also bears one or more mutations that reduce its binding affinity or activity for one or more of its receptors or that substantially reduce or ablate binding affinity or activity for one or more of its receptors. In some embodiments, the reduced affinity or activity at the receptor is restorable by attachment with the targeting moiety. In other embodiments, the reduced affinity or activity at the receptor is not substantially restorable by attachment with the targeting moiety.

In various embodiments, the chimeric proteins of the present invention reduce off-target effects because their signaling agents have mutations that weaken or ablate binding affinity or activity at a receptor. In various embodiments, this reduction in side effects is observed relative with, for example, the wild type signaling agents. In various embodiments, the signaling agent is active on target cells because the targeting moiety compensates for the missing/insufficient binding (e.g., without limitation and/or avidity) required for substantial activation. In various embodiments, the modified signaling agent is substantially inactive en route to the site of therapeutic activity and has its effect substantially on specifically targeted cell types which greatly reduces undesired side effects.

In some embodiments, the signaling agent may include one or more mutations that attenuate or reduce binding or affinity for one receptor (i.e., a therapeutic receptor) and one or more mutations that substantially reduce or ablate binding or activity at a second receptor. In such embodiments, these mutations may be at the same or at different positions (i.e., the same mutation or multiple mutations). In some embodiments, the mutation(s) that reduce binding and/or activity at one receptor is different than the mutation(s) that substantially reduce or ablate at another receptor.

In some embodiments, the mutation(s) that reduce binding and/or activity at one receptor is the same as the mutation(s) that substantially reduce or ablate at another receptor. In some embodiments, the present chimeric proteins have a modified signaling agent that has both mutations that attenuate binding and/or activity at a therapeutic receptor and therefore allow for a more controlled, on-target therapeutic effect (e.g. relative wild type signaling agent) and mutations that substantially reduce or ablate binding and/or activity at another receptor and therefore reduce side effects (e.g. relative to wild type signaling agent).

In some embodiments, the substantial reduction or ablation of binding or activity is not substantially restorable with a targeting moiety. In some embodiments, the substantial reduction or ablation of binding or activity is restorable with a targeting moiety. In various embodiments, substantially reducing or ablating binding or activity at a second receptor also may prevent deleterious effects that are mediated by the other receptor. Alternatively, or in addition, substantially reducing or ablating binding or activity at the other receptor causes the therapeutic effect to improve as there is a reduced or eliminated sequestration of the therapeutic chimeric proteins away from the site of therapeutic action. For instance, in some embodiments, this obviates the need of high doses of the present chimeric proteins that compensate for loss at the other receptor. Such ability to reduce dose further provides a lower likelihood of side effects.

In various embodiments, the modified signaling agent comprises one or more mutations that cause the signaling agent to have reduced, substantially reduced, or ablated affinity, e.g. binding (e.g. $K_D$) and/or activation (for instance, when the modified signaling agent is an agonist of its receptor, measurable as, for example, $K_A$ and/or $EC_{50}$) and/or inhibition (for instance, when the modified signaling agent is an antagonist of its receptor, measurable as, for example, $K_I$ and/or $IC_{50}$), for one or more of its receptors. In various embodiments, the reduced affinity at the signaling agent's receptor allows for attenuation of activity (inclusive of agonism or antagonism). In such embodiments, the modified signaling agent has about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, about 95%, or about 10%-20%, about 20%-40%, about 50%, about 40%-60%, about 60%-80%, about 80%-100% of the affinity for the receptor relative to the wild type signaling agent. In some embodiments, the binding affinity is at least about 2-fold lower, about 3-fold lower, about 4-fold lower, about 5-fold lower, about 6-fold lower, about 7-fold lower, about 8-fold lower, about 9-fold lower, at least about 10-fold lower, at least about 15-fold lower, at least about 20-fold lower, at least about 25-fold lower, at least about 30-fold lower, at least about 35-fold lower, at least about 40-fold lower, at least about 45-fold lower, at least about 50-fold lower, at least about 100-fold lower, at least about 150-fold lower, or about 10-50-fold lower, about 50-100-fold lower, about 100-150-fold lower, about 150-200-fold lower, or more than 200-fold lower relative to the wild type signaling agent.

In embodiments wherein the chimeric protein has mutations that reduce binding at one receptor and substantially reduce or ablate binding at a second receptor, the attenuation or reduction in binding affinity of a modified signaling agent for one receptor is less than the substantial reduction or ablation in affinity for the other receptor. In some embodiments, the attenuation or reduction in binding affinity of a modified signaling agent for one receptor is less than the substantial reduction or ablation in affinity for the other receptor by about 1%, or about 3%, about 5%, about 10%, about 15%, about 20%, about 25%, about 30%, about 35%, about 40%, about 45%, about 50%, about 60%, about 65%, about 70%, about 75%, about 80%, about 85%, about 90%, or about 95%. In various embodiments, substantial reduction or ablation refers to a greater reduction in binding affinity and/or activity than attenuation or reduction.

In various embodiments, the modified signaling agent comprises one or more mutations that reduce the endogenous activity of the signaling agent to about 75%, or about 70%, or about 60%, or about 50%, or about 40%, or about 30%, or about 25%, or about 20%, or about 10%, or about 5%, or about 3%, or about 1%, e.g., relative to the wild type signaling agent In some embodiments, the modified signaling agent comprises one or more mutations that cause the signaling agent to have reduced affinity for its receptor that is lower than the binding affinity of the targeting moiety for its receptor. In some embodiments, this binding affinity differential is between signaling agent/receptor and targeting moiety/receptor on the same cell. In some embodiments, this binding affinity differential allows for the signaling agent, e.g. mutated signaling agent, to have localized, on-target effects and to minimize off-target effects that underlie side effects that are observed with wild type signaling agent. In some embodiments, this binding affinity is at least about 2-fold, or at least about 5-fold, or at least about 10-fold, or at least about 15-fold lower, or at least about 25-fold, or at least about 50-fold lower, or at least about 100-fold, or at least about 150-fold.

Receptor binding activity may be measured using methods known in the art. For example, affinity and/or binding activity may be assessed by Scatchard plot analysis and computer-fitting of binding data (e.g. Scatchard, 1949) or by reflectometric interference spectroscopy under flow through conditions, as described by Brecht et al. (1993), the entire contents of all of which are hereby incorporated by reference.

The amino acid sequences of the wild type signaling agents described herein are well known in the art. Accordingly, in various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the known wild type amino acid sequences of the signaling agents described herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments the modified signaling agent comprises an amino acid sequence that has at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with any of the sequences disclosed herein (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99% sequence identity).

In various embodiments, the modified signaling agent comprises an amino acid sequence having one or more amino acid mutations. In some embodiments, the one or more amino acid mutations may be independently selected from substitutions, insertions, deletions, and truncations.

In some embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In various embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

As described herein, the modified signaling agents bear mutations that affect affinity and/or activity at one or more receptors. In various embodiments, there is reduced affinity and/or activity at a therapeutic receptor, e.g. a receptor through which a desired therapeutic effect is mediated (e.g. agonism or antagonism). In various embodiments, the modified signaling agents bear mutations that substantially reduce or ablate affinity and/or activity at a receptor, e.g. a receptor through which a desired therapeutic effect is not mediated (e.g. as the result of promiscuity of binding).

The receptors of any modified signaling agents, e.g. one of the cytokines, growth factors, and hormones as described herein, are known in the art.

Illustrative mutations which provide reduced affinity and/or activity (e.g. agonistic) at a receptor are found in WO 2013/107791 (e.g. with regard to interferons), WO 2015/007542 (e.g. with regard to interleukins), and WO 2015/007903 (e.g. with regard to TNF), the entire contents of each of which are hereby incorporated by reference.

Illustrative mutations which provide reduced affinity and/or activity (e.g. antagonistic) at a therapeutic receptor are found in WO 2015/007520, the entire contents of which are hereby incorporated by reference.

In some embodiments, the modified signaling agent comprises one or more mutations that cause the signaling agent to have reduced affinity and/or activity for a type I cytokine receptor, a type II cytokine receptor, and a receptor in the Tumor Necrosis Factor Receptor (TNFR) superfamily.

In various embodiments, the receptor for the signaling agent is a Type I cytokine receptor. Type I cytokine receptors are known in the art and include, but are not limited to receptors for IL2 (beta-subunit), IL3, IL4, IL5, IL6, IL7, IL9, IL11, IL12, GM-CSF, G-CSF, LIF, CNTF, and also the receptors for Thrombopoietin (TPO), Prolactin, and Growth hormone. Illustrative type I cytokine receptors include, but are not limited to, GM-CSF receptor, G-CSF receptor, LIF receptor, CNTF receptor, TPO receptor, and type I IL receptors.

In various embodiments, the receptor for the signaling agent is a Type II cytokine receptor. Type II cytokine receptors are multimeric receptors composed of heterologous subunits, and are receptors mainly for interferons. This family of receptors includes, but is not limited to, receptors for interferon-α, interferon-β and interferon-γ, IL10, IL22, and tissue factor. Illustrative type II cytokine receptors include, but are not limited to, IFN-α receptor (e.g. IFNAR1 and IFNAR2), IFN-β receptor, IFN-γ receptor (e.g. IFNGR1 and IFNGR2), and type II IL receptors.

In various embodiments, the receptor for the signaling agent is a TNFR family member. Tumor necrosis factor receptor (TNFR) family members share a cysteine-rich domain (CRD) formed of three disulfide bonds surrounding a core motif of CXXCXXC creating an elongated molecule. Exemplary tumor necrosis factor receptor family members include: CDI 20a (TNFRSFIA), CD 120b (TNFRSFIB), Lymphotoxin beta receptor (LTBR, TNFRSF3), CD 134 (TNFRSF4), CD40 (CD40, TNFRSF5), FAS (FAS, TNFRSF6), TNFRSF6B (TNFRSF6B), CD27 (CD27, TNFRSF7), CD30 (TNFRSF8), CD137 (TNFRSF9), TNFRSFIOA (TNFRSFIOA), TNFRSFIOB, (TNFRSFIOB), TNFRSFIOC (TNFRSFIOC), TNFRSFIOD (TNFRSFIOD), RANK (TNFRSFI IA), Osteoprotegerin (TNFRSFI IB), TNFRSF12A (TNFRSF12A), TNFRSF13B (TNFRSF13B), TNFRSF13C (TNFRSF13C), TNFRSF14 (TNFRSF14), Nerve growth factor receptor (NGFR, TNFRSF16), TNFRSF17 (TNFRSF17), TNFRSF18 (TNFRSF18), TNFRSF19 (TNFRSF19), TNFRSF21 (TNFRSF21), and TNFRSF25 (TNFRSF25).

In an embodiment, the modified signaling agent is interferon α. In such embodiments, the modified IFN-α agent has reduced affinity and/or activity for the IFN-α/β receptor (IFNAR), i.e., IFNAR1 and/or IFNAR2 chains. In some embodiments, the modified IFN-α agent has substantially reduced or ablated affinity and/or activity for the IFN-α/l receptor (IFNAR), i.e., IFNAR1 and/or IFNAR2 chains.

Mutant forms of interferon α such as IFN-α2 are known to the person skilled in the art. In an illustrative embodiment, the modified signaling agent is the allelic form IFN-α2a having the amino acid sequence of:

```
IFN-α2a (SEQ ID NO: 179):
CDLPQTHSLGSRRTLMLLAQMRKISLFSCLKDRHDFGFPQEEFGNQFQK

AETIPVLHEMIQQIFNLFSTKDSSAAWDETLLDKFYTELYQQLNDLEAC

VIQGVGVTETPLMKEDSILAVRKYFQRITLYLKEKKYSPCAWEWRAEIM

RSFSLSTNLQESLRSKE.
```

In an illustrative embodiment, the modified signaling agent is the allelic form IFN-α2b having the amino acid sequence of (which differs from IFN-α2a at amino acid position 23):

```
IFN-α2b (SEQ ID NO: 180):
CDLPQTHSLGSRRTLMLLAQMRRISLFSCLKDRHDFGFPQEEFGNQFQK

AETIPVLHEMIQQIFNLFSTKDSSAAWDETLLDKFYTELYQQLNDLEAC

VIQGVGVTETPLMKEDSILAVRKYFQRITLYLKEKKYSPCAWEWRAEIM

RSFSLSTNLQESLRSKE.
```

In some embodiments, said IFN-α2 mutant (IFN-α2a or IFN-α2b) is mutated at one or more amino acids at positions 144-154, such as amino acid positions 148, 149 and/or 153. In some embodiments, the IFN-α2 mutant comprises one or more mutations selected from L153A, R149A, and M148A. Such mutants are described, for example, in WO2013/107791 and Piehler et al., (2000) J. Biol. Chem, 275:40425-33, the entire contents of all of which are hereby incorporated by reference.

In some embodiments, the IFN-α2 mutants have reduced affinity and/or activity for IFNAR1. In some embodiments, the IFN-α2 mutant comprises one or more mutations selected from F64A, N65A, T69A, L80A, Y85A, and Y89A, as described in WO2010/030671, the entire contents of which is hereby incorporated by reference.

In some embodiments, the IFN-α2 mutant comprises one or more mutations selected from K133A, R144A, R149A, and L153A as described in WO2008/124086, the entire contents of which is hereby incorporated by reference.

In some embodiments, the IFN-α2 mutant comprises a mutation at position R120. In some embodiments, the IFN-α2 mutant comprises one or more mutations selected from R120E and R120E/K121E, as described in WO2015/007520 and WO2010/030671, the entire contents of which are hereby incorporated by reference. In such embodiments, said IFN-α2 mutant antagonizes wildtype IFN-α2 activity. In such embodiments, said mutant IFN-α2 has reduced affinity and/or activity for IFNAR1 while affinity and/or activity of IFNR2 is retained.

In some embodiments, the IFN-α2 mutant comprises (1) one or more mutations selected from R120E and R120E/K121E, which, without wishing to be bound by theory, create an antagonistic effect and (2) one or more mutations selected from K133A, R144A, R149A, and L153A, which, without wishing to be bound by theory, allow for an attenuated effect at, for example, IFNAR2. In some embodiments, the IFN-α2 mutant comprises a R120E mutation and either R149A or L153A. In an embodiment, the human IFN-α2 mutant comprises R120E and L153A.

In some embodiments, the human IFN-α2 mutant comprises one or more mutations selected from, L15A, A19W, R22A, R23A, L26A, F27A, L30A, L30V, K31A, D32A, R33K, R33A, R33Q, H34A, D35A, Q40A, D114R, L117A, R120A, R125A, K134A, R144A, A145G, A145M, M148A, R149A, S152A, L153A, and N156A as disclosed in WO 2013/059885, the entire disclosures of which are hereby incorporated by reference. In some embodiments, the human IFN-α2 mutant comprises the mutations H57Y, E58N, Q61S, and/or L30A as disclosed in WO 2013/059885.

In some embodiments, the human IFN-α2 mutant comprises the mutations H57Y, E58N, Q61S, and/or R33A as disclosed in WO 2013/059885. In some embodiments, the human IFN-α2 mutant comprises the mutations H57Y, E58N, Q61S, and/or M148A as disclosed in WO 2013/059885. In some embodiments, the human IFN-α2 mutant comprises the mutations H57Y, E58N, Q61S, and/or L153A as disclosed in WO 2013/059885. In some embodiments, the human IFN-α2 mutant comprises the mutations N65A, L80A, Y85A, and/or Y89A as disclosed in WO 2013/059885. In some embodiments, the human IFN-α2 mutant comprises the mutations N65A, L80A, Y85A, Y89A, and/or D114A as disclosed in WO 2013/059885.

In an embodiment, the modified signaling agent is interferon β. In such embodiments, the modified interferon β agent has reduced affinity and/or activity for the IFN-α/β receptor (IFNAR), i.e., IFNAR1 and/or IFNAR2 chains. In some embodiments, the modified interferon β agent has substantially reduced or ablated affinity and/or activity for the IFN-α/β receptor (IFNAR), i.e., IFNAR1 and/or IFNAR2 chains.

In an embodiment, the modified signaling agent is interferon γ. In such embodiments, the modified interferon γ agent has reduced affinity and/or activity for the interferon-gamma receptor (IFNGR), i.e., IFNGR1 and IFNGR2 chains. In some embodiments, the modified interferon γ agent has substantially reduced or ablated affinity and/or activity for the interferon-gamma receptor (IFNGR), i.e., IFNGR1 and/or IFNGR2 chains.

In an embodiment, the modified signaling agent is TNF-α. TNF is a pleiotropic cytokine with many diverse functions, including regulation of cell growth, differentiation, apoptosis, tumorigenesis, viral replication, autoimmunity, immune cell functions and trafficking, inflammation, and septic shock. It binds to two distinct membrane receptors on target cells: TNFR1 (p55) and TNFR2 (p75). TNFR1 exhibits a very broad expression pattern whereas TNFR2 is expressed preferentially on certain populations of lymphocytes, Tregs, endothelial cells, certain neurons, microglia, cardiac myocytes and mesenchymal stem cells. Very distinct biological pathways are activated in response to receptor activation, although there is also some overlap. As a general rule, without wishing to be bound by theory, TNFR1 signaling is associated with induction of apoptosis (cell death) and TNFR2 signaling is associated with activation of cell survival signals (e.g. activation of NFkB pathway). Administration of TNF is systemically toxic, and this is largely due to TNFR1 engagement. However, it should be noted that activation of TNFR2 is also associated with a broad range of activities and, as with TNFR1, in the context of developing TNF based therapeutics, control over TNF targeting and activity is important.

In some embodiments, the modified signaling agent has reduced affinity and/or activity for TNFR1 and/or TNFR2. In some embodiments, the modified signaling agent has substantially reduced or ablated affinity and/or activity for TNFR1 and/or TNFR2. TNFR1 is expressed in most tissues, and is involved in cell death signaling while, by contrast, TNFR2 is involved in cell survival signaling. Accordingly, in embodiments directed to methods of treating cancer, the modified signaling agent has reduced affinity and/or activity for TNFR1 and/or substantially reduced or ablated affinity and/or activity for TNFR2. In these embodiments, the chimeric proteins may be targeted to a cell for which apoptosis is desired, e.g. a tumor cell or a tumor vasculature endothelial cell. In embodiments directed to methods of promoting cell survival, for example, in neurogenesis for the treatment of neurodegenerative disorders, the modified signaling agent has reduced affinity and/or activity for TNFR2 and/or substantially reduced or ablated affinity and/or activity for TNFR1. Stated another way, the present chimeric proteins, in some embodiments, comprise modified TNF-α agent that allows of favoring either death or survival signals.

In some embodiments, the chimeric protein has a modified TNF having reduced affinity and/or activity for TNFR1 and/or substantially reduced or ablated affinity and/or activity for TNFR2. Such a chimera, in some embodiments, is a more potent inducer of apoptosis as compared to a wild type TNF and/or a chimera bearing only mutation(s) causing reduced affinity and/or activity for TNFR1. Such a chimera, in some embodiments, finds use in inducing tumor cell death or a tumor vasculature endothelial cell death (e.g. in the treatment of cancers). Also, in some embodiments, these chimeras avoid or reduce activation of $T_{reg}$ cells via TNFR2, for example, thus further supporting TNFR1-mediated antitumor activity in vivo.

In some embodiments, the chimeric protein has a modified TNF having reduced affinity and/or activity for TNFR2 and/or substantially reduced or ablated affinity and/or activity for TNFR1. Such a chimera, in some embodiments, is a more potent activator of cell survival in some cell types, which may be a specific therapeutic objective in various disease settings, including without limitation, stimulation of neurogenesis. In addition, such a TNFR2-favoring chimeras also are useful in the treatment of autoimmune diseases (e.g. Crohn's, diabetes, MS, colitis etc. and many others described herein). In some embodiments, the chimera is targeted to auto-reactive T cells. In some embodiments, the chimera promotes $T_{reg}$ cell activation and indirect suppression of cytotoxic T cells.

In some embodiments, the chimera causes the death of auto-reactive T cells, e.g. by activation of TNFR2 and/or avoidance of TNFR1 (e.g. a modified TNF having reduced affinity and/or activity for TNFR2 and/or substantially reduced or ablated affinity and/or activity for TNFR1). Without wishing to be bound by theory these auto-reactive T cells, have their apoptosis/survival signals altered e.g. by NFkB pathway activity/signaling alterations.

In some embodiments, a TNFR2 based chimera has additional therapeutic applications in diseases, including various autoimmune diseases, heart disease, de-myelinating and neurodegenerative disorders, and infectious disease, among others.

In an embodiment, the wild type TNF-α has the amino acid sequence of:

```
TNF-α
                                          (SEQ ID NO: 181)
VRSSSRTPSDKPVAHVVANPQAEGQLQWLNRRANALLANGVELRDNQLV

VPSEGLYLIYSQVLFKGQGCPSTHVLLTHTISRIAVSYQTKVNLLSAIK

SPCQRETPEGAEAKPWYEPIYLGGVFQLEKGDRLSAEINRPDYLDFAES

GQVYFGIIAL.
```

In such embodiments, the modified TNF-α agent has mutations at one or more amino acid positions 29, 31, 32, 84, 85, 86, 87, 88, 89, 145, 146 and 147 which produces a modified TNF-α with reduced receptor binding affinity. See, for example, U.S. Pat. No. 7,993,636, the entire contents of which are hereby incorporated by reference.

In some embodiments, the modified human TNF-α moiety has mutations at one or more amino acid positions R32, N34, Q67, H73, L75, T77, S86, Y87, V91, I97, T105, P106, A109, P113, Y115, E127, N137, D143, and A145, as described, for example, in WO/2015/007903, the entire contents of which is hereby incorporated by reference (numbering according to the human TNF sequence, Genbank accession number BAG70306, version BAG70306.1 GI: 197692685). In some embodiments, the modified human TNF-α moiety has substitution mutations selected from R32G, N34G, Q67G, H73G, L75G, L75A, L75S, T77A, S86G, Y87Q, Y87L, Y87A, Y87F, V91G, V91A, 197A, 197Q, I97S, T105G, P106G, A109Y, P113G, Y115G, Y115A, E127G, N137G, D143N, A145G and A145T. In an embodiment, the human TNF-α moiety has a mutation selected from Y87Q, Y87L, Y87A, and Y87F. In another embodiment, the human TNF-α moiety has a mutation selected from 197A, 197Q, and I97S. In a further embodiment, the human TNF-α moiety has a mutation selected from Y115A and Y115G.

In some embodiments, the modified TNF-α agent has one or more mutations selected from N39Y, S147Y, and Y87H, as described in WO2008/124086, the entire contents of which is hereby incorporated by reference.

In some embodiments, the modified human TNF-α moiety has mutations that provide receptor selectivity as described in PCT/IB2016/001668, the entire contents of which are hereby incorporated by reference. In some embodiments, the mutations to TNF are TNF-R1 selective. In some embodiments, the mutations to TNF which are TNF-R1 selective are at one or more of positions R32, S86, and E146. In some embodiments, the mutations to TNF which are TNF-R1 selective are one or more of R32W, S86T, and E146K. In some embodiments, the mutations to TNF which are TNF-R1 selective are one or more of R32W, R32W/S86T, R32W/E146K and E146K. In some embodiments, the mutations to TNF are TNF-R2 selective. In some embodiments, the mutations to TNF which are TNF-R2 selective are at one or more of positions A145, E146, and S147. In some embodiments, the mutations to TNF which are TNF-R2 selective are one or more of A145T, A145R, E146D, and S147D. In some embodiments, the mutations to TNF which are TNF-R2 selective are one or more of A145R, A145T/S147D, and A145T/E146D/S147D.

In an embodiment, the modified signaling agent is TNF-β. TNF-β can form a homotrimer or a heterotrimer with LT-β (LT-α1β2). In some embodiments, the modified signaling agent has substantially reduced or ablated affinity and/or activity for TNFR1 and/or TNFR2 and/or herpes virus entry mediator (HEVM) and/or LT-βR.

In an embodiment, the wild type TNF-β has the amino acid sequence of:

```
TNF-β
                                          (SEQ ID NO: 182)
LPGVGLTPSAAQTARQHPKMHLAHSNLKPAAHLIGDPSKQNSLLWRANTD

RAFLQDGFSLSNNSLLVPTSGIYFVYSQVVFSGKAYSPKATSSPLYLAHE

VQLFSSQYPFHVPLLSSQKMVYPGLQEPWLHSMYHGAAFQLTQGDQLSTH

TDGIPHLVLSPSTVFFGAFAL.
```

In such embodiments, the modified TNF-β agent may comprise mutations at one or more amino acids at positions 106-113, which produce a modified TNF-β with reduced receptor binding affinity to TNFR2. In an embodiment, the modified signaling agent has one or more substitution mutations at amino acid positions 106-113. In illustrative embodiments, the substitution mutations are selected from Q107E, Q107D, S106E, S106D, Q107R, Q107N, Q107E/S106E, Q107E/S106D, Q107D/S106E, and Q107D/S106D. In another embodiment, the modified signaling agent has an insertion of about 1 to about 3 amino acids at positions 106-113.

In some embodiments, the modified agent is a TNF family member (e.g. TNF-alpha, TNF-beta) which can be a single chain trimeric version as described in WO 2015/007903, the entire contents of which are incorporated by reference.

In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR1. In these embodiments, the modified agent is a TNF family member (e.g. TNF-alpha, TNF-beta) which also, optionally, has substantially reduced or ablated affinity and/or activity for TNFR2. In some embodiments, the modified agent is a TNF family member (e.g. TNF-alpha, TNF-beta) which has reduced affinity and/or activity, i.e. antagonistic activity (e.g. natural antagonistic activity or antagonistic activity that is the result of one or more mutations, see, e.g., WO 2015/007520, the entire contents of which are hereby incorporated by reference) at TNFR2.

In these embodiments, the modified agent is a TNF family member (e.g. TNF-alpha, TNF-beta) which also, optionally, has substantially reduced or ablated affinity and/or activity for TNFR1. The constructs of such embodiments find use in, for example, methods of dampening TNF response in a cell specific manner. In some embodiments, the antagonistic TNF family member (e.g. TNF-alpha, TNF-beta) is a single chain trimeric version as described in WO 2015/007903.

In an embodiment, the modified signaling agent is TRAIL. In some embodiments, the modified TRAIL agent has reduced affinity and/or activity for DR4 (TRAIL-RI) and/or DR5 (TRAIL-RII) and/or DcR1 and/or DcR2. In some embodiments, the modified TRAIL agent has substantially reduced or ablated affinity and/or activity for DR4 (TRAIL-RI) and/or DR5 (TRAIL-RII) and/or DcR1 and/or DcR2.

In an embodiment, the wild type TRAIL has the amino acid sequence of:

```
TRAIL
MAMMEVQGGPSLGQTCVLIVIFTVLLQSLCVAVTYVYFTNELKQMQDKY

SKSGIACFLKEDDSYWDPNDEESMNSPCWQVKWQLRQLVRKMILRTSEE

TISTVQEKQQNISPLVRERGPQRVAAHITGTRGRSNTLSSPNSKNEKAL

GRKINSWESSRSGHSFLSNLHLRNGELVIHEKGFYYIYSQTYFRFQEEI

KENTKNDKQMVQYIYKYTSYPDPILLMKSARNSCWSKDAEYGLYSIYQG

GIFELKENDRIFVSVTNEHLIDMDHEASFFGAFLVG.
```

In such embodiments, the modified TRAIL agent may comprise a mutation at amino acid positions T127-R132, E144-R149, E155-H161, Y189-Y209, T214-1220, K224-A226, W231, E236-L239, E249-K251, T261-H264 and H270-E271 (Numbering based on the human sequence, Genbank accession number NP_003801, version 10 NP_003801.1, GI: 4507593; see above).

In an embodiment, the modified signaling agent is IL-1. In an embodiment, the modified signaling agent is IL-1α or IL-1β. In an embodiment, the modified signaling agent is IL-1β. In some embodiments, the modified signaling agent has reduced affinity and/or activity for IL-1R1 and/or IL-1RAcP. In some embodiments, the modified signaling agent has substantially reduced or ablated affinity and/or activity for IL-1R1 and/or IL-1RAcP. In some embodiments, the modified signaling agent has reduced affinity and/or activity for IL-1R2. In some embodiments, the modified signaling agent has substantially reduced or ablated affinity and/or activity for IL-1R2. For instance, in some embodiments, the present modified IL-1 agents avoid interaction at IL-1R2 and therefore substantially reduce its function as a decoy and/or sink for therapeutic agents.

In an embodiment, the wild type IL-1β has the amino acid sequence of:

```
IL-1 beta (mature form, wild type)
                                    (SEQ ID NO: 183)
APVRSLNCTLRDSQQKSLVMSGPYELKALHLQGQDMEQQVVFSMSFVQGE

ESNDKIPVALGLKEKNLYLSCVLKDDKPTLQLESVDPKNYPKKKMEKRFV

FNKIEINNKLEFESAQFPNWYISTSQAENMPVFLGGTKGGQDITDFTMQF

VSS.
```

IL1 is a proinflammatory cytokine and an important immune system regulator. It is a potent activator of CD4 T cell responses, increases proportion of Th17 cells and expansion of IFNγ and IL-4 producing cells. IL-1 is also a potent regulator of $CD8^+$ T cells, enhancing antigen-specific $CD8^+$ T cell expansion, differentiation, migration to periphery and memory. IL-1 receptors comprise IL-1R1 and IL-1R2. Binding to and signaling through the IL-1R1 constitutes the mechanism whereby IL-1 mediates many of its biological (and pathological) activities. IL1-R2 can function as a decoy receptor, thereby reducing IL-1 availability for interaction and signaling through the IL-1R1.

In some embodiments, the modified IL-1 has reduced affinity and/or activity (e.g. agonistic activity) for IL-1R1. In some embodiments, the modified IL-1 has substantially reduced or ablated affinity and/or activity for IL-1R2. In such embodiments, there is restorable IL-1/IL-1R1 signaling and prevention of loss of therapeutic chimeras at IL-R2 and therefore a reduction in dose of IL-1 that is required (e.g. relative to wild type or a chimera bearing only an attenuation mutation for IL-R1). Such constructs find use in, for example, methods of treating cancer, including, for example, stimulating the immune system to mount an anti-cancer response.

In some embodiments, the modified IL-1 has reduced affinity and/or activity (e.g. antagonistic activity, e.g. natural antagonistic activity or antagonistic activity that is the result of one or more mutations, see, e.g., WO 2015/007520, the entire contents of which are hereby incorporated by reference) for IL-1R1. In some embodiments, the modified IL-1 has substantially reduced or ablated affinity and/or activity for IL-1R2. In such embodiments, there is the IL-1/IL-1R1 signaling is not restorable and prevention of loss of therapeutic chimeras at IL-R2 and therefore a reduction in dose of IL-1 that is required (e.g. relative to wild type or a chimera bearing only an attenuation mutation for IL-R1).

Such constructs find use in, for example, methods of treating autoimmune diseases, including, for example, suppressing the immune system.

In such embodiments, the modified signaling agent has a deletion of amino acids 52-54 which produces a modified human IL-1β with reduced binding affinity for type I IL-1R and reduced biological activity. See, for example, WO 1994/000491, the entire contents of which are hereby incorporated by reference. In some embodiments, the modified human IL-1β has one or more substitution mutations selected from A117G/P118G, R120X, L122A, T125G/L126G, R127G, Q130X, Q131G, K132A, S137G/Q138Y, L145G, H146X, L145A/L147A, Q148X, Q148G/Q150G, Q150G/D151A, M152G, F162A, F162A/Q164E, F166A, Q164E/E167K, N169G/D170G, 1172A, V174A, K208E, K209X, K209A/K210A, K219X, E221X, E221 S/N224A, N224S/K225S, E244K, N245Q (where X can be any change in amino acid, e.g., a non-conservative change), which exhibit reduced binding to IL-1R, as described, for example, in WO2015/007542 and WO/2015/007536, the entire contents of which is hereby incorporated by reference (numbering base on the human IL-1β sequence, Genbank accession number NP_000567, version NP-000567.1, GI: 10835145). In some embodiments, the modified human IL-1β may have one or more mutations selected from R120A, R120G, Q130A, Q130W, H146A, H146G, H146E, H146N, H146R, Q148E, Q148G, Q148L, K209A, K209D, K219S, K219Q, E221S and E221K. In an embodiment, the modified human IL-1β comprises the mutations Q131G and Q148G. In an embodiment, the modified human IL-1β comprises the mutations Q148G and K208E. In an embodiment, the modified human IL-1β comprises the mutations R120G and Q131G. In an embodiment, the modified human IL-1β comprises the mutations R120G and H146A. In an embodiment, the modified human IL-1β comprises the mutations R120G and H146N. In an embodiment, the modified human IL-1β comprises the mutations R120G and H146R. In an embodiment, the modified human IL-1β comprises the mutations R120G and H146E. In an embodiment, the modified human IL-1β comprises the mutations R120G and H146A. In an embodiment, the modified human IL-1β comprises the mutations R120G and H146N. In an embodiment, the modified human IL-1β comprises the mutations R120G and H146R. In an embodiment, the modified human IL-1β comprises the mutations R120G and H146E. In an embodiment, the modified human IL-1β comprises the mutations R120G and H146G. In an embodiment, the modified human IL-1β comprises the mutations R120G and K208E. In an embodiment, the modified human IL-1β comprises the mutations R120G, F162A, and Q164E.

In an embodiment, the modified signaling agent is IL-2. In such an embodiment, the modified signaling agent has reduced affinity and/or activity for IL-2Rα and/or IL-2Rβ and/or IL-2Rγ. In some embodiments, the modified signaling agent has reduced affinity and/or activity for IL-2Rβ and/or IL-2Rγ. In some embodiments, the modified signaling agent has substantially reduced or ablated affinity and/or activity for IL-2Rα. Such embodiments may be relevant for treatment of cancer, for instance when the modified IL-2 is agonistic at IL-2Rβ and/or IL-2Rγ. For instance, the present constructs may favor attenuated activation of $CD8^+$ T cells (which can provide an anti-tumor effect), which have IL2 receptors β and γ and disfavor $T_{regs}$ (which can provide an immune suppressive, pro-tumor effect), which have IL2 receptors α, β, and γ. Further, in some embodiments, the preferences for IL-2Rβ and/or IL-2Rγ over IL-2Rα avoid IL-2 side effects such as pulmonary edema. Also, IL-2-based chimeras are useful for the treatment of autoimmune diseases, for instance when the modified IL-2 is antagonistic (e.g. natural antagonistic activity or antagonistic activity that is the result of one or more mutations, see, e.g., WO 2015/007520, the entire contents of which are hereby incorporated by reference) at IL-2Rβ and/or IL-2Rγ. For instance, the present constructs may favor attenuated suppression of $CD8^+$ T cells (and therefore dampen the immune response), which have IL2 receptors β and γ and disfavor $T_{regs}$ which have IL2 receptors α, β, and γ. Alternatively, in some embodiments, the chimeras bearing IL-2 favor the activation of $T_{regs}$, and therefore immune suppression, and activation of disfavor of $CD8^+$ T cells. For instance, these constructs find use in the treatment of diseases or diseases that would benefit from immune suppression, e.g. autoimmune disorders.

In some embodiments, the chimeric protein has targeting moieties as described herein directed to $CD8^+$ T cells as well as a modified IL-2 agent having reduced affinity and/or activity for IL-2Rβ and/or IL-2Rγ and/or substantially reduced or ablated affinity and/or activity for IL-2Rα. In some embodiments, these constructs provide targeted $CD8^+$ T cell activity and are generally inactive (or have substantially reduced activity) towards $T_{reg}$ cells. In some embodiments, such constructs have enhanced immune stimulatory effect compared to wild type IL-2 (e.g., without wishing to be bound by theory, by not stimulating Tregs), whilst eliminating or reducing the systemic toxicity associated with IL-2.

In an embodiment, the wild type IL-2 has the amino acid sequence of:

```
IL-2 (mature form, wild type)
                                    (SEQ ID NO: 184)
APTSSSTKKTQLQLEHLLLDLQMILNGINNYKNPKLTRMLTFKFYMPKK

ATELKHLQCLEEELKPLEEVLNLAQSKNFHLRPRDLISNINVIVLELKG

SETTFMCEYADETATIVEFLNRWITFCQSIISTLT.
```

In such embodiments, the modified IL-2 agent has one or more mutations at amino acids L72 (L72G, L72A, L72S, L72T, L72Q, L72E, L72N, L72D, L72R, or L72K), F42 (F42A, F42G, F42S, F42T, F42Q, F42E, F42N, F42D, F42R, or F42K) and Y45 (Y45A, Y45G, Y45S, Y45T, Y45Q, Y45E, Y45N, Y45D, Y45R or Y45K). Without wishing to be bound by theory, it is believed that these modified IL-2 agents have reduced affinity for the high-affinity IL-2 receptor and preserves affinity to the intermediate-affinity IL-2 receptor, as compared to the wild-type IL-2. See, for example, US Patent Publication No. 2012/0244112, the entire contents of which are hereby incorporated by reference.

In an embodiment, the modified signaling agent is IL-3. In some embodiments, the modified signaling agent has reduced affinity and/or activity for the IL-3 receptor, which is a heterodimer with a unique alpha chain paired with the common beta (beta c or CD131) subunit. In some embodiments, the modified signaling agent has substantially reduced or ablated affinity and/or activity for the IL-3 receptor, which is a heterodimer with a unique alpha chain paired with the common beta (beta c or CD131) subunit.

In an embodiment, the modified signaling agent is IL-4. In such an embodiment, the modified signaling agent has reduced affinity and/or activity for type 1 and/or type 2 IL-4 receptors. In such an embodiment, the modified signaling agent has substantially reduced or ablated affinity and/or activity for type 1 and/or type 2 IL-4 receptors. Type 1 IL-4 receptors are composed of the IL-4Rα subunit with a common γ chain and specifically bind IL-4. Type 2 IL-4 receptors include an IL-4Rα subunit bound to a different subunit known as IL-13Rα1. In some embodiments, the modified signaling agent has substantially reduced or ablated affinity and/or activity the type 2 IL-4 receptors.

In an embodiment, the wild type IL-4 has the amino acid sequence of:

```
IL-4 (mature form, wild type)
                                     (SEQ ID NO: 185)
HKCDITLQEIIKTLNSLTEQKTLCTELTVTDIFAASKNTTEKETFCRAA

TVLRQFYSHHEKIDTRCLGATAQQFHRHKQLIRFLKRLDRNLWGLAGLN

SCPVKEANQSTLENFLERLKTIMREKYSKCSS.
```

In such embodiments, the modified IL-4 agent has one or more mutations at amino acids R121 (R121A, R121D, R121E, R121F, R121H, R1211, R121K, R121N, R121P, R121T, R121W), E122 (E122F), Y124 (Y124A, Y124Q, Y124R, Y124S, Y124T) and S125 (S125A). Without wishing to be bound by theory, it is believed that these modified IL-4 agents maintain the activity mediated by the type I receptor, but significantly reduces the biological activity mediated by the other receptors. See, for example, U.S. Pat. No. 6,433,157, the entire contents of which are hereby incorporated by reference.

In an embodiment, the modified signaling agent is IL-6. IL-6 signals through a cell-surface type I cytokine receptor complex including the ligand-binding IL-6R chain (CD126), and the signal-transducing component gp130. IL-6 may also bind to a soluble form of IL-6R (sIL-6R), which is the extracellular portion of IL-6R. The sIL-6R/IL-6 complex may be involved in neurites outgrowth and survival of neurons and, hence, may be important in nerve regeneration through remyelination. Accordingly, in some embodiments, the modified signaling agent has reduced affinity and/or activity for IL-6R/gp130 and/or sIL-6R. In some embodiments, the modified signaling agent has substantially reduced or ablated affinity and/or activity for IL-6R/gp130 and/or sIL-6R.

In an embodiment, the wild type IL-6 has the amino acid sequence of:

```
IL-6 (mature form, wild type)
                                     (SEQ ID NO: 186)
APVPPGEDSKDVAAPHRQPLTSSERIDKQIRYILDGISALRKETCNKSN

MCESSKEALAENNLNLPKMAEKDGCFQSGFNEETCLVKIITGLLEFEVY

LEYLQNRFESSEEQARAVQMSTKVLIQFLQKKAKNLDAITTPDPTTNAS

LTTKLQAQNQWLQDMTTHLILRSFKEFLQSSLRALRQM.
```

In such embodiments, the modified signaling agent has one or more mutations at amino acids 58, 160, 163, 171 or 177. Without wishing to be bound by theory, it is believed that these modified IL-6 agents exhibit reduced binding affinity to IL-6Ralpha and reduced biological activity. See, for example, WO 97/10338, the entire contents of which are hereby incorporated by reference.

In an embodiment, the modified signaling agent is IL-10. In such an embodiment, the modified signaling agent has reduced affinity and/or activity for IL-10 receptor-1 and IL-10 receptor-2. In some embodiments, the modified signaling agent has substantially reduced or ablated affinity and/or activity for IL-10 receptor-1 and IL-10 receptor-2 In an embodiment, the modified signaling agent is IL-11. In such an embodiment, the modified signaling agent has reduced affinity and/or activity for IL-11Rα and/or IL-11Rβ and/or gp130. In such an embodiment, the modified signaling agent has substantially reduced or ablated affinity and/or activity for IL-11Rα and/or IL-11Rβ and/or gp130.

In an embodiment, the modified signaling agent is IL-12. In such an embodiment, the modified signaling agent has reduced affinity and/or activity for IL-12Rβ1 and/or IL-12Rβ2. In such an embodiment, the modified signaling agent has substantially reduced or ablated affinity and/or activity for IL-12Rβ1 and/or IL-12Rβ2.

In an embodiment, the modified signaling agent is IL-13. In such an embodiment, the modified signaling agent has reduced affinity and/or activity for the IL-4 receptor (IL-4Rα) and IL-13Rα1. In some embodiments, the modified signaling agent has substantially reduced or ablated affinity and/or activity for IL-4 receptor (IL-4Rα) or IL-13Rα1.

In an embodiment, the wild type IL-13 has the amino acid sequence of:

```
IL-13 (mature form, wild type)
                                     (SEQ ID NO: 187)
SPGPVPPSTALRELIEELVNITQNQKAPLCNGSMVWSINLTAGMYCAAL

ESLINVSGCSAIEKTQRMLSGFCPHKVSAGQFSSLHVRDTKIEVAQFVK

DLLLHLKKLFREGRFN.
```

In such embodiments, the modified IL-13 agent has one or more mutations at amino acids 13, 16, 17, 66, 69, 99, 102, 104, 105, 106, 107, 108, 109, 112, 113 and 114. Without wishing to be bound by theory, it is believed that these modified IL-13 agents exhibit reduced biological activity. See, for example, WO 2002/018422, the entire contents of which are hereby incorporated by reference.

In an embodiment, the modified signaling agent is IL-18. In some embodiments, the modified signaling agent has reduced affinity and/or activity for IL-18Rα and/or IL-18Rβ. In some embodiments, the modified signaling agent has substantially reduced or ablated affinity and/or activity for IL-18Rα and/or IL-18Rβ. In some embodiments, the modified signaling agent has substantially reduced or ablated affinity and/or activity for IL-18Rα type II, which is an isoform of IL-18Rα that lacks the TIR domain required for signaling.

In an embodiment, the wild type IL-18 has the amino acid sequence of:

```
IL-18 (wild type)
                                     (SEQ ID NO: 188)
MAAEPVEDNCINFVAMKFIDNTLYFIAEDDENLESDYFGKLESKLSVIR

NLNDQVLFIDQGNRPLFEDMTDSDCRDNAPRTIFIISMYKDSQPRGMAV

TISVKCEKISTLSCENKIISFKEMNPPDNIKDTKSDIIFFQRSVPGHDN

KMQFESSSYEGYFLACEKERDLFKLILKKEDELGDRSIMFTVQNEDL.
```

In such embodiments, the modified IL-18 agent may comprise one or more mutations in amino acids or amino acid regions selected from Y37-K44, R49-Q54, D59-R63, E67-C74, R80, M87-A97, N127-K129, Q139-M149, K165-K171, R183 and Q190-N191, as described in WO/2015/007542, the entire contents of which are hereby incorporated by reference (numbering based on the human IL-18 sequence, Genbank accession number AAV38697, version AAV38697.1, GI: 54696650).

In an embodiment, the modified signaling agent is IL-33. In such an embodiment, the modified signaling agent has reduced affinity and/or activity for the ST-2 receptor and IL-1RAcP. In some embodiments, the modified signaling agent has substantially reduced or ablated affinity and/or activity for the ST-2 receptor and IL-1RAcP.

In an embodiment, the wild type IL-33 has the amino acid sequence of:

```
IL-33 (wild type)
                                    (SEQ ID NO: 189)
MKPKMKYSTNKISTAKWKNTASKALCFKLGKSQQKAKEVCPMYFMKLRS

GLMIKKEACYFRRETTKRPSLKTGRKHKRHLVLAACQQQSTVECFAFGI

SGVQKYTRALHDSSITGISPITEYLASLSTYNDQSITFALEDESYEIYV

EDLKKDEKKDKVLLSYYESQHPSNESGDGVDGKMLMVTLSPTKDFWLHA

NNKEHSVELHKCEKPLPDQAFFVLHNMHSNCVSFECKTDPGVFIGVKDN

HLALIKVDSSENLCTENILFKLSET.
```

In such embodiments, the modified IL-33 agent may comprise one or more mutations in amino acids or amino acid regions selected from I113-Y122, S127-E139, E144-D157, Y163-M183, E200, Q215, L220-C227 and T260-E269, as described in WO/2015/007542, the entire contents of which are hereby incorporated by reference (numbering based on the human sequence, Genbank accession number NP_254274, version NP_254274.1, GI:15559209).

Linkers

In some embodiments, the present chimeric protein optionally comprises one or more linkers. In some embodiments, the present chimeric protein comprises a linker connecting the targeting moiety and the signaling agent. In some embodiments, the present chimeric protein comprises a linker within the signaling agent (e.g. in the case of single chain TNF, which can comprise two linkers to yield a trimer).

In some embodiments vectors encoding the present chimeric proteins linked as a single nucleotide sequence to any of the linkers described herein are provided and may be used to prepare such chimeric proteins.

In some embodiments, the linker length allows for efficient binding of a targeting moiety and the signaling agent to their receptors. For instance, in some embodiments, the linker length allows for efficient binding of one of the targeting moieties and the signaling agent to receptors on the same cell as well as the efficient binding of the other targeting moiety to another cell. Illustrative pairs of cells are provided elsewhere herein.

In some embodiments the linker length is at least equal to the minimum distance between the binding sites of one of the targeting moieties and the signaling agent to receptors on the same cell. In some embodiments the linker length is at least twice, or three times, or four times, or five times, or ten times, or twenty times, or 25 times, or 50 times, or one hundred times, or more the minimum distance between the binding sites of one of the targeting moieties and the signaling agent to receptors on the same cell.

As described herein, the linker length allows for efficient binding of one of the targeting moieties and the signaling agent to receptors on the same cell, the binding being sequential, e.g. targeting moiety/receptor binding preceding signaling agent/receptor binding.

In some embodiments, there are two linkers in a single chimera, each connecting the signaling agent to a targeting moiety. In various embodiments, the linkers have lengths that allow for the formation of a site that has a disease cell and an effector cell without steric hindrance that would prevent modulation of the either cell.

The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present chimeric protein.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is a polypeptide. In some embodiments, the linker is greater than about 100 amino acids long. For example, the linker may be greater than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In some embodiments, a linker connects the two targeting moieties to each other and this linker has a short length and a linker connects a targeting moiety and a signaling agent this linker is longer than the linker connecting the two targeting moieties. For example, the difference in amino acid length between the linker connecting the two targeting moieties and the linker connecting a targeting moiety and a signaling agent may be about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). For example, in some embodiments, the linker is $(Gly_4Ser)_n$, where n is from about 1 to about 8, e.g. 1, 2, 3, 4, 5, 6, 7, or 8. In an embodiment, the linker sequence is GGSGGSGGGGSGGGGS (SEQ ID NO: 190). Additional illustrative linkers include, but are not limited to, linkers having the sequence LE, GGGGS (SEQ ID NO: 191), $(GGGGS)_n$ (n=1-4) (SEQ ID NO: 192), $(Gly)_8$ (SEQ ID NO: 193), $(Gly)_6$ (SEQ ID NO: 194), (EAAAK), (n=1-3)

(SEQ ID NO: 195), A(EAAAK), A (n=2-5) (SEQ ID NO: 196), AEAAAKEAAAKA (SEQ ID NO: 197), A(EAAAK)$_4$ ALEA(EAAAK)$_4$A (SEQ ID NO: 198), PAPAP (SEQ ID NO: 199), KESGSVSSEQLAQFRSLD (SEQ ID NO: 200), EGKSSGSGSESKST (SEQ ID NO: 201), GSAGSAAGSGEF (SEQ ID NO: 202), and $(XP)_n$, with X designating any amino acid, e.g., Ala, Lys, or Glu. In various embodiments, the linker is GGS.

In some embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). In various embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2.

According to crystallographic studies, the immunoglobulin hinge region can be further subdivided functionally into three regions: the upper hinge region, the core region, and the lower hinge region. See Shin et al., 1992 *Immunological Reviews* 130:87. The upper hinge region includes amino acids from the carboxyl end of $C_{H1}$ to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys which, when dimerized by disulfide bond formation, results in a cyclic octapeptide believed to act as a pivot, thus conferring flexibility. In various embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In various embodiments, the linker of the present invention comprises one or more glycosylation sites. In various embodiments, the linker is a hinge-CH2-CH3 domain of a human IgG4 antibody.

If desired, the present chimeric protein can be linked to an antibody Fc region, comprising one or both of $C_H2$ and $C_H3$ domains, and optionally a hinge region. For example, vectors encoding the present chimeric proteins linked as a single nucleotide sequence to an Fc region can be used to prepare such polypeptides.

In some embodiments, the linker is a synthetic linker such as PEG.

In various embodiments, the linker may be functional. For example, without limitation, the linker may function to improve the folding and/or stability, improve the expression, improve the pharmacokinetics, and/or improve the bioactivity of the present chimeric protein. In another example, the linker may function to target the chimeric protein to a particular cell type or location.

In various embodiments, the chimeric proteins may by conjugated and/or fused with another agent to extend half-life or otherwise improve pharmacodynamic and pharmacokinetic properties. In some embodiments, the chimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In some embodiments, the chimeric protein may be fused or conjugated with an antibody or an antibody fragment such as an Fc fragment. For example, the chimeric protein may be fused to either the N-terminus or the C-terminus of the Fc domain of human immunoglobulin (Ig) G. In various embodiments, each of the individual chimeric proteins is fused to one or more of the agents described in BioDrugs (2015) 29:215-239, the entire contents of which are hereby incorporated by reference.

Production of Chimeric Proteins

Methods for producing the chimeric proteins of the invention are described herein. For example, DNA sequences encoding the chimeric proteins of the invention (e.g., DNA sequences encoding the modified signaling agent and the targeting moiety and the linker) can be chemically synthesized using methods known in the art. Synthetic DNA sequences can be ligated to other appropriate nucleotide sequences, including, e.g., expression control sequences, to produce gene expression constructs encoding the desired chimeric proteins. Accordingly, in various embodiments, the present invention provides for isolated nucleic acids comprising a nucleotide sequence encoding the chimeric protein of the invention.

Nucleic acids encoding the chimeric protein of the invention can be incorporated (ligated) into expression vectors, which can be introduced into host cells through transfection, transformation, or transduction techniques. For example, nucleic acids encoding the chimeric protein of the invention can be introduced into host cells by retroviral transduction. Illustrative host cells are *E. coli* cells, Chinese hamster ovary (CHO) cells, human embryonic kidney 293 (HEK 293) cells, HeLa cells, baby hamster kidney (BHK) cells, monkey kidney cells (COS), human hepatocellular carcinoma cells (e.g., Hep G2), and myeloma cells. Transformed host cells can be grown under conditions that permit the host cells to express the genes that encode the chimeric protein of the invention. Accordingly, in various embodiments, the present invention provides expression vectors comprising nucleic acids that encode the chimeric protein of the invention. In various embodiments, the present invention additional provides host cells comprising such expression vectors.

Specific expression and purification conditions will vary depending upon the expression system employed. For example, if a gene is to be expressed in *E. coli*, it is first cloned into an expression vector by positioning the engineered gene downstream from a suitable bacterial promoter, e.g., Trp or Tac, and a prokaryotic signal sequence.

In another example, if the engineered gene is to be expressed in eukaryotic host cells, e.g., CHO cells, it is first inserted into an expression vector containing for example, a suitable eukaryotic promoter, a secretion signal, enhancers, and various introns. The gene construct can be introduced into the host cells using transfection, transformation, or transduction techniques.

The chimeric protein of the invention can be produced by growing a host cell transfected with an expression vector encoding the chimeric protein under conditions that permit expression of the protein. Following expression, the protein can be harvested and purified using techniques well known in the art, e.g., affinity tags such as glutathione-S-transferase (GST) and histidine tags or by chromatography.

Accordingly, in various embodiments, the present invention provides for a nucleic acid encoding a chimeric protein of the present invention. In various embodiments, the present invention provides for a host cell comprising a nucleic acid encoding a chimeric protein of the present invention.

Pharmaceutically Acceptable Salts and Excipients

The chimeric proteins described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science,* 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Pharmaceutical Compositions and Formulations

In various embodiments, the present invention pertains to pharmaceutical compositions comprising the chimeric proteins described herein and a pharmaceutically acceptable carrier or excipient. Any pharmaceutical compositions described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

In various embodiments, pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

The present invention includes the described pharmaceutical compositions (and/or additional therapeutic agents) in various formulations. Any inventive pharmaceutical composition (and/or additional therapeutic agents) described herein can take the form of solutions, suspensions, emulsion, drops, tablets, pills, pellets, capsules, capsules containing liquids, gelatin capsules, powders, sustained-release formulations, suppositories, emulsions, aerosols, sprays, suspensions, lyophilized powder, frozen suspension, dessicated powder, or any other form suitable for use. In one embodiment, the composition is in the form of a capsule. In another embodiment, the composition is in the form of a tablet. In yet another embodiment, the pharmaceutical composition is formulated in the form of a soft-gel capsule. In a further embodiment, the pharmaceutical composition is formulated in the form of a gelatin capsule. In yet another embodiment, the pharmaceutical composition is formulated as a liquid.

Where necessary, the inventive pharmaceutical compositions (and/or additional agents) can also include a solubilizing agent. Also, the agents can be delivered with a suitable vehicle or delivery device as known in the art. Combination therapies outlined herein can be co-delivered in a single delivery vehicle or delivery device.

The formulations comprising the inventive pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, any pharmaceutical compositions (and/or additional agents) described herein is formulated in accordance with routine procedures as a composition adapted for a mode of administration described herein.

Routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically. Administration can be local or systemic. In some embodiments, the administering is effected orally. In another embodiment, the administration is by parenteral injection. The mode of administration can be left to the discretion of the practitioner, and depends in-part upon the site of the medical condition. In most instances, administration results in the release of any agent described herein into the bloodstream.

In one embodiment, the chimeric protein described herein is formulated in accordance with routine procedures as a composition adapted for oral administration. Compositions for oral delivery can be in the form of tablets, lozenges, aqueous or oily suspensions, granules, powders, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving any chimeric proteins described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art. Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyetheylene glycol), and suitable mixtures thereof.

The compositions provided herein, alone or in combination with other suitable components, can be made into aerosol formulations (i.e., "nebulized") to be administered via inhalation. Aerosol formulations can be placed into pressurized acceptable propellants, such as dichlorodifluoromethane, propane, nitrogen, and the like.

Any inventive pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, a controlled-release system can be placed in proximity of the target area to be treated, thus requiring only a fraction of the systemic dose (see, e.g., Goodson, in *Medical Applications of Controlled Release, supra*, vol. 2, pp. 115-138 (1984)). Other controlled-release systems discussed in the review by Langer, 1990*, Science* 249:1527-1533) may be used.

Pharmaceutical formulations preferably are sterile. Sterilization can be accomplished, for example, by filtration through sterile filtration membranes. Where the composition is lyophilized, filter sterilization can be conducted prior to or following lyophilization and reconstitution.

Administration and Dosage

It will be appreciated that the actual dose of the chimeric protein to be administered according to the present invention will vary according to the particular dosage form, and the mode of administration. Many factors that may modify the action of the chimeric protein (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

In some embodiments, a suitable dosage of the chimeric protein is in a range of about 0.01 mg/kg to about 10 g/kg of body weight of the subject, about 0.01 mg/kg to about 1 g/kg of body weight of the subject, about 0.01 mg/kg to about 100 mg/kg of body weight of the subject, about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 100 mg/kg body weight, about 1 g/kg of body weight, about 10 g/kg of body weight, inclusive of all values and ranges therebetween.

Individual doses of the chimeric protein can be administered in unit dosage forms (e.g., tablets or capsules) containing, for example, from about 0.01 mg to about 100 g, from about 0.01 mg to about 75 g, from about 0.01 mg to about 50 g, from about 0.01 mg to about 25 g, about 0.01 mg to about 10 g, about 0.01 mg to about 7.5 g, about 0.01 mg to about 5 g, about 0.01 mg to about 2.5 g, about 0.01 mg to about 1 g, about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 10 g, about 25 g, about 50 g, about 75 g, about 100 g, inclusive of all values and ranges therebetween.

In one embodiment, the chimeric protein is administered at an amount of from about 0.01 mg to about 100 g daily, from about 0.01 mg to about 75 g daily, from about 0.01 mg to about 50 g daily, from about 0.01 mg to about 25 g daily, from about 0.01 mg to about 10 g daily, from about 0.01 mg to about 7.5 g daily, from about 0.01 mg to about 5 g daily, from about 0.01 mg to about 2.5 g daily, from about 0.01 mg to about 1 g daily, from about 0.01 mg to about 100 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the chimeric protein is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 500 mg, about 1 g, about 2.5 g, about 5 g, about 7.5 g, about 10 g, about 25 g, about 50 g, about 75 g, about 100 g, inclusive of all values and ranges therebetween.

In accordance with certain embodiments of the invention, the pharmaceutical composition comprising the chimeric protein may be administered, for example, more than once daily (e.g., about two times, about three times, about four times, about five times, about six times, about seven times, about eight times, about nine times, or about ten times daily), about once per day, about every other day, about every third day, about once a week, about once every two weeks, about once every month, about once every two months, about once every three months, about once every six months, or about once every year.

Combination Therapy and Additional Therapeutic Agents

In various embodiments, the pharmaceutical composition of the present invention is co-administered in conjunction with additional therapeutic agent(s). Co-administration can be simultaneous or sequential.

In one embodiment, the additional therapeutic agent and the chimeric protein of the present invention are administered to a subject simultaneously. The term “simultaneously” as used herein, means that the additional therapeutic agent and the chimeric protein are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the chimeric protein can be by simultaneous administration of a single formulation (e.g., a formulation comprising the additional therapeutic agent and the chimeric protein) or of separate formulations (e.g., a first formulation including the additional therapeutic agent and a second formulation including the chimeric protein).

Co-administration does not require the therapeutic agents to be administered simultaneously, if the timing of their administration is such that the pharmacological activities of the additional therapeutic agent and the chimeric protein overlap in time, thereby exerting a combined therapeutic effect. For example, the additional therapeutic agent and the chimeric protein can be administered sequentially. The term “sequentially” as used herein means that the additional therapeutic agent and the chimeric protein are administered with a time separation of more than about 60 minutes.

For example, the time between the sequential administration of the additional therapeutic agent and the chimeric protein can be more than about 60 minutes, more than about 2 hours, more than about 5 hours, more than about 10 hours, more than about 1 day, more than about 2 days, more than about 3 days, more than about 1 week apart, more than about 2 weeks apart, or more than about one month apart. The optimal administration times will depend on the rates of metabolism, excretion, and/or the pharmacodynamic activity of the additional therapeutic agent and the chimeric protein being administered. Either the additional therapeutic agent or the chimeric protein cell may be administered first.

Co-administration also does not require the therapeutic agents to be administered to the subject by the same route of administration. Rather, each therapeutic agent can be administered by any appropriate route, for example, parenterally or non-parenterally.

In some embodiments, the chimeric protein described herein acts synergistically when co-administered with another therapeutic agent. In such embodiments, the chimeric protein and the additional therapeutic agent may be administered at doses that are lower than the doses employed when the agents are used in the context of monotherapy.

In some embodiments, the present invention pertains to chemotherapeutic agents as additional therapeutic agents. For example, without limitation, such combination of the present chimeric proteins and chemotherapeutic agent find use in the treatment of cancers, as described elsewhere herein. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside (“Ara-C”); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine;

novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In some embodiments, inclusive of, without limitation, infectious disease applications, the present invention pertains to anti-infectives as additional therapeutic agents. In some embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In some embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In some embodiments, inclusive, without limitation, of autoimmune applications, the additional therapeutic agent is an immunosuppressive agent. In some embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In some embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin). Additional anti-inflammatory agents are described, for example, in U.S. Pat. No. 4,537,776, the entire contents of which is incorporated by reference herein.

In some embodiments, the present invention relates to combination therapy with one or more immune-modulating agents, for example, without limitation, agents that modulate immune checkpoint. In various embodiments, the immune-modulating agent targets one or more of PD-1, PD-L1, and PD-L2. In various embodiments, the immune-modulating agent is PD-1 inhibitor. In various embodiments, the immune-modulating agent is an antibody specific for one or more of PD-1, PD-L1, and PD-L2 as described herein. For instance, in some embodiments, the immune-modulating agent is an antibody such as, by way of non-limitation, nivolumab, (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), MPDL3280A (ROCHE). In some embodiments, the immune-modulating agent targets one or more of CD137 or CD137L. In various embodiments, the immune-modulating agent is an antibody specific for one or more of CD137 or CD137L. For instance, in some embodiments, the immune-modulating agent is an antibody such as, by way of non-limitation, urelumab (also known as BMS-663513 and anti-4-1BB antibody). In some embodiments, the present chimeric protein is combined with urelumab (optionally with one or more of nivolumab, lirilumab, and urelumab) for the treatment of solid tumors and/or B-cell non-Hodgkins lymphoma and/or head and neck cancer and/or multiple myeloma. In some embodiments, the immune-modulating agent is an agent that targets one or more of CTLA-4, AP2M1, CD80, CD86, SHP-2, and PPP2R5A. In various embodiments, the immune-modulating agent is an antibody specific for one or more of CTLA-4, AP2M1, CD80, CD86, SHP-2, and PPP2R5A. For instance, in some embodiments, the immune-modulating agent is an antibody such as, by way of non-limitation, ipilimumab (MDX-010, MDX-101, Yervoy, BMS) and/or tremelimumab (Pfizer). In some embodiments, the present chimeric protein is combined with ipilimumab (optionally with bavituximab) for the treatment of one or more of melanoma, prostate cancer, and lung cancer. In various embodiments, the immune-modulating agent targets CD20. In various embodiments, the immune-modulating agent is an antibody specific CD20. For instance, in some embodiments, the immune-modulating agent is an antibody such as, by way of non-limitation, Ofatumumab (GENMAB), obinutuzumab (GAZYVA), AME-133v (APPLIED MOLECULAR EVOLUTION), Ocrelizumab (GENENTECH), TRU-015 (TRUBION/EMERGENT), veltuzumab (IMMU-106).

In some embodiments, the present invention relates to combination therapy with one or more chimeric agents described in WO 2013/10779, WO 2015/007536, WO 2015/

007520, WO 2015/007542, and WO 2015/007903, the entire contents of which are hereby incorporated by reference in their entireties.

In some embodiments, the chimeric protein described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc.

In still other embodiments, the chimeric protein described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The chimeric protein described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Illustrative cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the vinca alkaloids, vincristine and vinblastine. Other cytotoxic agents include paclitaxel (taxol), ricin, pseudomonas exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine, bleomycin, VEGF antagonists, EGFR antagonists, platins, taxols, irinotecan, 5-fluorouracil, gemcytabine, leucovorine, steroids, cyclophosphamide, melphalan, vinca alkaloids (e.g., vinblastine, vincristine, vindesine and vinorelbine), mustines, tyrosine kinase inhibitors, radiotherapy, sex hormone antagonists, selective androgen receptor modulators, selective estrogen receptor modulators, PDGF antagonists, TNF antagonists, IL-1 antagonists, interleukins (e.g. IL-12 or IL-2), IL-12R antagonists, Toxin conjugated monoclonal antibodies, tumor antigen specific monoclonal antibodies, Erbitux, Avastin, Pertuzumab, anti-CD20 antibodies, Rituxan, ocrelizumab, ofatumumab, DXL625, HERCEPTIN®, or any combination thereof. Toxic enzymes from plants and bacteria such as ricin, diphtheria toxin and *Pseudomonas* toxin may be conjugated to the therapeutic agents (e.g. antibodies) to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the chimeric protein, with or without the use of a complex-forming agent. Such radionuclides include beta-emitters such as Phosphorus-32, Scandium-47, Copper-67, Gallium-67, Yttrium-88, Yttrium-90, Iodine-125, Iodine-131, Samarium-153, Lutetium-177, Rhenium-186 or Rhenium-188, and alpha-emitters such as Astatine-211, Lead-212, Bismuth-212, Bismuth-213 or Actinium-225.

Illustrative detectable moieties further include, but are not limited to, horseradish peroxidase, acetylcholinesterase, alkaline phosphatase, beta-galactosidase and luciferase. Further illustrative fluorescent materials include, but are not limited to, rhodamine, fluorescein, fluorescein isothiocyanate, umbelliferone, dichlorotriazinylamine, phycoerythrin and dansyl chloride. Further illustrative chemiluminescent moieties include, but are not limited to, luminol. Further illustrative bioluminescent materials include, but are not limited to, luciferin and aequorin. Further illustrative radioactive materials include, but are not limited to, Iodine-125, Carbon-14, Sulfur-35, Tritium and Phosphorus-32.

Methods of Treatment

Methods and compositions described herein have application to treating various diseases and disorders, including, but not limited to cancer, infections, immune disorders, autoimmune diseases, and many other diseases and disorders.

Further, any of the present agents may be for use in the treating, or the manufacture of a medicament for treating, various diseases and disorders, including, but not limited to cancer, infections, immune disorders, and autoimmune diseases.

In some embodiments, the present invention relates to the treatment of, or a patient having cancer. As used herein, cancer refers to any uncontrolled growth of cells that may interfere with the normal functioning of the bodily organs and systems, and includes both primary and metastatic tumors. Primary tumors or cancers that migrate from their original location and seed vital organs can eventually lead to the death of the subject through the functional deterioration of the affected organs. A metastasis is a cancer cell or group of cancer cells, distinct from the primary tumor location, resulting from the dissemination of cancer cells from the primary tumor to other parts of the body. Metastases may eventually result in death of a subject. For example, cancers can include benign and malignant cancers, polyps, hyperplasia, as well as dormant tumors or micrometastases.

Illustrative cancers that may be treated include, but are not limited to, carcinomas, e.g. various subtypes, including, for example, adenocarcinoma, basal cell carcinoma, squamous cell carcinoma, and transitional cell carcinoma), sarcomas (including, for example, bone and soft tissue), leukemias (including, for example, acute myeloid, acute lymphoblastic, chronic myeloid, chronic lymphocytic, and hairy cell), lymphomas and myelomas (including, for example, Hodgkin and non-Hodgkin lymphomas, light chain, non-secretory, MGUS, and plasmacytomas), and central nervous system cancers (including, for example, brain (e.g. gliomas (e.g. astrocytoma, oligodendroglioma, and ependymoma), meningioma, pituitary adenoma, and neuromas, and spinal cord tumors (e.g. meningiomas and neurofibroma).

Illustrative cancers that may be treated include, but are not limited to, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In some embodiments, the present invention relates to the treatment of, or a patient having a microbial infection and/or chronic infection. Illustrative infections include, but are not limited to, HIV/AIDS, tuberculosis, osteomyelitis, hepatitis B, hepatitis C, Epstein-Barr virus or parvovirus, T cell leukemia virus, bacterial overgrowth syndrome, fungal or parasitic infections.

In various embodiments, the present compositions are used to treat or prevent one or more inflammatory diseases or conditions, such as inflammation, acute inflammation, chronic inflammation, respiratory disease, atherosclerosis, restenosis, asthma, allergic rhinitis, atopic dermatitis, septic shock, rheumatoid arthritis, inflammatory bowel disease, inflammatory pelvic disease, pain, ocular inflammatory disease, celiac disease, Leigh Syndrome, Glycerol Kinase Deficiency, Familial eosinophilia (FE), autosomal recessive spastic ataxia, laryngeal inflammatory disease; Tuberculosis, Chronic cholecystitis, Bronchiectasis, Silicosis and other pneumoconioses.

In various embodiments, the present compositions are used to treat or prevent one or more autoimmune diseases or conditions, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

Kits

The invention also provides kits for the administration of any agent described herein (e.g. the chimeric protein with or without various additional therapeutic agents). The kit is an assemblage of materials or components, including at least one of the inventive pharmaceutical compositions described herein. Thus, in some embodiments, the kit contains at least one of the pharmaceutical compositions described herein.

The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to effect a desired outcome, such as to treat cancer.

Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner stored in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose.

A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein. This invention is further illustrated by the following non-limiting examples.

EXAMPLES

In the following examples, unless noted, mutations to IFN are relative to human IFN-α2-SEQ ID NO: 179.

The Q124R mutant is representative of an attenuated human IFN alpha 2 mutant that can be assayed in vivo in a murine model. Specifically, Q124R is a human IFN mutation that is suitable for use in the mouse (i.e. it is a human mutant IFN that functions in mouse). See *Nat. Comm.* 2014; 5:3016. doi: 10.1038/ncomms4016, the entire contents of which are hereby incorporated by reference.

Anti-human PD-1 VHH used in these Examples is SEQ ID NO: 23.

Anti-human PD-L1 VHH used in these Examples is SEQ ID NO: 158.

Example 1: Characterization of Anti-Mouse PD-L1/Attenuated Human IFN Chimera FIG. 1 shows the anti-tumor activities of an anti-PD-L1-human IFN Q124R chimera construct as compared to anti-PD-L1 VHH and PBS. In the experiment, C57BL/6 mice were inoculated subcutaneously (50 μl) with $6\times10^5$ B16mCD20cl1 melanoma tumor cells (a mouse melanoma cell line). Perilesional treatment with 30 μg of various constructs (100 μl) was started when tumors reached a size of ±10 $mm^2$ as measured by caliper. FIG. 1 shows that anti-PD-L1 had minimal effect in the B16 tumor model while the anti-PD-L1-human IFN Q124R chimera showed anti-tumor activity and reduced tumor size.

Figure 2:
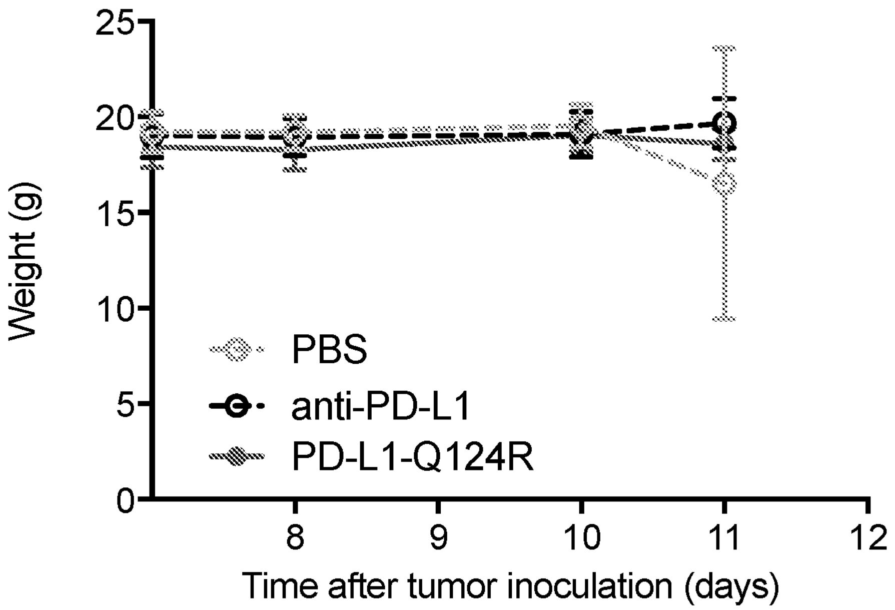
FIG. 2 shows, in panels A-G, safety data that correspond with the efficacy data of FIG. 1. In panel A, the weight of mice is shown for all treatment types. In panels B-G, all of the data is presented as histograms in sets of three which are, from left to right: PBS, anti-PD-L1 VHH, and fusion of an anti-PD-L1 VHH to human IFNalpha, Q124R. Shown are white blood cell counts ("wbc") and lymphocytes count ("ly") (panel B), neutrophil count ("ne") and monocyte count ("mo") (panel C); red blood cell count ("rbc") and hemoglobin ("hb") (panel D); hemocrit ("hct"), mean corpuscular volume ("mcv"), mean corpuscular hemoglobin ("mch"), mean corpuscular hemoglobin concentration ("mchc") (panel E); pitted red blood cells ("pit") (panel F); and mean platelet volume ("mpv") (panel G).
Figure 2:
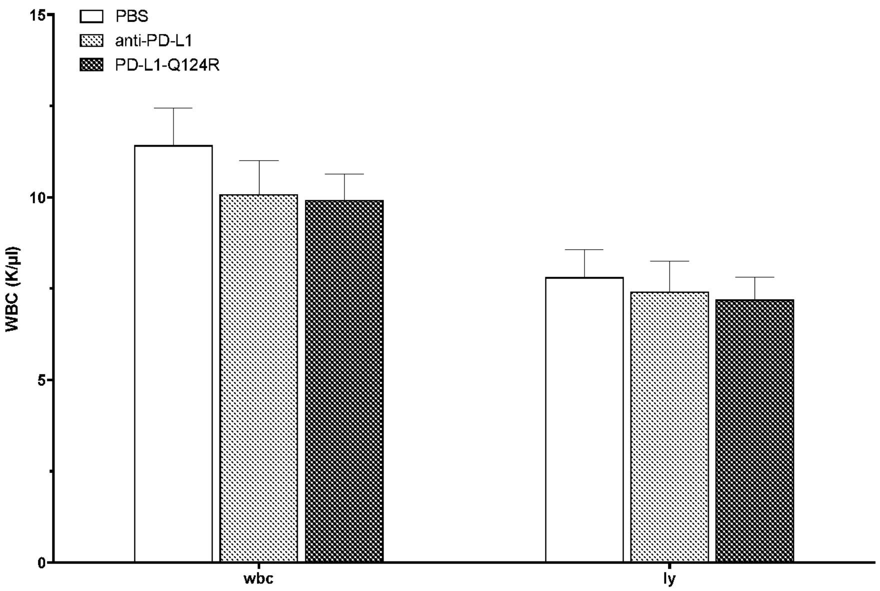
Figure 2:
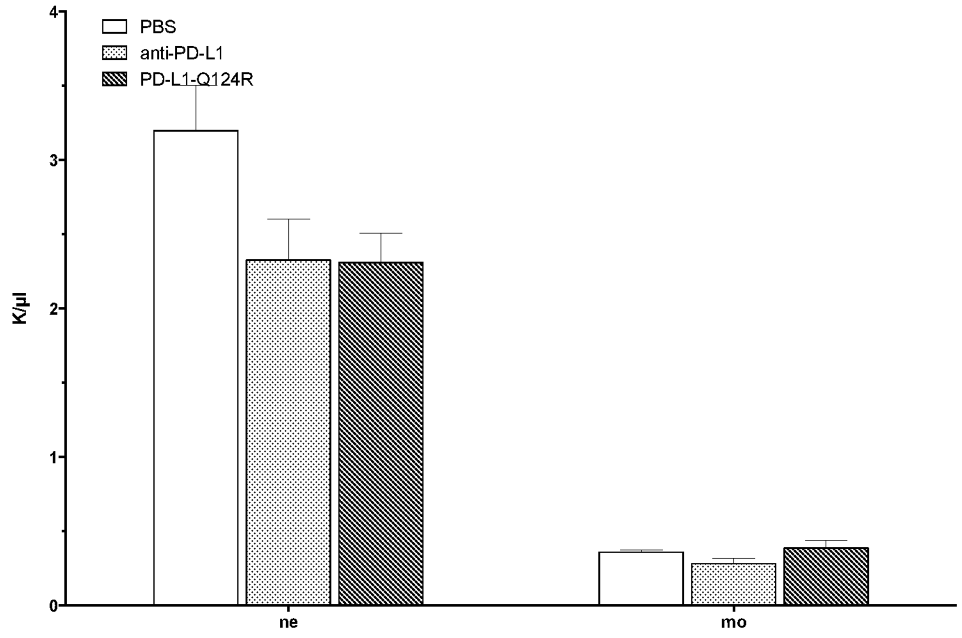
Figure 2:
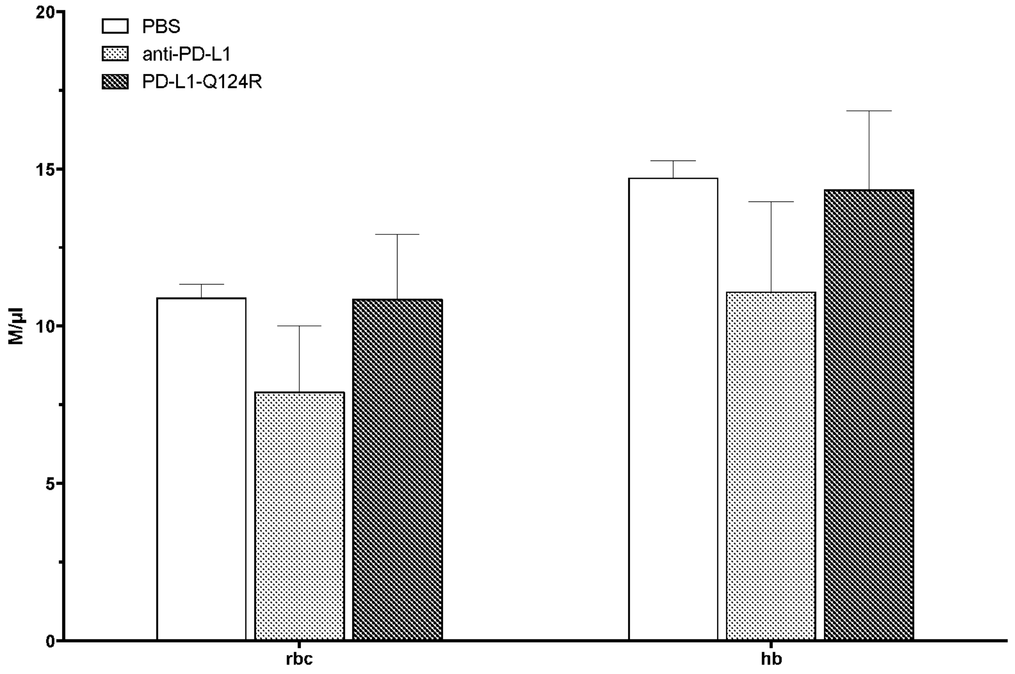
Figure 2:
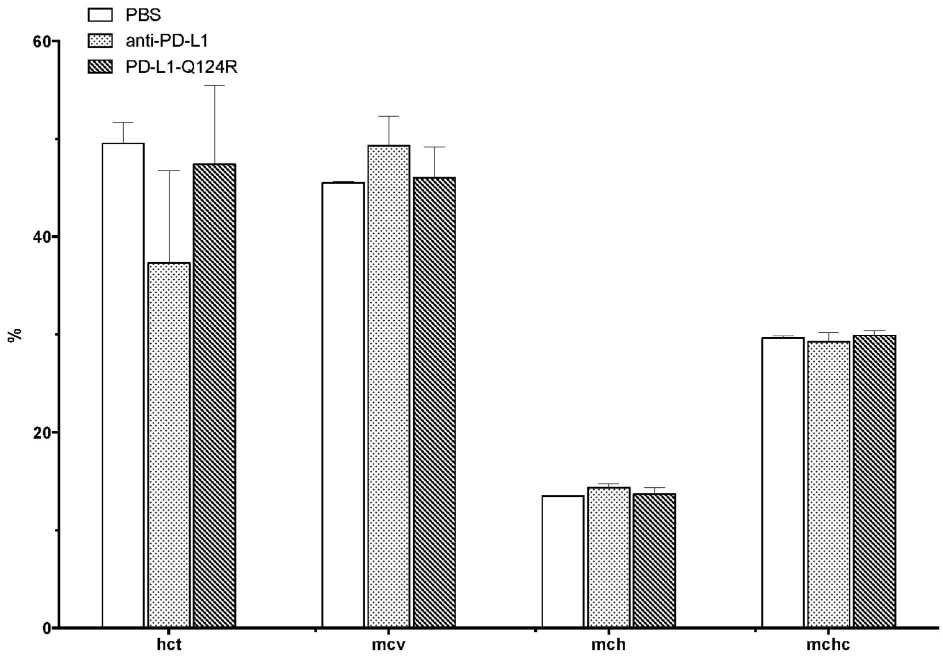
Figure 2:
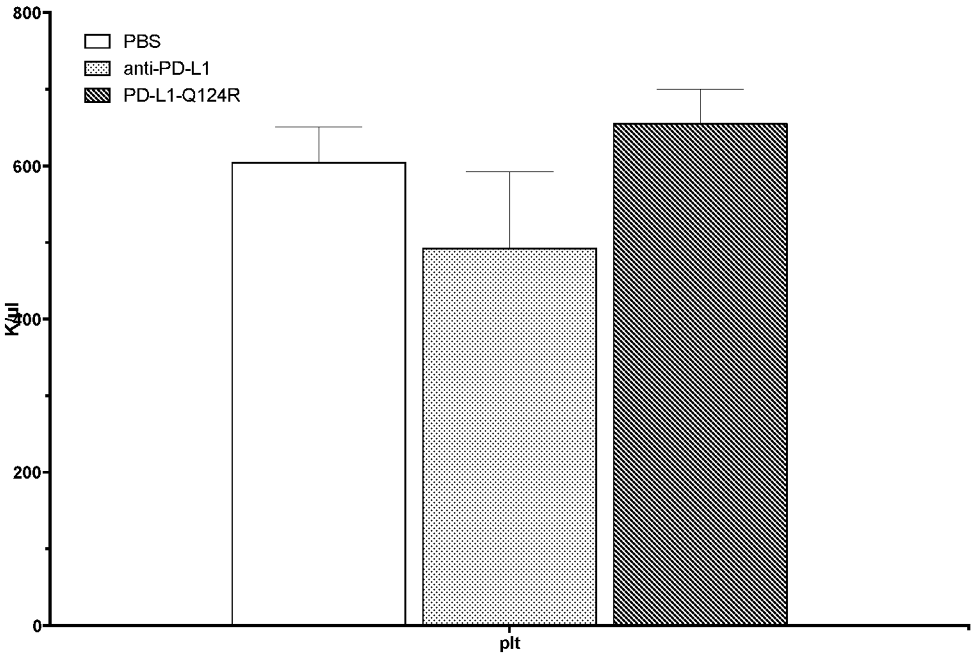
Figure 2:
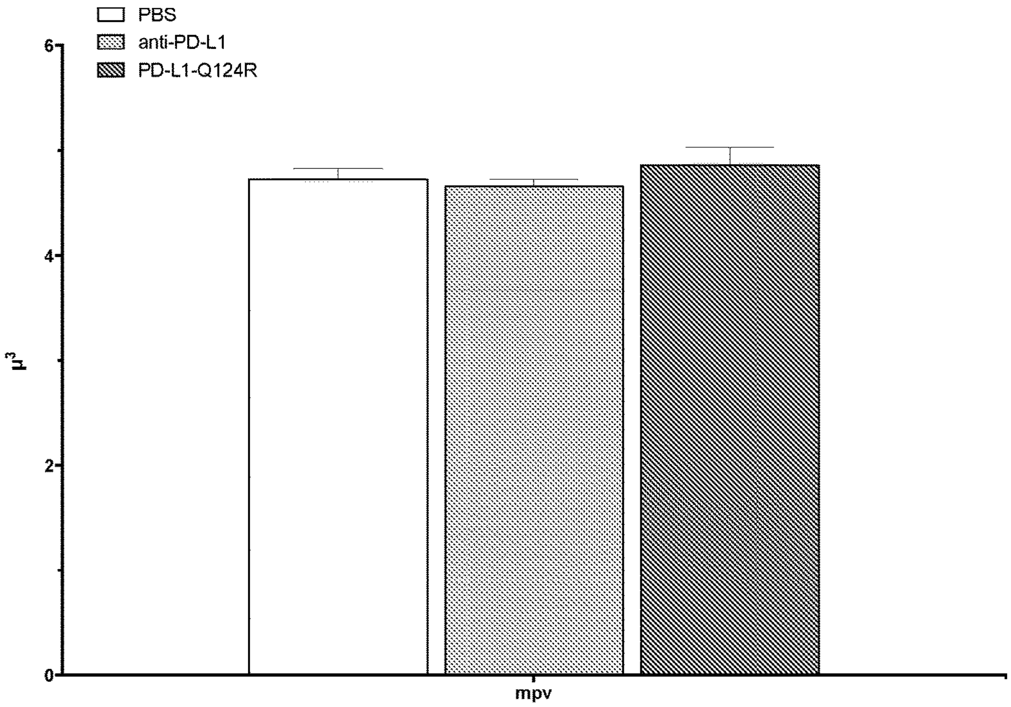
Figure 4:
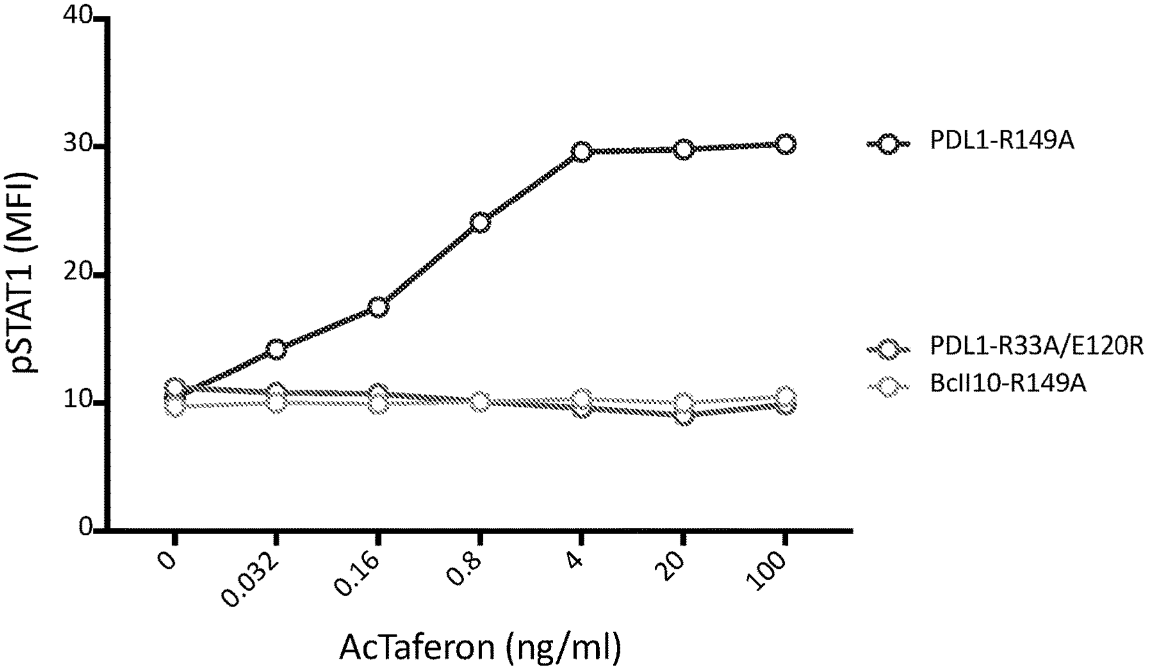
FIG. 4 shows an experiment in which MDA-MB-321 cells were stimulated with a serial dilution anti-PD-L1/attenuated IFN chimeras and stained for phospho STAT1. Data are plotted as mean fluorescent intensities (MFI). The top curve is anti-human PD-L1 VHH/human IFN R149A.

The anti-PD-L1-human IFN Q124R chimera was also shown to be safe (FIG. 2). In each figure, panels A-G show: change in body weight of the mice in the tumor studies described above (panel A), white blood cell counts ("wbc") and lymphocytes count ("ly") (panel B), neutrophil count ("ne") and monocyte count ("mo") (panel C); red blood cell count ("rbc") and, for FIG. 4, hemoglobin ("hb") (panel D);

hemocrit ("hct"), mean corpuscular volume ("mcv"), mean corpuscular hemoglobin ("mch"), mean corpuscular hemoglobin concentration ("mchc") (panel E); pitted red blood cells ("pit") (panel F); and mean platelet volume ("mpv") (panel G). Importantly, the anti-PD-L1-human IFN Q124R chimera showed safety parameters that were far superior than what was expected from wild type interferons.

Example 2: Characterization of Anti-Human PD1 and PD-L1 VHHs

PD-1 (programmed cell death protein 1) functions as an immune checkpoint and plays an important role in the down regulation of the immune system by preventing activation of T-cells by binding to its ligands PD-L1 (programmed death-ligand 1) and PD-L2. A plate-binding assay was set up to evaluate the effect of PD-1 and PD-L1 VHHs on the interaction between these two proteins.

Specifically, maxisorp plates were coated overnight with anti-FLAG Ab (Sigma; 2 μg/ml in PBS), washed with washing buffer (PBS+0,05% Tween-20) and blocked with PBS+5% Tween-20 (2 hours at room temperature). Conditioned medium containing FLAG-tagged hPD-L1 extracellular domain was incubated for two hours at room temperature. Excess unbound protein was washed away with washing buffer. hPD1-Fc (500 ng/ml; R&D systems; cat: 1086-PD) in the presence or absence of VHHs was allowed to bind for 2 hours at room temperature. Bound hPD1-Fc was quantified with an horseradish peroxidase (HRP)-coupled anti-human secondary AB and the TMB HRP substrate (KPL).

Figure 3:
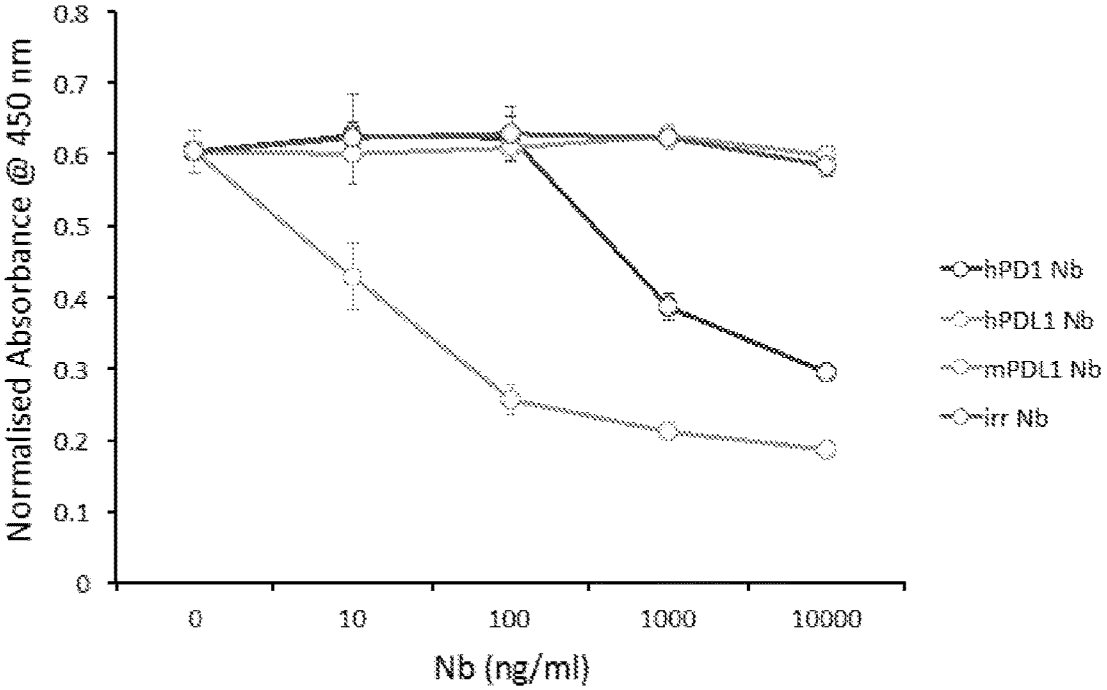
FIG. 3 shows the effect of a serial dilution of anti-human PD-1 VHHs, anti-human PD-L1 VHHs, anti-mouse PD-L1 VHHs or irrelevant VHHs when tested in a PD1/PD-L1 plate-binding assay. Average±standard deviation of triplicate measurements are plotted. At the 10,000 point, the curves from top to bottom are: anti-mouse PD-L1 VHHs, irrelevant VHHs, anti-human PD-1 VHHs, and anti-human PD-L1 VHHs.

In this experiment, hPD-1-Fc was allowed to bind to immobilized hPD-L1 in the presence of a serial dilution (1000 ng/ml; 1 over 10) of VHHs specific for hPD-1, hDP-L1, mPD-L1 or an irrelevant target. Data clearly illustrate that both hPD-1 and hPD-L1 VHHs blocked the interaction PD-1/PD-L1, while no effect for mPD-L1 or irrelevant VHHs was observed. See FIG. 3.

Example 3: Anti-Human PD-L1 Targeting of IFN Chimeras

Efficiency of human PD-L1 (programmed death-ligand 1)/attenuated IFN chimera ("AcTaferon") targeting was examined by quantification of STAT1 phosphorylation in the human PD-L1 positive MDA-MB-321 cell-line by FACS analysis.

Specifically, MDA-MB-321 cells were stimulated with anti-human PD-L1/attenuated IFN chimeras as indicated for 15 minutes at 37° C. in DMEM medium supplemented with 10% FBS. After stimulation, cells were fixed by adding 1 volume Fix Buffer I (BD Biosciences) for 10 minutes at 37° C., and permeabilized by resuspension in 2 volumes Perm III Buffer I (BD Biosciences) for 30 minutes on ice. Samples were stained with an anti-STAT1 pY701 Ab (BD Biosciences) for 20 minutes at 4° C. and analyzed with a FACSCalibur (BD Biosciences) and the CellQuest Pro Version 4.0.2 software (BD Biosciences).

In this experiment, MDA-MB-321 cells were stimulated with a serial dilution (100 ng/ml; 1 over 5) of anti-human PD-L1/attenuated IFN chimeras for 15 minutes at 37° C. After fixation and permeabilization, cells were stained for phospho STAT1 and analyzed in FACS. Data clearly illustrate that PD-L1 targeting of anti-human PD-L1/attenuated IFN chimeras strongly increased STAT1 phosphorylation of anti-human PD-L1/attenuated R149A IFN chimeras, but not anti-human PD-L1/attenuated R33A/E120R IFN chimeras. Untargeted (BcII10 VHH) chimera was unable to signal even at 100 ng/ml. See FIG. 4.

Example 4: Signaling Induction in Human Dendritic Cells with Anti-Human PD-L1 VHH Chimeras A dendritic cell pSTAT signaling assay was undertaken. Chimeras studied were anti-human PD-L1 VHH/human IFN R149A and anti-human PD-L1 VHH/human IFN R33A/E120R. Two doses of the agents were studied: 100 ng/ml and 500 ng/ml.

Briefly, human PBMCs were isolated from blood obtained from healthy donors. Approximately 120 ml of blood was collected from each donor using heparin coated tubes (12 tubes). The blood was kept at room temperature and processed immediately Briefly, blood was diluted 1:1 with DPBS and 25 ml was gently layered onto 15 ml of Lympholyte H. After centrifugation, the mononuclear cell rings were collected and cells were washed three times with DPBS (PBS Dulbecco's Phosphate Buffered Saline, Wisent, catalog #311-425-LL) and counted. Dendritic cells were enriched from the PBMC population using "DC-enrichment kit" containing a combination of lineage specific monoclonal antibodies in PBS and a suspension of magnetic particles (STEMCELL Technologies Catalogue number 19251), according to manufacturer's instructions.

Dendritic cells (DC) were stimulated for 15 minutes in the presence or absence of test items and controls (PBS) and the level of phosphorylated-STAT1 (pSTAT1, specifically pY701-STAT1) was determined in isolated DC cell populations (Lin-(CD14/CD16/CD20/CD56/CD3)/HLA−DR+) by flow cytometry. Post stimulation, cells were fixed (BD Cytofix fixation buffer, BD Bioscience, catalog #554655), then permeabilized with Perm buffer II (BD PhosFlow Perm Buffer, BD Bioscience, catalog #558052). Cells were then stained for phosphoSTAT1 and for DC surface markers (Lin−/HLA-DR+) (see table below). Both intra-cellular and surface staining were performed at the same time. Flow cytometry and data acquisition was performed after cell washing with DPBS.

Table showing list of antibodies for flow cytometry staining

| Marker/Product Name | Fluorochrome | Clone | Purpose | Supplier-Catalog Number |
|---|---|---|---|---|
| pSTAT1 | AlexaFluor647 | 4a | Phosphor-STAT1 | BD-562070 |
| Anti-human CD3 | PE | UCHT1 | T cells marker Lineage deletion | BD-561809 |
| Anti-human CD14 | PE | M5E2 | Monocytes markers Lineage depletion | BD-555398 |

-continued

| Marker/Product Name | Fluorochrome | Clone | Purpose | Supplier-Catalog Number |
|---|---|---|---|---|
| anti-human CD16 | PE | B73.1 | NK, Neutrophils, Monocytes marker Lineage depletion | BD-561313 |
| anti-human CD19 | PE | HIB19 | B cells marker Lineage depletion | BD-555413 |
| anti-human CD56 | PE | B159 | NK cells marker Lineage depletion | BD-555516 |
| Anti-human HLA-DR | FITC | TU36 | MHC II marker DC discrimination | BD-555560 |
| Anti-human CD11c | BV421 | B-Ly6 | DC discrimination | BD-562561 |
| LIVE/DEAD Fixable Aqua Dead Cell Stain | Aqua | N/Ap | Viability dye | ThermoFisher-L34957 |
| Normal mouse IgG | N/Ap | N/Ap | Fc receptor blocker Blocking agent | Thermo Fisher-10400C |

Figure 5:
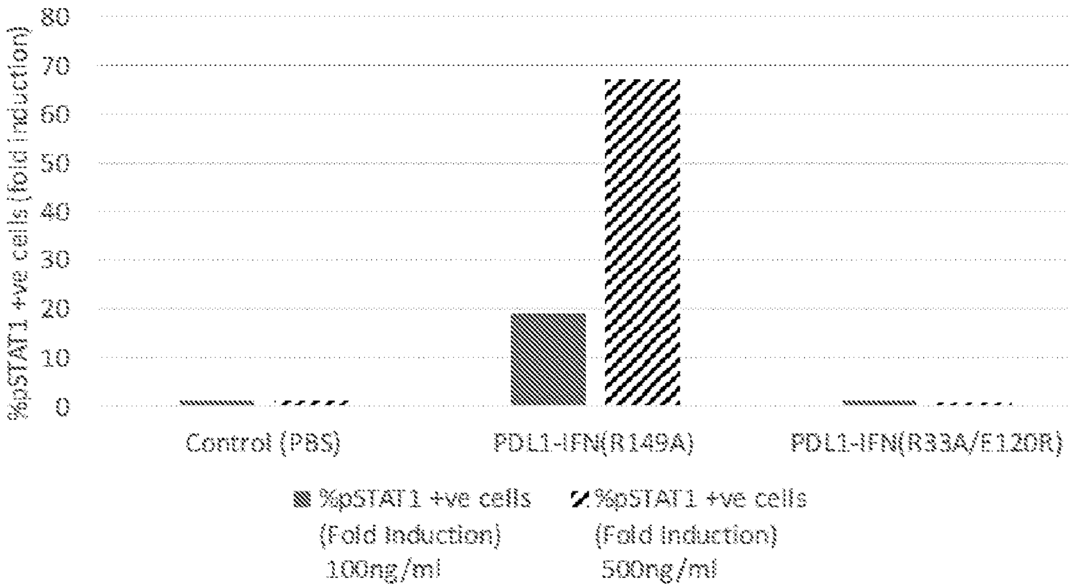
FIG. 5 shows a human dendritic cell pSTAT1 signaling assay. Chimeras studied were anti-human PD-L1 VHH/human IFN R149A and anti-human PD-L1 VHH/human IFN R33A/E120R. Two doses of the agents were studied: 100 ng/ml and 500 ng/ml. PBS was the control and the data are expressed as a fold change of the percentage of $pSTAT1^+$ dendritic cells (data is an average of a triplicate data set).

FIG. 5 shows the data, expressed as a fold change of the percentage of $pSTAT^+$ dendritic cells.

This study clearly shows that a human PD-L1 antigen-targeting construct comprising an IFN signaling agent whose activity is recoverable upon cell targeting (IFN R149A) promotes IFN signaling in human dendritic cells (as determined by pSTAT1 induction). In contrast, no IFN signaling activation is observed with a PD-L1-targeting construct that incorporates an IFN signaling agent whose activity is not recoverable (IFN R33A/E120R). Thus, as observed for comparable IFN fusion constructs targeting mouse PD-L1, targeting IFN to human dendritic cells using a targeting moiety directed at human PD-L1 antigen results in triggering of a pronounced IFN signal transduction.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for treating cancer, comprising administering to a subject in need thereof an effective amount of a chimeric protein comprising:

(a) a targeting moiety that comprises a recognition domain that recognizes and binds to programmed cell death protein 1 ligand 1 (PD-L1), wherein the targeting moiety comprises a recombinant heavy-chain-only antibody (VHH), a single-chain antibody (scFv), or a shark heavy-chain-only antibody (VNAR); and (b) a modified signaling agent, wherein the modified signaling agent is a human interferon alpha 2 (IFNα2) comprising an amino acid sequence having at least 98% identity with a sequence selected from SEQ ID NO: 179 or 180 and having one or more mutations at one or more position of amino acids 144-154, wherein the mutated human IFNα2 has reduced affinity or activity as compared to wild type human IFNα2, and the reduced affinity or activity of the mutated human IFNα2 is restorable by the targeting moiety, wherein the cancer comprises cells expressing PD-L1.

2. The method of claim 1, wherein the mutation is at one or more of positions R149, L153, and M148.

3. The method of claim 1, wherein the mutation is R149A.

4. The method of claim 1, wherein the mutation is L153A.

5. The method of claim 1, wherein the mutation is M148A.

6. The method of claim 1, wherein the targeting moiety comprises a VHH.

7. The method of claim 1, wherein the targeting moiety recognizes and binds PD-L1 without functionally modulating its activity.

8. The method of claim 1, wherein the targeting moiety recognizes and binds PD-L1 and functionally modulates its activity.

9. The method of claim 1, wherein the chimeric protein comprises one or more additional targeting moieties.

10. The method of claim 1, wherein the cancer is selected from one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer; glioblastoma; hepatic carcinoma; hepatoma; intra-epithelial neoplasm; kidney or renal cancer; larynx cancer; leukemia; liver cancer; lung cancer; small-cell lung cancer; non-small cell lung cancer; adenocarcinoma of the lung; squamous carcinoma of the lung; melanoma; myeloma; neuroblastoma; oral cavity cancer; ovarian cancer; pancreatic cancer; prostate cancer; retinoblastoma; rhabdomyosarcoma; rectal cancer; cancer of the respiratory system; salivary gland carcinoma; sarcoma; Kaposi's sarcoma; skin cancer; squamous cell cancer; stomach cancer; testicular cancer; thyroid cancer; uterine or endometrial cancer; cancer of the urinary system; vulval cancer; lymphoma; Hodgkin's lymphoma; non-Hodgkin's lymphoma; B-cell lymphoma; low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; Waldenstrom's Macroglobulinemia; chronic lymphocytic leukemia (CLL); acute lymphoblastic leukemia (ALL); hairy cell leukemia; chronic myeloblastic leukemia; post-transplant lymphoproliferative disorder (PTLD); abnormal vascular proliferation associated with phakomatoses; and Meigs' syndrome.

* * * * *